US010595867B2

(12) United States Patent
Bolduc et al.

(10) Patent No.: US 10,595,867 B2
(45) Date of Patent: *Mar. 24, 2020

(54) SYSTEMS AND METHODS FOR ATTACHING A PROSTHESIS WITHIN A BODY LUMEN OR HOLLOW ORGAN

(71) Applicant: Medtronic Vascular, Inc., Minneapolis, MN (US)

(72) Inventors: Lee Bolduc, Sunnyvale, CA (US); Philip Houle, Sunnyvale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 423 days.

This patent is subject to a terminal disclaimer.

(21) Appl. No.: 15/611,596

(22) Filed: Jun. 1, 2017

(65) Prior Publication Data
US 2017/0303922 A1 Oct. 26, 2017

Related U.S. Application Data

(60) Division of application No. 14/210,683, filed on Mar. 14, 2014, now Pat. No. 9,808,250, which is a
(Continued)

(51) Int. Cl.
*A61B 17/10* (2006.01)
*A61B 17/064* (2006.01)
(Continued)

(52) U.S. Cl.
CPC ............ *A61B 17/10* (2013.01); *A61B 17/064* (2013.01); *A61B 17/068* (2013.01); *A61B 17/08* (2013.01); *A61B 17/115* (2013.01); *A61F 2/07* (2013.01); *A61B 17/083* (2013.01); *A61B 2017/0649* (2013.01); *A61B 2090/037* (2016.02); *A61F 2/848* (2013.01); *A61F 2/89* (2013.01);
(Continued)

(58) Field of Classification Search
None
See application file for complete search history.

(56) References Cited

U.S. PATENT DOCUMENTS 2,033,039 A   3/1936 Limpert
3,499,222 A   3/1970 Linkow et al.
(Continued)

FOREIGN PATENT DOCUMENTS

AU   2002353807 B2   6/2003
AU   2004277897 B2   4/2005
(Continued)

OTHER PUBLICATIONS

"5mm Origin Tracker It Runs in Circles Around Staples", Guidant Origin Advertising Literature, (1995), 2 pgs.
(Continued)

*Primary Examiner* — Shaun L David

(57) ABSTRACT

Systems and methods introduce and deploy prosthesis into a blood vessel or hollow body organ by intra-vascular access. The prosthesis is secured in place by fasteners which are implanted by an applier that is also deployed by intra-vascular access. The applier is configured to permit controlled, selective release of the fastener in a step that is independent of the step of implantation.

12 Claims, 25 Drawing Sheets

Related U.S. Application Data continuation of application No. 13/495,839, filed on Jun. 13, 2012, now Pat. No. 8,685,044, which is a continuation of application No. 10/786,465, filed on Feb. 25, 2004, now Pat. No. 8,231,639, which is a continuation-in-part of application No. 10/693,255, filed on Oct. 24, 2003, now Pat. No. 6,929,661, which is a continuation-in-part of application No. 10/307,226, filed on Nov. 29, 2002, now Pat. No. 8,075,570, which is a continuation-in-part of application No. 10/271,334, filed on Oct. 15, 2002, now Pat. No. 6,960,217.

(60) Provisional application No. 60/489,011, filed on Jul. 21, 2003, provisional application No. 60/333,937, filed on Nov. 28, 2001.

(51) Int. Cl.

| | | |
|---|---|---|
| A61B 17/068 | (2006.01) | |
| A61B 17/08 | (2006.01) | |
| A61B 17/115 | (2006.01) | |
| A61F 2/07 | (2013.01) | |
| A61F 2/848 | (2013.01) | |
| A61B 90/00 | (2016.01) | |
| A61F 2/89 | (2013.01) | |

(52) U.S. Cl.
CPC ... *A61F 2002/072* (2013.01); *A61F 2002/075* (2013.01); *A61F 2220/0016* (2013.01); *A61F 2250/0017* (2013.01)

(56) References Cited

U.S. PATENT DOCUMENTS

| | | | |
|---|---|---|---|
| 3,686,740 A | 8/1972 | Donald | |
| 3,799,172 A | 3/1974 | Roman | |
| 4,140,126 A | 2/1979 | Choudhury | |
| 4,255,820 A | 3/1981 | Rothermel et al. | |
| 4,307,722 A | 12/1981 | Evans | |
| 4,580,568 A | 4/1986 | Gianturco | |
| 4,586,923 A | 5/1986 | Gould et al. | |
| 4,625,597 A | 12/1986 | Cast | |
| 4,694,827 A | 9/1987 | Weiner et al. | |
| 4,781,682 A | 11/1988 | Patel | |
| 4,822,345 A | 4/1989 | Danforth | |
| 4,898,577 A | 2/1990 | Badger et al. | |
| 4,899,747 A | 2/1990 | Garren et al. | |
| 4,921,484 A | 5/1990 | Hillstead | |
| 4,990,151 A | 2/1991 | Wallsten | |
| 4,994,071 A | 2/1991 | MacGregor | |
| 5,015,249 A * | 5/1991 | Nakao | A61B 17/10 227/901 |
| 5,030,204 A | 7/1991 | Badger et al. | |
| 5,042,707 A | 8/1991 | Taheri | |
| 5,044,519 A | 9/1991 | Aoyama | |
| 5,071,407 A | 12/1991 | Termin et al. | |
| 5,104,399 A | 4/1992 | Lazarus | |
| 5,156,609 A * | 10/1992 | Nakao | A61B 17/0682 227/179.1 |
| 5,185,004 A | 2/1993 | Lashinski et al. | |
| 5,192,314 A | 3/1993 | Daskalakis | |
| 5,195,968 A | 3/1993 | Lundquist et al. | |
| 5,199,950 A | 4/1993 | Schmitt et al. | |
| 5,207,695 A | 5/1993 | Trout, III | |
| 5,222,961 A * | 6/1993 | Nakao | A61B 17/10 606/142 |
| 5,282,824 A | 2/1994 | Gianturco | |
| 5,290,295 A | 3/1994 | Querals et al. | |
| 5,318,525 A | 6/1994 | West et al. | |
| 5,320,630 A | 6/1994 | Ahmed | |
| 5,330,490 A | 7/1994 | Wilk et al. | |
| 5,330,503 A | 7/1994 | Yoon | |
| 5,334,196 A | 8/1994 | Scott et al. | |
| 5,352,197 A | 10/1994 | Hammersmark et al. | |
| 5,364,351 A | 11/1994 | Heinzelman et al. | |
| 5,383,880 A | 1/1995 | Hooven et al. | |
| 5,387,235 A | 2/1995 | Chuter | |
| 5,392,978 A * | 2/1995 | Velez | A61B 17/0644 227/175.1 |
| 5,409,498 A | 4/1995 | Braddock et al. | |
| 5,425,489 A * | 6/1995 | Shichman | A61B 17/0643 227/108 |
| 5,456,713 A | 10/1995 | Chuter | |
| 5,456,714 A | 10/1995 | Owen | |
| 5,470,337 A | 11/1995 | Moss | |
| 5,474,568 A | 12/1995 | Scott et al. | |
| 5,480,382 A | 1/1996 | Hammerslag et al. | |
| 5,480,423 A | 1/1996 | Ravenscroft et al. | |
| 5,489,295 A | 2/1996 | Piplani et al. | |
| 5,522,881 A | 6/1996 | Lentz | |
| 5,531,686 A | 7/1996 | Lundquist et al. | |
| 5,534,007 A | 7/1996 | St. Germain et al. | |
| 5,562,728 A | 10/1996 | Lazarus et al. | |
| 5,571,171 A | 11/1996 | Barone et al. | |
| 5,571,173 A | 11/1996 | Parodi | |
| 5,582,616 A * | 12/1996 | Bolduc | A61B 17/064 606/139 |
| 5,591,195 A | 1/1997 | Taheri et al. | |
| 5,609,627 A | 3/1997 | Goicoechea et al. | |
| 5,626,613 A | 5/1997 | Schmieding | |
| 5,628,788 A | 5/1997 | Pinchuk | |
| 5,632,772 A | 5/1997 | Alcime et al. | |
| 5,634,936 A | 6/1997 | Linden et al. | |
| 5,639,278 A | 6/1997 | Dereume et al. | |
| 5,662,675 A | 9/1997 | Polanskyj Stockert et al. | |
| 5,662,683 A * | 9/1997 | Kay | A61B 17/0401 411/425 |
| 5,662,700 A | 9/1997 | Lazarus | |
| 5,676,696 A | 10/1997 | Marcade | |
| 5,676,697 A | 10/1997 | Mcdonald | |
| 5,683,450 A | 11/1997 | Goicoechea et al. | |
| 5,693,084 A | 12/1997 | Chuter | |
| 5,693,086 A | 12/1997 | Goicoechea et al. | |
| 5,695,524 A * | 12/1997 | Kelley | A61B 17/0644 227/902 |
| 5,700,269 A | 12/1997 | Pinchuk et al. | |
| 5,702,343 A | 12/1997 | Alferness | |
| 5,702,365 A | 12/1997 | King St. | |
| 5,702,408 A | 12/1997 | Wales et al. | |
| 5,707,376 A | 1/1998 | Kavteladze et al. | |
| 5,713,907 A | 2/1998 | Hogendijk et al. | |
| 5,733,325 A | 3/1998 | Robinson et al. | |
| 5,749,921 A | 5/1998 | Lenker et al. | |
| 5,755,777 A | 5/1998 | Chuter | |
| 5,762,458 A | 6/1998 | Wang et al. | |
| 5,769,884 A | 6/1998 | Solovay | |
| 5,776,142 A | 7/1998 | Gunderson | |
| 5,779,731 A | 7/1998 | Leavitt | |
| 5,782,844 A * | 7/1998 | Yoon | A61B 17/064 606/139 |
| 5,797,933 A | 8/1998 | Snow et al. | |
| 5,800,528 A | 9/1998 | Lederman et al. | |
| 5,810,882 A | 9/1998 | Bolduc et al. | |
| 5,814,016 A | 9/1998 | Valley | |
| 5,824,008 A | 10/1998 | Bolduc et al. | |
| 5,824,037 A | 10/1998 | Fogarty et al. | |
| 5,824,041 A | 10/1998 | Lenker et al. | |
| 5,830,221 A * | 11/1998 | Stein | A61B 17/068 606/157 |
| 5,830,229 A | 11/1998 | Konya et al. | |
| 5,843,160 A | 12/1998 | Rhodes | |
| 5,855,565 A | 1/1999 | Bar-Cohen et al. | |
| 5,855,598 A | 1/1999 | Pinchuk | |
| 5,861,003 A | 1/1999 | Latson et al. | |
| 5,865,791 A | 2/1999 | Whayne et al. | |
| 5,876,432 A | 3/1999 | Lau et al. | |
| 5,904,713 A | 5/1999 | Leschinsky | |
| 5,906,619 A | 5/1999 | Olson et al. | |
| 5,906,641 A | 5/1999 | Thompson et al. | |
| 5,916,263 A | 6/1999 | Goicoechea et al. | |
| 5,944,750 A | 8/1999 | Tanner et al. | |

(56) References Cited

U.S. PATENT DOCUMENTS

| | | |
|---|---|---|
| 5,957,940 A | 9/1999 | Tanner et al. |
| 5,964,772 A | 10/1999 | Bolduc et al. |
| 5,968,053 A | 10/1999 | Revelas |
| 5,972,003 A | 10/1999 | Rousseau et al. |
| 5,972,023 A | 10/1999 | Tanner et al. |
| 5,980,548 A | 11/1999 | Evans et al. |
| 5,993,401 A | 11/1999 | Inbe et al. |
| 5,993,466 A | 11/1999 | Yoon |
| 5,997,556 A | 12/1999 | Tanner et al. |
| 6,016,810 A | 1/2000 | Ravenscroft |
| 6,024,703 A | 2/2000 | Zanelli et al. |
| 6,024,763 A | 2/2000 | Lenker et al. |
| 6,027,462 A | 2/2000 | Greene et al. |
| 6,070,589 A | 6/2000 | Keith et al. |
| 6,074,418 A | 6/2000 | Buchanan et al. |
| 6,077,214 A | 6/2000 | Mortier et al. |
| 6,077,297 A | 6/2000 | Robinson et al. |
| 6,086,582 A | 7/2000 | Altman et al. |
| 6,090,137 A | 7/2000 | Schmitt |
| 6,123,722 A | 9/2000 | Fogarty et al. |
| 6,126,685 A | 10/2000 | Lenker et al. |
| 6,129,685 A | 10/2000 | Howard |
| 6,145,509 A | 11/2000 | Tanner |
| 6,146,339 A | 11/2000 | Biagtan et al. |
| 6,152,144 A | 11/2000 | Lesh et al. |
| 6,162,168 A | 12/2000 | Schweich, Jr. et al. |
| 6,168,610 B1 | 1/2001 | Marin et al. |
| 6,174,323 B1 | 1/2001 | Biggs et al. |
| 6,179,809 B1 | 1/2001 | Khairkahan et al. |
| 6,197,049 B1 | 3/2001 | Shaolian et al. |
| 6,203,550 B1 | 3/2001 | Olson |
| 6,203,568 B1 | 3/2001 | Lombardi et al. |
| 6,206,827 B1 | 3/2001 | Chin et al. |
| 6,217,597 B1 | 4/2001 | Tanner |
| 6,224,540 B1 | 5/2001 | Lederman et al. |
| 6,231,561 B1 | 5/2001 | Frazier et al. |
| 6,248,118 B1 | 6/2001 | Tanner et al. |
| 6,250,974 B1 | 6/2001 | Kerek |
| 6,251,132 B1 | 6/2001 | Ravenscroft et al. |
| 6,258,021 B1 | 7/2001 | Wilk |
| 6,258,119 B1 | 7/2001 | Hussein et al. |
| 6,270,516 B1 | 8/2001 | Tanner et al. |
| 6,273,858 B1 | 8/2001 | Fox et al. |
| 6,286,514 B1 | 9/2001 | Lemelson |
| 6,287,315 B1 | 9/2001 | Wijeratne et al. |
| 6,287,335 B1 | 9/2001 | Drasler et al. |
| 6,293,906 B1 | 9/2001 | Vanden Hoek et al. |
| 6,296,656 B1 | 10/2001 | Bolduc et al. |
| 6,302,906 B1 | 10/2001 | Goicoechea et al. |
| 6,309,403 B1 | 10/2001 | Minor et al. |
| 6,319,278 B1 | 11/2001 | Quinn |
| 6,336,933 B1 | 1/2002 | Parodi |
| 6,343,605 B1 | 2/2002 | Lafontaine |
| 6,346,118 B1 | 2/2002 | Baker et al. |
| 6,352,561 B1 | 3/2002 | Leopold et al. |
| 6,361,556 B1 | 3/2002 | Chuter |
| 6,368,345 B1 | 4/2002 | Dehdashtian et al. |
| 6,371,919 B1 | 4/2002 | Tanner et al. |
| 6,398,803 B1 | 6/2002 | Layne et al. |
| 6,402,680 B2 | 6/2002 | Mortier et al. |
| 6,402,780 B2 | 6/2002 | Williamson, IV et al. |
| 6,406,420 B1 | 6/2002 | McCarthy et al. |
| 6,409,757 B1 | 6/2002 | Trout, III et al. |
| 6,416,365 B1 | 7/2002 | Iwahori |
| 6,416,522 B1 | 7/2002 | Strecker |
| 6,423,059 B1 | 7/2002 | Hanson et al. |
| 6,425,856 B1 | 7/2002 | Shapland et al. |
| 6,428,565 B1 | 8/2002 | Wisselink |
| 6,454,796 B1 | 9/2002 | Barkman et al. |
| 6,458,152 B1 | 10/2002 | Khosravi et al. |
| 6,461,365 B2 | 10/2002 | Bolduc et al. |
| 6,468,260 B1 | 10/2002 | Bumbalough et al. |
| 6,482,224 B1 | 11/2002 | Michler et al. |
| 6,520,974 B2 | 2/2003 | Tannerq et al. |
| 6,544,253 B1 | 4/2003 | Tanner |
| 6,558,425 B2 | 5/2003 | Rockwood, Jr. |
| 6,562,051 B1 | 5/2003 | Bolduc et al. |
| 6,565,597 B1 | 5/2003 | Fearnot et al. |
| 6,576,009 B2 | 6/2003 | Ryan et al. |
| 6,580,417 B2 | 6/2003 | Rosenberg et al. |
| 6,592,593 B1 | 7/2003 | Parodi et al. |
| 6,592,615 B1 | 7/2003 | Marcade et al. |
| 6,595,912 B2 | 7/2003 | Lau et al. |
| 6,607,555 B2 | 8/2003 | Patterson et al. |
| 6,616,684 B1 | 9/2003 | Vidlund et al. |
| 6,639,278 B2 | 10/2003 | Sumida et al. |
| 6,652,555 B1 | 11/2003 | Vantassel et al. |
| 6,652,572 B2 | 11/2003 | Kugler et al. |
| 6,663,558 B2 | 12/2003 | Lau et al. |
| 6,675,809 B2 | 1/2004 | Stack et al. |
| 6,685,620 B2 | 2/2004 | Gifford, III et al. |
| 6,702,763 B2 | 3/2004 | Murphy et al. |
| 6,702,844 B1 | 3/2004 | Lazarus |
| 6,709,442 B2 | 3/2004 | Miller et al. |
| 6,719,174 B1 | 4/2004 | Swift |
| 6,730,119 B1 | 5/2004 | Smalling et al. |
| 6,746,460 B2 | 6/2004 | Gannoe et al. |
| 6,800,081 B2 | 10/2004 | Parodi |
| 6,878,164 B2 | 4/2005 | Kujawski et al. |
| 6,929,661 B2 | 8/2005 | Bolduc et al. |
| 6,960,217 B2 | 11/2005 | Bolduc |
| 6,984,241 B2 | 1/2006 | Lubbers et al. |
| 6,986,775 B2 | 1/2006 | Morales et al. |
| 6,986,784 B1 | 1/2006 | Weiser et al. |
| 7,033,384 B2 | 4/2006 | Gannoe et al. |
| 7,037,343 B2 | 5/2006 | Imran |
| 7,060,021 B1 | 6/2006 | Wilk |
| 7,060,023 B2 | 6/2006 | French et al. |
| 7,081,086 B2 | 7/2006 | Lau et al. |
| 7,081,129 B2 | 7/2006 | Chobotov |
| 7,128,754 B2 | 10/2006 | Bolduc |
| 7,147,657 B2 | 12/2006 | Chiang et al. |
| 7,155,295 B2 | 12/2006 | Lau et al. |
| 7,179,225 B2 | 2/2007 | Shluzas et al. |
| 7,306,623 B2 | 12/2007 | Watson |
| 7,335,213 B1 | 2/2008 | Hyde et al. |
| 7,361,137 B2 | 4/2008 | Taylor et al. |
| 7,404,824 B1 | 7/2008 | Webler et al. |
| 7,422,558 B2 | 9/2008 | Lau et al. |
| 7,491,232 B2 | 2/2009 | Bolduc et al. |
| 7,544,198 B2 | 6/2009 | Parodi |
| 7,563,267 B2 | 7/2009 | Goldfarb et al. |
| 7,591,842 B2 | 9/2009 | Parodi |
| 7,637,932 B2 | 12/2009 | Bolduc et al. |
| 7,670,362 B2 * | 3/2010 | Zergiebel ............ A61B 17/064 606/311 |
| 7,704,269 B2 | 4/2010 | St. Goar et al. |
| 7,727,189 B2 | 6/2010 | Vantassel et al. |
| 7,753,922 B2 | 7/2010 | Starksen |
| 7,811,295 B2 | 10/2010 | Kortenbach |
| 7,823,267 B2 | 11/2010 | Bolduc et al. |
| 7,828,267 B2 | 11/2010 | Iwabuchi et al. |
| 7,828,838 B2 | 11/2010 | Bolduc et al. |
| 7,959,663 B2 | 6/2011 | Bolduc |
| 7,959,670 B2 | 6/2011 | Bolduc |
| 8,075,570 B2 | 12/2011 | Bolduc et al. |
| 8,080,050 B2 | 12/2011 | Chiang et al. |
| 8,083,752 B2 | 12/2011 | Bolduc |
| 8,092,519 B2 | 1/2012 | Bolduc |
| 8,231,639 B2 | 7/2012 | Bolduc et al. |
| 8,685,044 B2 | 4/2014 | Bolduc et al. |
| 8,690,897 B2 | 4/2014 | Bolduc |
| 9,023,065 B2 | 5/2015 | Bolduc et al. |
| 2001/0041821 A1 | 11/2001 | Wilk |
| 2001/0047199 A1 | 11/2001 | Wijay |
| 2002/0026144 A1 | 2/2002 | Patterson |
| 2002/0029077 A1 | 3/2002 | Leopold et al. |
| 2002/0058855 A1 | 5/2002 | Cyril, Jr. et al. |
| 2002/0065485 A1 | 5/2002 | DuBois |
| 2002/0087169 A1 | 7/2002 | Brock et al. |
| 2002/0087170 A1 * | 7/2002 | Kuhns ................. A61B 17/064 606/143 |
| 2002/0099432 A1 | 7/2002 | Yee |
| 2002/0133054 A1 | 9/2002 | Murphy et al. |

(56) References Cited

U.S. PATENT DOCUMENTS

| | | |
|---|---|---|
| 2002/0156365 A1 | 10/2002 | Tsekos |
| 2002/0156521 A1 | 10/2002 | Ryan et al. |
| 2002/0183827 A1 | 12/2002 | Derus et al. |
| 2003/0004560 A1 | 1/2003 | Chobotov et al. |
| 2003/0009441 A1* | 1/2003 | Holsten ............... A61B 17/068 |
| 2003/0018358 A1 | 1/2003 | Saadat |
| 2003/0023248 A1* | 1/2003 | Parodi ............... A61B 17/064 |
| | | 606/139 |
| 2003/0060674 A1 | 3/2003 | Hanson, III et al. |
| 2003/0078465 A1 | 4/2003 | Pai et al. |
| 2003/0100943 A1* | 5/2003 | Bolduc ............... A61B 17/064 |
| | | 623/1.35 |
| 2003/0105384 A1 | 6/2003 | Sharkey et al. |
| 2003/0105519 A1 | 6/2003 | Fasol et al. |
| 2003/0130731 A1 | 7/2003 | Vidlund et al. |
| 2003/0149463 A1 | 8/2003 | Solymar et al. |
| 2003/0158570 A1 | 8/2003 | Ferrazzi |
| 2003/0163085 A1 | 8/2003 | Tanner et al. |
| 2003/0204249 A1 | 10/2003 | Letort |
| 2003/0233140 A1 | 12/2003 | Hartley et al. |
| 2004/0002731 A1 | 1/2004 | Aganon et al. |
| 2004/0039405 A1 | 2/2004 | Petrovic et al. |
| 2004/0044364 A1 | 3/2004 | Devries et al. |
| 2004/0049207 A1 | 3/2004 | Goldfarb et al. |
| 2004/0054352 A1 | 3/2004 | Adams et al. |
| 2004/0093057 A1 | 5/2004 | Bolduc et al. |
| 2004/0127916 A1* | 7/2004 | Bolduc ............... A61B 17/064 |
| | | 606/151 |
| 2004/0138734 A1 | 7/2004 | Chobotov et al. |
| 2004/0153143 A1 | 8/2004 | Quiachon et al. |
| 2004/0186566 A1 | 9/2004 | Hindrichs et al. |
| 2004/0206363 A1 | 10/2004 | McCarthy et al. |
| 2004/0210304 A1 | 10/2004 | Seguin et al. |
| 2004/0243170 A1 | 12/2004 | Suresh et al. |
| 2004/0254594 A1 | 12/2004 | Alfaro |
| 2004/0260322 A1 | 12/2004 | Rudko et al. |
| 2004/0260383 A1 | 12/2004 | Stelter et al. |
| 2005/0038506 A1 | 2/2005 | Webler et al. |
| 2005/0043790 A1 | 2/2005 | Seguin |
| 2005/0070992 A1 | 3/2005 | Bolduc et al. |
| 2005/0113906 A9 | 5/2005 | Bolduc et al. |
| 2005/0154401 A1 | 7/2005 | Weldon et al. |
| 2005/0177180 A1 | 8/2005 | Kaganov et al. |
| 2005/0187568 A1* | 8/2005 | Klenk ............... A61B 17/0057 |
| | | 606/153 |
| 2005/0187613 A1 | 8/2005 | Bolduc et al. |
| 2005/0197716 A1 | 9/2005 | Sharkey et al. |
| 2005/0215874 A1 | 9/2005 | Wang et al. |
| 2005/0240258 A1 | 10/2005 | Bolduc et al. |
| 2005/0240260 A1 | 10/2005 | Bolduc |
| 2006/0100640 A1 | 5/2006 | Bolduc |
| 2006/0111692 A1 | 5/2006 | Hlavka et al. |
| 2006/0184224 A1 | 8/2006 | Angel |
| 2006/0253186 A1 | 11/2006 | Bates |
| 2006/0259125 A1 | 11/2006 | Peacock, III |
| 2006/0287661 A1 | 12/2006 | Bolduc et al. |
| 2007/0021753 A1 | 1/2007 | Bolduc et al. |
| 2007/0021829 A1 | 1/2007 | Bolduc et al. |
| 2007/0032860 A1 | 2/2007 | Brooks et al. |
| 2007/0073389 A1 | 3/2007 | Bolduc et al. |
| 2007/0083255 A1 | 4/2007 | Chiang et al. |
| 2008/0065115 A1 | 3/2008 | Parodi |
| 2008/0065117 A1 | 3/2008 | Bolduc et al. |
| 2008/0065189 A1 | 3/2008 | Bolduc |
| 2008/0065191 A1 | 3/2008 | Bolduc et al. |
| 2008/0097489 A1 | 4/2008 | Goldfarb et al. |
| 2008/0132996 A1 | 6/2008 | Drasler et al. |
| 2009/0082852 A1 | 3/2009 | Bolduc et al. |
| 2009/0099650 A1 | 4/2009 | Bolduc et al. |
| 2009/0112302 A1 | 4/2009 | Stafford |
| 2009/0112303 A1 | 4/2009 | Bolduc |
| 2009/0138072 A1 | 5/2009 | Gendreau |
| 2010/0094400 A1 | 4/2010 | Bolduc et al. |
| 2011/0087320 A1 | 4/2011 | Bolduc et al. |
| 2011/0238088 A1 | 9/2011 | Bolduc et al. |
| 2011/0276062 A1 | 11/2011 | Bolduc |
| 2012/0059450 A1 | 3/2012 | Chiang et al. |
| 2012/0065661 A1 | 3/2012 | Bolduc |
| 2012/0316578 A1 | 12/2012 | Bolduc et al. |
| 2014/0214051 A1 | 7/2014 | Bolduc |
| 2015/0127015 A1 | 5/2015 | Bolduc et al. |

FOREIGN PATENT DOCUMENTS

| | | |
|---|---|---|
| AU | 2005235108 A1 | 11/2005 |
| AU | 2008243229 A1 | 12/2008 |
| AU | 2004287355 B2 | 6/2011 |
| AU | 2006305688 B2 | 12/2012 |
| AU | 2011253682 B9 | 1/2014 |
| AU | 2011224089 B2 | 7/2014 |
| CA | 2265131 A1 | 9/1999 |
| CA | 2344252 A1 | 3/2000 |
| CA | 2729464 A1 | 6/2003 |
| CA | 2539265 A1 | 5/2005 |
| CA | 2626505 A1 | 4/2007 |
| CA | 2626106 A1 | 5/2007 |
| CA | 2625082 A1 | 7/2008 |
| CA | 2740831 A1 | 4/2010 |
| CA | 2464048 A1 | 6/2010 |
| CA | 2464900 A1 | 4/2011 |
| CA | 2554022 A1 | 11/2012 |
| CA | 2546721 C | 9/2013 |
| CN | 1019461 B | 12/1992 |
| CN | 1422139 A | 6/2003 |
| CN | 1596087 A | 3/2005 |
| CN | 1596088 A | 3/2005 |
| CN | 1856280 A | 11/2006 |
| CN | 1870949 A | 11/2006 |
| CN | 1870951 A | 11/2006 |
| CN | 1997318 A | 7/2007 |
| CN | 101151002 A | 3/2008 |
| CN | 101267788 A | 9/2008 |
| CN | 101330882 A | 12/2008 |
| CN | 101352375 A | 1/2009 |
| CN | 101360466 A | 2/2009 |
| CN | 101460104 A | 6/2009 |
| CN | 101466316 A | 6/2009 |
| CN | 100525719 C | 8/2009 |
| CN | 101330882 B | 4/2011 |
| CN | 101466316 B | 6/2012 |
| DE | 3333427 C2 | 5/1991 |
| DE | 69228184 T2 | 9/1999 |
| DE | 10034105 C1 | 4/2002 |
| DE | 10297483 T5 | 12/2004 |
| EP | 321912 A1 | 6/1989 |
| EP | 0663184 A1 | 7/1995 |
| EP | 0835642 B1 | 2/2002 |
| EP | 1369098 A1 | 12/2003 |
| EP | 1440673 A1 | 7/2004 |
| EP | 1448117 A1 | 8/2004 |
| EP | 1675528 A2 | 7/2006 |
| EP | 1725172 A2 | 11/2006 |
| EP | 1734872 A1 | 12/2006 |
| EP | 1948080 A2 | 7/2008 |
| EP | 2119416 A1 | 11/2009 |
| EP | 2349086 A1 | 8/2011 |
| EP | 2349087 A1 | 8/2011 |
| FR | 2299548A 1 | 8/1976 |
| FR | 2865926 A1 | 8/2005 |
| GB | 2396824 A | 7/2004 |
| GB | 2417208 A | 2/2006 |
| HK | 1073240 A1 | 8/2009 |
| JP | 2001509398 A | 7/2001 |
| JP | 2001522292 A | 11/2001 |
| JP | 2001526574 A | 12/2001 |
| JP | 2002526193 A | 8/2002 |
| JP | 2005046648 A | 2/2005 |
| JP | 2005510293 A | 4/2005 |
| JP | 2005510303 A | 4/2005 |
| JP | 2007508894 A | 4/2007 |
| JP | 2007508895 A | 4/2007 |
| JP | 2007523694 A | 8/2007 |
| JP | 2007535339 A | 12/2007 |
| JP | 2009512497 A | 3/2009 |

(56) References Cited

FOREIGN PATENT DOCUMENTS

| | | | |
|---|---|---|---|
| JP | 2009512498 A | 3/2009 | |
| JP | 2009512499 A | 3/2009 | |
| JP | 2009078172 A | 4/2009 | |
| JP | 2009095684 A | 5/2009 | |
| JP | 2009106763 A | 5/2009 | |
| JP | 2009106768 A | 5/2009 | |
| JP | 2009106775 A | 5/2009 | |
| JP | 2009112827 A | 5/2009 | |
| JP | 2009519046 A | 5/2009 | |
| JP | 4405262 B2 | 1/2010 | |
| JP | 10506026 A | 2/2010 | |
| JP | 2010051786 A | 3/2010 | |
| JP | 4465359 B2 | 5/2010 | |
| JP | 2011062570 A | 3/2011 | |
| JP | 4699445 B2 | 6/2011 | |
| WO | WO-9300868 A1 | 1/1993 | |
| WO | WO-9521592 A1 | 8/1995 | |
| WO | WO-9603925 A1 | 2/1996 | |
| WO | WO-9703616 A1 | 2/1997 | |
| WO | WO-1997003616 A1 | 2/1997 | |
| WO | WO-9712562 A1 | 4/1997 | |
| WO | WO-9717039 A1 | 5/1997 | |
| WO | WO-9717913 A1 | 5/1997 | |
| WO | WO-9811814 A2 | 3/1998 | |
| WO | WO-9853761 A1 | 12/1998 | |
| WO | WO-9930637 A1 | 6/1999 | |
| WO | WO-9933402A 1 | 7/1999 | |
| WO | WO-9933402 A9 | 9/1999 | |
| WO | WO-9953845 A1 | 10/1999 | |
| WO | WO-1999053845 A1 | 10/1999 | |
| WO | WO-0064357 A1 | 1/2000 | |
| WO | WO-0016701 A1 | 3/2000 | |
| WO | WO-0035350 A1 | 6/2000 | |
| WO | WO-0160432 A1 | 8/2001 | |
| WO | WO-03032870 A1 | 4/2003 | |
| WO | WO-03045283 A1 | 6/2003 | |
| WO | WO-03045467 A2 | 6/2003 | |
| WO | WO-03045467 A3 | 7/2003 | |
| WO | WO-03079935 A1 | 10/2003 | |
| WO | WO-2004008975 A1 | 1/2004 | |
| WO | WO-2004021872 A2 | 3/2004 | |
| WO | WO-2005032333 A2 | 4/2005 | |
| WO | WO-2005037076 A2 | 4/2005 | |
| WO | WO-2005044073 A2 | 5/2005 | |
| WO | WO-2005044147 A1 | 5/2005 | |
| WO | WO-2005044148 A1 | 5/2005 | |
| WO | WO-2005067660 A2 | 7/2005 | |
| WO | WO-2005081936 A2 | 9/2005 | |
| WO | WO-2007046955 A3 | 10/2005 | |
| WO | WO-2005102181 A1 | 11/2005 | |
| WO | WO-2005032333 A3 | 4/2006 | |
| WO | WO-2005067660 A3 | 4/2007 | |
| WO | WO-2007046953 A2 | 4/2007 | |
| WO | WO-2007046954 A2 | 4/2007 | |
| WO | WO-2007046955 A2 | 4/2007 | |
| WO | WO-2007047023 A2 | 4/2007 | |
| WO | WO-2007053233 A2 | 5/2007 | |
| WO | WO-2007046953 A3 | 6/2007 | |
| WO | WO-2007047023 A3 | 10/2007 | |
| WO | WO-2005081936 A3 | 11/2007 | |
| WO | WO-2007053233 A3 | 1/2008 | |
| WO | WO-2007046954 A3 | 11/2008 | |
| WO | WO-2005044073 A3 | 3/2009 | |
| WO | WO-2010004856 A1 | 1/2010 | |
| WO | WO-2010044851 A1 | 4/2010 | |
| WO | WO-2010044854A 1 | 4/2010 | |
| WO | WO-2010044855 A1 | 4/2010 | |
| WO | WO-2010044856 A1 | 4/2010 | |

OTHER PUBLICATIONS

"U.S. Appl. No. 10/099,149, Non Final Office Action dated Sep. 10, 2003", 6 pgs.

"U.S. Appl. No. 10/099,149, Response filed Mar. 12, 2004 to Non Final Office Action dated Sep. 10, 2003", 5 pgs.

"U.S. Appl. No. 10/099,149, Notice of Allowance dated Jun. 24, 2004", 4 pgs.

"U.S. Appl. No. 10/271,334, Response filed Mar. 15, 2004 to Restriction Requirement dated Sep. 23, 2003", 1 pg.

"U.S. Appl. No. 10/271,334, Restriction Requirement dated Sep. 23, 2003", 4 pgs.

"U.S. Appl. No. 10/271,334, Non Final Office Action dated May 18, 2004", 9 pgs.

"U.S. Appl. No. 10/271,334, Response filed Nov. 22, 2004 to Non Final Office Action dated May 18, 2004", 6 pgs.

"U.S. Appl. No. 10/271,334, Supplemental Response filed Jan. 28, 2005 to Non Final Office Action dated May 18, 2004" 6 pgs.

"U.S. Appl. No. 10/271,334, Examiner Interview Summary dated Feb. 11, 2005", 2 pgs.

"U.S. Appl. No. 10/271,334, Notice of Allowance dated Feb. 11, 2005", 6 pgs.

"U.S. Appl. No. 10/271,334, Notice of Allowance dated Mar. 17, 2005", 3 pgs.

"U.S. Appl. No. 10/271,334, Notice of Allowance dated Aug. 26, 2005", 3 pgs.

"U.S. Appl. No. 10/307,226, Preliminary Amendment filed Jul. 22, 2005", 3 pgs.

"U.S. Appl. No. 10/307,226, Non Final Office Action dated Mar. 13, 2006", 6 pgs.

"U.S. Appl. No. 10/307,226, Response filed Sep. 15, 2006 to Non Final Office Action dated Mar. 13, 2006", 6 pgs.

"U.S. Appl. No. 10/307,226, Final Office Action dated Dec. 12, 2006", 5 pgs.

"U.S. Appl. No. 10/307,226, Response filed Apr. 9, 2007 to Final Office Action dated Dec. 12, 2006", 7 pgs.

"U.S. Appl. No. 10/307,226, Non Final Office Action dated Jun. 12, 2007", 5 pgs.

"U.S. Appl. No. 10/307,226, Response filed Dec. 14, 2007 to Non Final Office Action dated Jun. 12, 2007", 7 pgs.

"U.S. Appl. No. 10/307,226, Final Office Action dated Jun. 27, 2008", 6 pgs.

"U.S. Appl. No. 10/307,226, Response filed Jun. 23, 2009 to Final Office Action dated Jun. 27, 2008", 10 pgs.

"U.S. Appl. No. 10/307,226, Non Final Office Action dated Sep. 9, 2009", 16 pgs.

"U.S. Appl. No. 10/307,226, Appeal Brief filed Oct. 14, 2010", 15 pgs.

"U.S. Appl. No. 10/307,226, Notice of Allowance dated Jul. 22, 2011", 8 pgs.

"U.S. Appl. No. 10/307,226, 312 Amendment filed Oct. 24, 2011", 3 pgs.

"U.S. Appl. No. 10/307,226, PTO Response to 312 Amendment dated Nov. 10, 2011", 3 pgs.

"U.S. Appl. No. 10/669,881, Preliminary Amendment dated May 6, 2005", 3 pgs.

"U.S. Appl. No. 10/669,881, Non Final Office Action dated Jan. 27, 2006", 5 pgs.

"U.S. Appl. No. 10/669,881, Response filed May 15, 2006 to Non Final Office Action dated Jan. 27, 2006", 9 pgs.

"U.S. Appl. No. 10/669,881, Restriction Requirement dated Jan. 27, 2006", 5 pgs.

"U.S. Appl. No. 10/669,881, Response filed Oct. 2, 2006 to Restriction Requirement dated Jul. 27, 2006", 6 pgs.

"U.S. Appl. No. 10/669,881, Restriction Requirement dated Jun. 19, 2007", 5 pgs.

"U.S. Appl. No. 10/669,881, Response filed Sep. 7, 2007 to Restriction Requirement dated Jun. 19, 2007", 4 pgs.

"U.S. Appl. No. 10/669,881, Final Office Action dated Jan. 25, 2008", 7 pgs.

"U.S. Appl. No. 10/669,881, Response filed Mar. 11, 2008 to Final Office Action dated Jan. 25, 2008", 8 pgs.

"U.S. Appl. No. 10/669,881, Notice of Allowance dated Oct. 8, 2008", 16 pgs.

"U.S. Appl. No. 10/692,282, Restriction Requirement dated Aug. 17, 2004", 6 pgs.

"U.S. Appl. No. 10/692,282, Response filed Feb. 22, 2005 to Restriction Requirement dated Aug. 17, 2004", 4 pgs.

(56) References Cited

OTHER PUBLICATIONS

"U.S. Appl. No. 10/692,282, Non Final Office Action dated Aug. 30, 2005", 6 pgs.
"U.S. Appl. No. 10/692,282, Response filed Feb. 28, 2006 to Non Final Office Action dated Aug. 30, 2005", 5 pgs.
"U.S. Appl. No. 10/692,282, Notice of Allowance dated Jun. 13, 2006", 6 pgs.
"U.S. Appl. No. 10/692,283, Preliminary Amendment filed Nov. 22, 2004", 3 pgs.
"U.S. Appl. No. 10/692,283, Non Final Office Action dated Nov. 16, 2005", 6 pgs.
"U.S. Appl. No. 10/692,283, Response filed May 19, 2006 to Non Final Office Action dated Nov. 16, 2005", 5 pgs.
"U.S. Appl. No. 10/692,283, Notice of Allowance dated Aug. 1, 2006", 4 pgs.
"U.S. Appl. No. 10/693,255, Non Final Office Action date Dec. 9, 2004", 6 pgs.
"U.S. Appl. No. 10/693,255, Examiner Interview Summary dated Feb. 17, 2005", 3 pgs.
"U.S. Appl. No. 10/693,255, Response filed Feb. 17, 2005 to Non Final Office Action dated Dec. 9, 2004", 6 pgs.
"U.S. Appl. No. 10/693,255, Notice of Allowance dated Mar. 9, 2005", 9 pgs.
"U.S. Appl. No. 10/752,435, Non Final Office Action dated Oct. 19, 2006", 17 pgs.
"U.S. Appl. No. 10/752,435, Response filed Apr. 9, 2007 to Non Final Office Action dated Oct. 19, 2006", 13 pgs.
"U.S. Appl. No. 10/752,435, Final Office Action dated Jul. 12, 2007", 8 pgs.
"U.S. Appl. No. 10/752,435, Response filed Jan. 9, 2008 to Final Office Action dated Jul. 12, 2007", 10 pgs.
"U.S. Appl. No. 10/752,435, Non Final Office Action dated Mar. 18, 2008", 7 pgs.
"Application U.S. Appl. No. 10/752,435, Response filed Sep. 19, 2008 to Non Final Office Action dated Mar. 18, 2008", 7 pgs.
"U.S. Appl. No. 10/752,435, Final Office Action dated Dec. 8, 2008", 8 pgs.
"U.S. Appl. No. 10/752,435, Response filed May 12, 2009 to Final Office Action dated Dec. 8, 2008", 9 pgs.
"U.S. Appl. No. 10/752,435, Non Final Office Action dated Jul. 21, 2009", 7 pgs.
"U.S. Appl. No. 10/752,435, Response filed Jan. 25, 2010 to Non Final Office Action dated Jul. 21, 2009", 9 pgs.
"U.S. Appl. No. 10/752,435, Final Office Action dated May 14, 2010", 8 pgs.
"U.S. Appl. No. 10/786,465, Preliminary Amendment filed May 16, 2005", 3 pgs.
"U.S. Appl. No. 10/786,465, Restriction Requirement dated Dec. 8, 2006", 6 pgs.
"U.S. Appl. No. 10/786,465, Response filed Apr. 9, 2007 to Restriction Requirement dated Dec. 8, 2006", 4 pgs.
"U.S. Appl. No. 10/786,465, Non Final Office Action dated Jul. 23, 2007", 7 pgs.
"U.S. Appl. No. 10/786,465, Response filed Jan. 25, 2008 to Non Final Office Action dated Jul. 23, 2007", 8 pgs.
"U.S. Appl. No. 10/786,465, Examiner Interview Summary dated Mar. 3, 2008", 2 pgs.
"U.S. Appl. No. 10/786,465, Supplemental Amendment filed Mar. 18, 2008", 8 pgs.
"U.S. Appl. No. 10/786,465, Restriction Requirement dated Jul. 24, 2008", 5 pgs.
"U.S. Appl. No. 10/786,465, Response filed Sep. 19, 2008 to Restriction Requirement dated Jul. 24, 2008", 4 pgs.
"U.S. Appl. No. 10/786,465, Final Office Action dated Jan. 21, 2009", 8 pgs.
"U.S. Appl. No. 10/786,465, Response filed Jul. 22, 2009 to Final Office Action dated Jan. 21, 2009", 5 pgs.
"U.S. Appl. No. 10/786,465, Non Final Office Action dated Mar. 26, 2010", 8 pgs.
"U.S. Appl. No. 10/786,465, Examiner Interview Summary dated Apr. 26, 2011", 3 pgs.
"U.S. Appl. No. 10/786,465, Response filed Apr. 26, 2011 to Non Final Office Action dated Mar. 26, 2010", 14 pgs.
"U.S. Appl. No. 10/786,465, Notice of Allowance dated Mar. 14, 2012", 11 pgs.
"U.S. Appl. No. 10/786,465, Supplemental Notice of Allowability dated May 8, 2012", 6 pgs.
"U.S. Appl. No. 10/786,465, Applicant's Summary of Examiner Interview filed Jun. 6, 2012", 2 pgs.
"U.S. Appl. No. 10/786,465, Corrected Notice of Allowability dated Jul. 2, 2012", 4 pgs.
"U.S. Appl. No. 10/808,216, Preliminary Amendment filed Jun. 15, 2005", 3 pgs.
"U.S. Appl. No. 11/166,411, Preliminary Amendment filed Oct. 2, 2006", 5 pgs.
"U.S. Appl. No. 11/166,411, Supplemental Preliminary Amendment filed Oct. 30, 2007", 7 pgs.
"U.S. Appl. No. 11/166,411, Restriction Requirement dated Jul. 15, 2008", 5 pgs.
"U.S. Appl. No. 11/166,411, Response filed Jan. 12, 2009 to Restriction Requirement dated Jul. 15, 2008", 5 pgs.
"U.S. Appl. No. 11/166,411, Non Final Office Action dated May 5, 2009", 8 pgs.
"U.S. Appl. No. 11/166,411, Response filed Nov. 9, 2009 to Non Final Office Action dated May 5, 2009", 8 pgs.
"U.S. Appl. No. 11/166,411, Final Office Action dated Dec. 3, 2009", 5 pgs.
"U.S. Appl. No. 11/166,411, Response filed Jun. 7, 2010 to Final Office Action dated Dec. 3, 2009", 5 pgs.
"U.S. Appl. No. 11/166,411, Notice of Allowance dated Jan. 6, 2011", 4 pgs.
"U.S. Appl. No. 11/166,411, Notice of Allowance dated Aug. 23, 2011", 5 pgs.
"U.S. Appl. No. 11/166,411, 312 Amendment filed Nov. 23, 2011", 3 pgs.
"U.S. Appl. No. 11/166,411, PTO Response to 312 Amendment dated Dec. 13, 2011", 2 pgs.
"U.S. Appl. No. 11/166,428, Non Final Office Action dated May 14, 2008", 6 pgs.
"U.S. Appl. No. 11/166,428, Response filed Nov. 17, 2008 to Non Final Office Action dated May 14, 2008", 6 pgs.
"U.S. Appl. No. 11/166,428, Final Office Action dated Jan. 12, 2009", 10 pgs.
"U.S. Appl. No. 11/166,428, Response filed May 12, 2009 to Final Office Action dated Jan. 12, 2009", 6 pgs.
"U.S. Appl. No. 11/166,428, Non Final Office Action dated Jun. 16, 2009", 10 pgs.
"U.S. Appl. No. 11/166,428, Response filed Dec. 22, 2009 to Non Final Office Action dated Dec. 16, 2009", 8 pgs.
"U.S. Appl. No. 11/166,428, Final Office Action dated Mar. 16, 2010", 8 pgs.
"U.S. Appl. No. 11/254,444, Preliminary Amendment filed Oct. 20, 2005", 8 pgs.
"U.S. Appl. No. 11/254,444, Preliminary Amendment filed Nov. 15, 2005", 8 pgs.
"U.S. Appl. No. 11/254,444, Restriction Requirement dated Jun. 19, 2009", 6 pgs.
"U.S. Appl. No. 11/254,444, Response filed Dec. 18, 2009 to Restriction Requirement dated Jun. 19, 2009", 2 pgs.
"U.S. Appl. No. 11/254,444, Notice of Allowance dated Mar. 9, 2010", 7 pgs.
"U.S. Appl. No. 11/254,444, Notice of Allowance dated Apr. 5, 2010", 4 pgs.
"U.S. Appl. No. 11/254,444, Notice of Allowance dated Jun. 29, 2010", 6 pgs.
"U.S. Appl. No. 11/254,619, Response filed Apr. 20, 2012 to Final Office Action dated Oct. 20, 2011", 11 pgs.
"U.S. Appl. No. 11/254,619, Non Final Office Action dated Oct. 1, 2009", 5 pgs.
"U.S. Appl. No. 11/254,619, Non Final Office Action dated Oct. 1, 2009", 6 pgs.

(56) References Cited

OTHER PUBLICATIONS

"U.S. Appl. No. 11/254,619, Final Office Action dated Jun. 30, 2010", 10 pgs.
"U.S. Appl. No. 11/254,619, Final Office Action dated Jun. 30, 2010", 11 pgs.
"U.S. Appl. No. 11/254,619, Response filed Dec. 29, 2010 to Final Office Action dated Jun. 30, 2010", 12 pgs.
"U.S. Appl. No. 11/254,619, Non Final Office Action dated Feb. 3, 2011", 8 pgs.
"U.S. Appl. No. 11/254,619, Non Final Office Action dated Feb. 3, 2011", 9 pgs.
"U.S. Appl. No. 11/254,619, Response filed Aug. 3, 2011 to Non Final Office Action dated Feb. 3, 2011", 13 pgs.
"U.S. Appl. No. 11/254,619, Final Office Action dated Oct. 20, 2011", 11 pgs.
"U.S. Appl. No. 11/254,619, Final Office Action dated Oct. 20, 2011", 12 pgs.
"U.S. Appl. No. 11/254,619, Response filed May 6, 2014 to Non Final Office Action dated Jan. 6, 2014", 10 pgs.
"U.S. Appl. No. 11/254,619, Final Office Action dated Jun. 19, 2014", 17 pgs.
"U.S. Appl. No. 11/254,619, Response filed Sep. 15, 2014 to Final Office Action dated Jun. 19, 2014", 12 pgs.
"U.S. Appl. No. 11/254,619, Examiner Interview Summary dated Sep. 18, 2014", 3 pgs.
"U.S. Appl. No. 11/254,619, Advisory Action dated Sep. 24, 2014", 3 pgs.
"U.S. Appl. No. 11/254,619, Non Final Office Action dated Jan. 6, 2014", 19 pgs.
"U.S. Appl. No. 11/254,619, Response filed Apr. 1, 2010 to Non Final Office Action dated Oct. 1, 2009", 5 pgs.
"U.S. Appl. No. 11/254,950, Preliminary Amendment filed Nov. 18, 2005", 4 pgs.
"U.S. Appl. No. 11/254,950, Restriction Requirement dated Jul. 9, 2008", 9 pgs.
"U.S. Appl. No. 11/254,950, Response filed Jan. 5, 2009 to Restriction Requirement dated Jul. 9, 2008", 7 pgs.
"U.S. Appl. No. 11/254,950, Non Final Office Action dated Mar. 30, 2009", 6 pgs.
"U.S. Appl. No. 11/254,950, Response filed Oct. 5, 2009 to Non Final Office Action dated Mar. 30, 2009", 5 pgs.
"U.S. Appl. No. 11/254,950, Notice of Allowance dated Feb. 26, 2010", 4 pgs.
"U.S. Appl. No. 11/254,950, Notice of Allowance dated Jun. 22, 2010", 4 pgs.
"U.S. Appl. No. 11/255,116, Preliminary Amendment filed Nov. 18, 2005", 4 pgs.
"U.S. Appl. No. 11/255,116, Non Final Office Action dated May 14, 2008", 15 pgs.
"U.S. Appl. No. 11/255,116, Response filed Nov. 17, 2008 to Non Final Office Action dated May 24, 2008", 7 pgs.
"U.S. Appl. No. 11/255,116, Restriction Requirement dated Mar. 18, 2009", 7 pgs.
"U.S. Appl. No. 11/255,116, Response filed May 20, 2009 to Restriction Requirement dated Mar. 18, 2009", 4 pgs.
"U.S. Appl. No. 11/255,116, Notice of Allowance dated Aug. 10, 2009", 4 pgs.
"U.S. Appl. No. 11/365,056, Restriction Requirement dated Jun. 10, 2009", 5 pgs.
"U.S. Appl. No. 11/365,056, Response filed Dec. 10, 2009 to Restriction Requirement dated Jun. 10, 2009", 44 pgs.
"U.S. Appl. No. 11/365,056, Non Final Office Action dated Mar. 23, 2010", 11 pgs.
"U.S. Appl. No. 11/365,056, Response filed Sep. 28, 2010 to Non Final Office Action dated Mar. 23, 2010", 5 pgs.
"U.S. Appl. No. 11/365,056, Final Office Action dated Dec. 9, 2010", 13 pgs.
"U.S. Appl. No. 11/488,305, Restriction Requirement dated Jan. 5, 2010", 6 pgs.
"U.S. Appl. No. 11/488,305, Response filed Jul. 2, 2010 to Restriction Requirement dated Jan. 5, 2010", 8 pgs.
"U.S. Appl. No. 11/488,305, Non Final Office Action dated Sep. 1, 2010", 8 pgs.
"U.S. Appl. No. 11/488,305, Response filed Feb. 1, 2011 to Non Final Office Action dated Sep. 1, 2010", 12 pgs.
"U.S. Appl. No. 11/488,305, Final Office Action dated Apr. 13, 2011", 9 pgs.
"U.S. Appl. No. 11/488,305, Response filed Oct. 13, 2011 to Final Office Action dated Apr. 13, 2011", 11 pgs.
"U.S. Appl. No. 11/488,305, Non Final Office Action dated Oct. 31, 2011", 6 pgs.
"U.S. Appl. No. 11/488,305, Response filed Apr. 26, 2012 to Non Final Office Action dated Oct. 31, 2011", 12 pgs.
"U.S. Appl. No. 11/488,305, Non Final Office Action dated Sep. 14, 2012", 9 pgs.
"U.S. Appl. No. 11/488,305, Response filed Feb. 13, 2013 to Non Final Office Action dated Sep. 14, 2012", 10 pgs.
"U.S. Appl. No. 11/488,305, Final Office Action dated Mar. 6, 2013", 9 pgs.
"U.S. Appl. No. 11/488,305, Response filed May 3, 2013 to Final Office Action dated Mar. 6, 2013", 11 pgs.
"U.S. Appl. No. 11/488,305, Advisory Action dated Jun. 7, 2013", 3 pgs.
"U.S. Appl. No. 11/488,305, Non Final Office Action dated Jan. 29, 2014", 10 pgs.
"U.S. Appl. No. 11/488,305, Response filed Apr. 29, 2014 to Non Final Office Action dated Jan. 29, 2014", 9 pgs.
"U.S. Appl. No. 11/488,305, Final Office Action dated Aug. 14, 2014", 11 pgs.
"U.S. Appl. No. 11/540,427, Preliminary Amendment filed Oct. 3, 2007", 5 pgs.
"U.S. Appl. No. 11/540,427, Non Final Office Action dated Oct. 6, 2008", 10 pgs.
"U.S. Appl. No. 11/540,427, Response filed Apr. 10, 2009 to Non Final Office Action dated Oct. 6, 2008", 6 pgs.
"U.S. Appl. No. 11/540,427, Final Office Action dated Jul. 21, 2009", 9 pgs.
"U.S. Appl. No. 11/540,427, Appeal Brief filed Aug. 26, 2010", 26 pgs.
"U.S. Appl. No. 11/540,427, Notice of Allowance dated Apr. 11, 2011", 8 pgs.
"U.S. Appl. No. 11/540,427, Notice of Allowance dated Apr. 29, 2011", 8 pgs.
"U.S. Appl. No. 11/540,428, Restriction Requirement dated Mar. 29, 2010", 9 pgs.
"U.S. Appl. No. 11/540,428, Response filed Oct. 1, 2010 to Restriction Requirement dated Mar. 29, 2010", 6 pgs.
"U.S. Appl. No. 11/540,428, Non Final Office Action dated Nov. 12, 2010", 8 pgs.
"U.S. Appl. No. 11/540,428, Response filed May 12, 2011 to Non Final Office Action dated Nov. 12, 2010", 12 pgs.
"U.S. Appl. No. 11/540,428, Final Office Action dated Aug. 4, 2011", 9 pgs.
"U.S. Appl. No. 11/580,584, Non Final Office Action dated Apr. 18, 2008", 6 pgs.
"U.S. Appl. No. 11/580,584, Response filed Oct. 20, 2008 to Non Final Office Action dated Apr. 18, 2008", 5 pgs.
"U.S. Appl. No. 11/580,584, Final Office Action dated Jan. 22, 2009", 9 pgs.
"U.S. Appl. No. 11/580,584, Response filed Jul. 22, 2009 to Final Office Action dated Jan. 22, 2009", 6 pgs.
"U.S. Appl. No. 11/580,584, Final Office Action dated Oct. 16, 2009", 8 pgs.
"U.S. Appl. No. 11/580,584, Appeal Brief filed Nov. 15, 2010", 11 pgs.
"U.S. Appl. No. 11/580,584, Notice of Allowance dated Feb. 4, 2011", 7 pgs.
"U.S. Appl. No. 11/633,724, Final Office Action dated Dec. 8, 2009", 5 pgs.
"U.S. Appl. No. 11/633,724, Response filed Jun. 8, 2010 to Final Office Action dated Dec. 8, 2009", 4 pgs.

(56) References Cited

OTHER PUBLICATIONS

"U.S. Appl. No. 11/633,724, Final Office Action dated Jun. 22, 2010", 6 pgs.
"U.S. Appl. No. 11/633,724, Response filed Dec. 22, 2010 to Non Final Office Action dated Dec. 8, 2009", 6 pgs.
"U.S. Appl. No. 11/633,724, Notice of Allowance dated Jan. 7, 2011", 4 pgs.
"U.S. Appl. No. 11/633,724, Notice of Allowance dated Aug. 8, 2011", 5 pgs.
"U.S. Appl. No. 11/633,724, 312 Amendment filed Nov. 8, 2011", 4 pgs.
"U.S. Appl. No. 11/633,724, PTO Response to 312 Amendment dated Nov. 17, 2011", 2 pgs.
"U.S. Appl. No. 11/978,752, Restriction Requirement dated Nov. 6, 2009", 7 pgs.
"U.S. Appl. No. 11/978,752, Response filed May 10, 2010 to Restriction Requirement dated Nov. 6, 2009", 4 pgs.
"U.S. Appl. No. 11/978,752, Non Final Office Action dated May 20, 2010", 6 pgs.
"U.S. Appl. No. 11/978,752, Response filed Nov. 5, 2010 to Non Final Office Action dated May 20, 2010", 4 pgs.
"U.S. Appl. No. 11/978,752, Final Office Action dated Dec. 22, 2010", 6 pgs.
"U.S. Appl. No. 11/978,752, Response filed Jun. 22, 2011 to Final Office Action dated Dec. 22, 2010", 6 pgs.
"U.S. Appl. No. 11/978,752, Notice of Allowance dated Aug. 31, 2011", 5 pgs.
"U.S. Appl. No. 11/978,753, Non Final Office Action dated Sep. 3, 2010", 8 pgs.
"U.S. Appl. No. 11/978,753, Response filed Mar. 3, 2011 to Non Final Office Action dated Sep. 3, 2010", 9 pgs.
"U.S. Appl. No. 11/978,753, Final Office Action dated May 2, 2011", 8 pgs.
"U.S. Appl. No. 11/981,112, Non Final Office Action dated Jul. 8, 2009", 11 pgs.
"U.S. Appl. No. 11/981,112, Response filed Jan. 6, 2010 to Non Final Office Action dated Jul. 8, 2009", 7 pgs.
"U.S. Appl. No. 11/981,112, Final Office Action dated Apr. 29, 2010", 9 pgs.
"U.S. Appl. No. 11/981,112, Response filed Nov. 1, 2010 to Final Office Action dated Apr. 29, 2010", 7 pgs.
"U.S. Appl. No. 11/981,112, Final Office Action dated Oct. 8, 2013", 9 pgs.
"U.S. Appl. No. 11/981,112, Response file d Jan. 8, 2014 to Final Office Action dated Oct. 8, 2013", 11 pgs.
"U.S. Appl. No. 11/981,112, Response filed Jan. 12, 2014 to Final Office Action dated Oct. 24, 2014", 9 pgs.
"U.S. Appl. No. 11/981,112, Advisory Action dated Jan. 31, 2014", 3 pgs.
"U.S. Appl. No. 11/981,112, Non Final Office Action dated Feb. 28, 2014", 9 pgs.
"U.S. Appl. No. 11/981,112, Response filed Jun. 27, 2014 to Non Final Office Action dated Feb. 28, 2014", 11 pgs.
"U.S. Appl. No. 11/981,112, Examiner Interview Summary dated Jul. 3, 2014", 3 pgs.
"U.S. Appl. No. 11/981,112, Final Office Action dated Oct. 24, 2014", 7 pgs.
"U.S. Appl. No. 12/288,031, Restriction Requirement dated Nov. 4, 2011", 9 pgs.
"U.S. Appl. No. 12/288,031, Final Office Action dated Jan. 3, 2012", 9 pgs.
"U.S. Appl. No. 12/288,031, Response filed Apr. 4, 2012 to Restriction Requirement dated Nov. 4, 2011", 3 pgs.
"U.S. Appl. No. 12/288,031, Non Final Office Action dated May 10, 2012", 7 pgs.
"U.S. Appl. No. 12/288,031, Non Final Office Action dated May 10, 2012", 8 pgs.
"U.S. Appl. No. 12/288,031, Response filed Oct. 10, 2012 to Non Final Office Action dated May 10, 2012", 11 pgs.
"U.S. Appl. No. 12/288,031, Response filed Mar. 25, 2013 to Final Office Action dated Jan. 3, 2013", 11 pgs.
"U.S. Appl. No. 12/288,031, Advisory Action dated Apr. 12, 2013", 3 pgs.
"U.S. Appl. No. 12/288,031, Non Final Office Action dated Jul. 15, 2013", 9 pgs.
"U.S. Appl. No. 12/288,031, Response filed Nov. 15, 2013 to Non Final Office Action dated Jul. 15, 2013", 11 pgs.
"U.S. Appl. No. 12/288,031, Final Office Action dated Mar. 12, 2014", 14 pgs.
"U.S. Appl. No. 12/288,031, Response filed Jun. 5, 2014 to Final Office Action dated Mar. 12, 2014", 15 pgs.
"U.S. Appl. No. 12/288,031, Advisory Action dated Jul. 7, 2014", 4 pgs.
"U.S. Appl. No. 12/288,031, Response filed Sep. 10, 2014 to Advisory Action dated Jul. 7, 2014", 16 pgs.
"U.S. Appl. No. 12/288,031, Non Final Office Action dated Feb. 17, 2015", 17 pgs.
"U.S. Appl. No. 12/288,032, Restriction Requirement dated Nov. 4, 2011", 9 pgs.
"U.S. Appl. No. 12/288,034, Restriction Requirement dated Nov. 3, 2011", 9 pgs.
"U.S. Appl. No. 12/288,034, Response filed May 1, 2012 to Restriction Requirement dated Nov. 3, 2011", 4 pgs.
"U.S. Appl. No. 12/288,034, Non Final Office Action dated Jun. 22, 2012", 7 pgs.
"U.S. Appl. No. 12/288,034, Response filed Dec. 21, 2012 to Non Final Office Action dated Jun. 22, 2012", 12 pgs.
"U.S. Appl. No. 12/288,034, Final Office Action dated Nov. 4, 2013", 8 pgs.
"U.S. Appl. No. 12/288,034, Response filed Feb. 4, 2014 to Final Office Action dated Nov. 4, 2013", 12 pgs.
"U.S. Appl. No. 12/288,034, Advisory Action dated Feb. 25, 2014", 3 pgs.
"U.S. Appl. No. 12/288,034, Non Final Office Action dated May 8, 2014", 8 pgs.
"U.S. Appl. No. 12/288,034, Response filed Aug. 1, 2014 to Non Final Office Action dated May 8, 2014", 11 pgs.
"U.S. Appl. No. 12/288,034, Final Office Action dated Dec. 1, 2014", 8 pgs.
"U.S. Appl. No. 12/288,045, Restriction Requirement dated Nov. 16, 2011", 9 pgs.
"U.S. Appl. No. 12/315,015, Preliminary Amendment filed Mar. 10, 2009", 3 pgs.
"U.S. Appl. No. 12/315,015, Non Final Office Action dated Oct. 6, 2011", 11 pgs.
"U.S. Appl. No. 12/315,015, Response filed Apr. 6, 2012 to Non Final Office Action dated Oct. 6, 2011", 12 pgs.
"U.S. Appl. No. 12/315,015, Final Office Action dated Apr. 26, 2012", 7 pgs.
"U.S. Appl. No. 12/315,015, Response filed Aug. 27, 2012 to Final Office Action dated Apr. 26, 2012", 6 pgs.
"U.S. Appl. No. 12/315,015, Advisory Action dated Sep. 12, 2012", 3 pgs.
"U.S. Appl. No. 12/315,015, Non Final Office Action dated Sep. 27, 2013", 7 pgs.
"U.S. Appl. No. 12/315,015, Response filed Dec. 27, 2013 to Non Final Office Action dated Sept. 27, 2013", 7 pgs.
"U.S. Appl. No. 12/315,015, Final Office Action dated Jan. 28, 2014", 8 pgs.
"U.S. Appl. No. 12/315,015, Response filed Mar. 28, 2014 to Final Office Action dated Jan. 24, 2014", 5 pgs.
"U.S. Appl. No. 12/315,015, Advisory Action dated Apr. 7, 2014", 3 pgs.
"U.S. Appl. No. 12/315,015, Response filed Jun. 17, 2014 to Final Office Action dated Jan. 28, 2014", 7 pgs.
"U.S. Appl. No. 12/315,015, Non Final Office Action dated Aug. 4, 2014", 7 pgs.
"U.S. Appl. No. 12/315,015, Response filed Nov. 4, 2014 to Non-Final Office Action dated Aug. 4, 2014", 7 pgs.
"U.S. Appl. No. 12/315,015, Examiner Interview Summary dated Nov. 28, 2014", 3 pgs.

(56) References Cited

OTHER PUBLICATIONS

"U.S. Appl. No. 12/315,015, Final Office Action dated Dec. 5, 2014", 9 pgs.
"U.S. Appl. No. 12/315,015, Response filed Mar. 5, 2015 to Final Office Action dated Dec. 5, 2014", 13 pgs.
"U.S. Appl. No. 12/315,015, Non Final Office Action dated Mar. 30, 2015", 10 pgs.
"U.S. Appl. No. 12/653,219, Non Final Office Action dated May 30, 2012", 16 pgs.
"U.S. Appl. No. 12/917,842, Restriction Requirement dated Sep. 14, 2012", 5 pgs.
"U.S. Appl. No. 12/917,842, Response filed Oct. 15, 2012 to Restriction Requirement dated Sep. 14, 2012", 2 pgs.
"U.S. Appl. No. 12/917,842, Non Final Office Action dated Nov. 13, 2012", 6 pgs.
"U.S. Appl. No. 12/917,842, Response filed Apr. 15, 2013 to Non Final Office Action dated Nov. 13, 2012", 9 pgs.
"U.S. Appl. No. 12/917,842, Notice of Allowance dated May 20, 2013", 8 pgs.
"U.S. Appl. No. 12/917,842, Notice of Allowance dated Aug. 27, 2013", 6 pgs.
"U.S. Appl. No. 12/917,842, Notice of Allowance dated Dec. 2, 2013", 7 pgs.
"U.S. Appl. No. 12/942,232, Non Final Office Action dated Oct. 9, 2013", 13 pgs.
"U.S. Appl. No. 12/942,232, Response filed Jan. 9, 2014 to Non Final Office Action dated Oct. 9, 2013", 11 pgs.
"U.S. Appl. No. 12/942,232, Final Office Action dated May 22, 2014", 17 pgs.
"U.S. Appl. No. 12/942,232, Response filed Jul. 21, 2014 to Final Office Action dated May 22, 2014", 11 pgs.
"U.S. Appl. No. 12/942,232, Advisory Action dated Aug. 7, 2014", 3 pgs.
"U.S. Appl. No. 13/157,242, Preliminary Amendment filed Jun. 9, 2011", 7 pgs.
"U.S. Appl. No. 13/157,242, Restriction Requirement dated May 1, 2012", 6 pgs.
"U.S. Appl. No. 13/157,242, Response filed Jun. 1, 2012 to Restriction Requirement dated May 1, 2012", 3 pgs.
"U.S. Appl. No. 13/157,242, Non Final Office Action dated Jun. 18, 2012", 9 pgs.
"U.S. Appl. No. 13/157,242, Response filed Dec. 18, 2012 to Non Final Office Action dated Jun. 18, 2012", 11 pgs.
"U.S. Appl. No. 13/157,242, Final Office Action dated May 16, 2013", 7 pgs.
"U.S. Appl. No. 13/157,242, Response filed Jul. 16, 2013 to Final Office Action dated May 16, 2013", 9 pgs.
"U.S. Appl. No. 13/157,242, Advisory Action dated Jul. 30, 2013", 3 pgs.
"U.S. Appl. No. 13/157,242, Non Final Office Action dated Oct. 31, 2013", 6 pgs.
"U.S. Appl. No. 13/157,242, Response filed Jan. 28, 2014 to Non Final Office Action dated Oct. 31, 2013", 11 pgs.
"U.S. Appl. No. 13/157,242, Notice of Allowance dated Feb. 26, 2014", 8 pgs.
"U.S. Appl. No. 13/157,242, Notice of Allowance dated May 9, 2014", 8 pgs.
"U.S. Appl. No. 13/157,242, Notice of Allowance dated Aug. 21, 2014", 8 pgs.
"U.S. Appl. No. 13/157,242, Notice of Allowance dated Jan. 14, 2015", 8 pgs.
"U.S. Appl. No. 13/162,384, Preliminary Amendment filed Jun. 16, 2011", 7 pgs.
"U.S. Appl. No. 13/162,384, Non Final Office Action dated Mar. 28, 2013", 8 pgs.
"U.S. Appl. No. 13/162,384, Response filed Jun. 27, 2013", 9 pgs.
"U.S. Appl. No. 13/162,384, Final Office Action dated Aug. 27, 2013", 14 pgs.
"U.S. Appl. No. 13/162,384, Response filed Oct. 18, 2013 to Final Office Action dated Aug. 27, 2013", 5 pgs.

"U.S. Appl. No. 13/162,384, Advisory Action dated Nov. 15, 2013", 3 pgs.
"U.S. Appl. No. 13/162,384, Non Final Office Action dated Jul. 21, 2014", 15 pgs.
"U.S. Appl. No. 13/162,384, Response filed Oct. 20, 2014 to Non Final Office Action dated Jul. 21, 2014", 12 pgs.
"U.S. Appl. No. 13/162,384, Examiner Interview Summary dated Oct. 22, 2014", 3 pgs.
"U.S. Appl. No. 13/162,384, Examiner Interview Summary dated Feb. 24, 2015", 1 pg.
"U.S. Appl. No. 13/162,384, Non Final Office Action dated Feb. 24, 2015", 14 pgs.
"U.S. Appl. No. 13/291,942, Non Final Office Action dated Dec. 20, 2012", 5 pgs.
"U.S. Appl. No. 13/291,942, Response filed Apr. 17, 2013 to Non-Final Office Action dated Dec. 20, 2012", 8 pgs.
"U.S. Appl. No. 13/291,942, Final Office Action dated Jan. 3, 2014", 10 pgs.
"U.S. Appl. No. 13/495,836, Preliminary Amendment filed Jun. 13, 2012", 8 pgs.
"U.S. Appl. No. 13/495,836, Non Final Office Action dated Dec. 26, 2012", 9 pgs.
"U.S. Appl. No. 13/495,836, Response filed Mar. 25, 2013 to Non Final Office Action dated Dec. 26, 2012", 9 pgs.
"U.S. Appl. No. 13/495,836, Non Final Office Action dated Aug. 5, 2013", 7 pgs.
"U.S. Appl. No. 13/495,836, Response filed Nov. 15, 2013 to Non Final Office Action dated Aug. 5, 2013", 8 pgs.
"U.S. Appl. No. 13/495,836, Notice of Allowance dated Dec. 4, 2013", 9 pgs.
"U.S. Appl. No. 14/230,469, Non Final Office Action dated May 7, 2015", 8 pgs.
"U.S. Appl. No. 14/595,928, Preliminary Amendment filed Jan. 14, 2015", 8 pgs.
"U.S. Appl. No. 13/291,942, Preliminary Amendment filed Nov. 8, 2011", 3 pgs.
"Australian Application Serial No. 2002351188, Office Action dated Mar. 30, 2007", 1 pg.
"Australian Application Serial No. 2002351188, Office Action dated Dec. 8, 2008", 3 pgs.
"Australian Application Serial No. 2002353807, First Examiner Report dated Nov. 16, 2006", 2 pgs.
"Australian Application Serial No. 2004277897, First Examiner Report dated Oct. 14, 2009", 2 pgs.
"Australian Application Serial No. 2004277897, Response filed Jul. 14, 2011 to First Examiner Report dated Oct. 14, 2009", 9 pgs.
"Australian Application Serial No. 2004287354, Office Action dated Oct. 13, 2009", 2 pgs.
"Australian Application Serial No. 2004287355, Office Action dated May 11, 2009", 2 pgs.
"Australian Application Serial No. 2004287355, European Search Report dated Oct. 14, 2009", 6 pgs.
"Australian Application Serial No. 2005204615, Office Action dated Jan. 20, 2010", 4 pgs.
"Australian Application Serial No. 2005235108, Office Action dated Feb. 26, 2010", 3 pgs.
"Australian Application Serial No. 2006302908, Office Action dated Mar. 4, 2011", 8 pgs.
"Australian Application Serial No. 2006305688, First Examiner Report dated Mar. 10, 2011", 3 pgs.
"Australian Application Serial No. 2006305688, Response filed Oct. 22, 2012 to First Examiner Report dated Mar. 10, 2011", 16 pgs.
"Australian Application Serial No. 2006305689, Office Action dated Sep. 5, 2011", 3 pgs.
"Australian Application Serial No. 2006309241, Office Action dated Mar. 4, 2011", 6 pgs.
"Australian Application Serial No. 2008243229, First Examiner Report dated Apr. 13, 2010", 2 pgs.
"Australian Application Serial No. 2008243229, Response filed May 13, 2011 to Office Action dated Apr. 13, 2010", 15 pgs.
"Australian Application Serial No. 2011224089, First Examiners Report dated Mar. 27, 2013", 3 pgs.

(56) References Cited

OTHER PUBLICATIONS

"Australian Application Serial No. 2011224089, Response filed Mar. 21, 2014 to First Examiners Report dated Mar. 27, 2013", 74 pgs.
"Australian Application Serial No. 2011253682, Office Action dated Sep. 27, 2012", 4 pgs.
"Australian Application Serial No. 2011253682, Response filed Jul. 17, 2013 to Office Action dated Sep. 27, 2012", 19 pgs.
"Canadian Application Serial No. 2,464,900, Office Action dated Sep. 29, 2009", 3 pgs.
"Canadian Application Serial No. 2,539,585, Office Action dated Aug. 31, 2010", 2 pgs.
"Canadian Application Serial No. 2,539,585, Office Action dated Sep. 19, 2012", 2 pgs.
"Canadian Application Serial No. 2,546,681, Office Action dated Feb. 25, 2011", 3 pgs.
"Canadian Application Serial No. 2,546,721, Office Action dated Aug. 31, 2010", 2 pgs.
"Canadian Application Serial No. 2,546,721, Office Action dated Feb. 25, 2011", 3 pgs.
"Canadian Application Serial No. 2,546,721, Response filed Aug. 1, 2012 to Office Action dated Feb. 25, 2011", 9 pgs.
"Canadian Application Serial No. 2,551,685, Office Action dated Jan. 17, 2011", 3 pgs.
"Canadian Application Serial No. 2,554,022, Office Action dated Jun. 22, 2011", 3 pgs.
"Canadian Application Serial No. 2,554,022, Office Action dated Aug. 31, 2010", 2 pgs.
"Canadian Application Serial No. 2,558,317, Office Action dated Aug. 31, 2010", 2 pgs.
"Canadian Application Serial No. 2,558,317, Office Action dated Sep. 28, 2011", 3 pgs.
"Canadian Application Serial No. 2,626,403, Office Action dated Apr. 2, 2013", 3 pgs.
"Canadian Application Serial No. 2,626,403, Response filed Feb. 12, 2014 to Office Action dated Apr. 2, 2013", 20 pgs.
"Chinese Application Serial No. 02823581.9, Office Action dated Mar. 1, 2006", 7 pgs.
"Chinese Application Serial No. 02823581.9, Response filed Apr. 7, 2006 to Office Action dated Mar. 1, 2006", 4 pgs.
"Chinese Application Serial No. 02823581.9, Response filed Jan. 31, 2007 to Office Action dated Nov. 17, 2006", 8 pgs.
"Chinese Application Serial No. 02823581.9, Office Action dated Aug. 8, 2007", 4 pgs.
"Chinese Application Serial No. 02823581.9, Response filed Dec. 3, 2007 to Office Action dated Aug. 8, 2007", 6 pgs.
"Chinese Application Serial No. 02823581.9, Office Action dated Apr. 18, 2008", (W/ English Translation), 6 pgs.
"Chinese Application Serial No. 02823581.9, Response filed May 19, 2008 to Office Action dated Apr. 18, 2008", (W/ English Translation), 38 pgs.
"Chinese Application Serial No. 02823581.9, Office Action dated Nov. 17, 2006", 7 pgs.
"Chinese Application Serial No. 200480027649.7, Office Action dated Jun. 23, 2008", w/English translation, 5 pgs.
"Chinese Application Serial No. 200480027649.7, Office Action dated Sep. 4, 2009", w/English translation, 18 pgs.
"Chinese Application Serial No. 200480027649.7, Response filed Jan. 19, 2010 to Office Action dated Sep. 4, 2009", 5 pgs.
"Chinese Application Serial No. 200480027649.7, Office Action dated Dec. 24, 2010", w/English translation, 6 pgs.
"Chinese Application Serial No. 200480027649.7, Response filed Mar. 8, 2011 to Office Action dated Dec. 24, 2010", w/English translation, 7 pgs.
"Chinese Application Serial No. 200480031226.2, Office Action dated Jan. 23, 2009", w/English translation, 9 pgs.
"Chinese Application Serial No. 200480031226.2, Response filed May 22, 2009 to Office Action dated Jan. 23, 2009", 5 pgs.
"Chinese Application Serial No. 200480031226.2, Office Action dated Apr. 27, 2010", (W/ English Translation), 7 pgs.
"Chinese Application Serial No. 200480031226.2, Response filed Jul. 12, 2010 to Office Action dated Apr. 27, 2010", 5 pgs.
"Chinese Application Serial No. 200480031226.2, Office Action dated Dec. 21, 2010", (W/ English Translation), 10 pgs.
"Chinese Application Serial No. 200480031226.2, Response filed Feb. 25, 2011 to Office Action dated Dec. 21, 2010", (W/ English Translation), 18 pgs.
"Chinese Application Serial No. 200580002026.9, Office Action dated Jul. 19, 2009", (W/ English Translation), 12 pgs.
"Chinese Application Serial No. 200580002026.9, Response filed Jan. 4, 2010 to Office Action dated Jun. 19, 2009", 10 pgs.
"Chinese Application Serial No. 200580006169.7, Office Action dated Mar. 1, 2010", w/English translation, 12 pgs.
"Chinese Application Serial No. 200580006169.7, Response filed Jul. 14, 2010 to Office Action dated Mar. 1, 2010", w/English translation, 32 pgs.
"Chinese Application Serial No. 200580009570.6, Office Action dated May 9, 2008", (W/ English Translation), 2 pgs.
"Chinese Application Serial No. 200580009570.6, Response filed Nov. 21, 2008 to Office Action dated May 9, 2008", 7 pgs.
"Chinese Application Serial No. 200680034052.4, Office Action dated Aug. 14, 2009", w/English translation, 13 pgs.
"Chinese Application Serial No. 200680034052.4, Response filed Mar. 1, 2010 to Office Action dated Aug. 14, 2009", 4 pgs.
"Chinese Application Serial No. 200680034052.4, Office Action dated May 11, 2010", w/English translation, 7 pgs.
"Chinese Application Serial No. 200680034052.4, Response filed Sep. 26, 2010 to Office Action dated May 11, 2010", 5 pgs.
"Chinese Application Serial No. 200680038882.4, Office Action dated May 11, 2010", (W/ English Translation), 18 pgs.
"Chinese Application Serial No. 200680046854.7, Office Action dated Apr. 14, 2010", (W/ English Translation), 18 pgs.
"Chinese Application Serial No. 200680046854.7, Response filed Sep. 26, 2010 to Office Action dated Apr. 14, 2010", 10 pgs.
"Chinese Application Serial No. 200680047552.1, Office Action dated Jun. 4, 2010", (W/ English Translation), 7 pgs.
"Chinese Application Serial No. 200680047552.1, Response filed Dec. 20, 2010 to Office Action dated Jun. 4, 2010", 10 pgs.
"Chinese Application Serial No. 200810210922.X, Office Action dated Apr. 2, 2010", (W/ English Translation), 4 pgs.
"Chinese Application Serial No. 200810210922.X, Response filed Aug. 12, 2010 to Office Action dated Apr. 2, 2010", 10 pgs.
"Chinese Application Serial No. 200810210922.X, Office Action dated Aug. 23, 2011", 6 pgs.
"Chinese Application Serial No. 200810210922.X, Office Action dated Jan. 19, 2012", (W/ English Translation), 6 pgs.
"Chinese Application Serial No. 200810210922.X, Response filed Jun. 1, 2012 to Office Action dated Jan. 19, 2012", 5 pgs.
"Chinese Application Serial No. 200910139527.1, Office Action dated Jul. 12, 2010", w/English translation, 9 pgs.
"Chinese Application Serial No. 200910139527.1, Response filed Nov. 28, 2011 to Office Action dated Jul. 12, 2010", 9 pgs.
"European Application Serial No. 02789196.9, European Search Report dated Aug. 14, 2009", 5 pgs.
"European Application Serial No. 02789196.9, Office Action dated Apr. 19, 2010", 4 pgs.
"European Application Serial No. 02789196.9, Response filed Oct. 25, 2010 to Office Action dated Apr. 19, 2010", 16 pgs.
"European Application Serial No. 02789196.9, Office Action dated Jul. 14, 2011", 3 pgs.
"European Application Serial No. 02789196.9, Response filed Jan. 18, 2012 to Office Action dated Jul. 14, 2011", 19 pgs.
"European Application Serial No. 02789196.9, Office Action dated Feb. 6, 2012", 4 pgs.
"European Application Serial No. 02789196.9, Response filed Feb. 16, 2012 to Office Action dated Feb. 6, 2012", 9 pgs.
"European Application Serial No. 02789196.9, Office Action dated Mar. 7, 2012", 3 pgs.
"European Application Serial No. 02789196.9, Response filed Apr. 5, 2012 to Office Action dated Mar. 7, 2012", 5 pgs.
"European Application Serial No. 04788653.6, Office Action dated May 19, 2006", 2 pgs.

(56) References Cited

OTHER PUBLICATIONS

"European Application Serial No. 04788653.6, European Search Report dated Aug. 6, 2014", 3 pgs.
"European Application Serial No. 04788653.6, Response filed Oct. 21, 2014 to European Search Report dated Aug. 6, 2014", 4 pgs.
"European Application Serial No. 04788653.6, Examination Notification Art. 94(3) dated Mar. 3, 2015", 4 pgs.
"European Application Serial No. 05704902.5, European Search Report dated Aug. 29, 2011", 3 pgs.
"European Application Serial No. 05713941.2, Office Action dated Dec. 13, 2007", 2 pgs.
"European Application Serial No. 05713941.2, European Search Report dated Apr. 10, 2014", 6 pgs.
"European Application Serial No. 05713941.2, Examination Notification Art. 94(3) dated Jun. 5, 2014", 7 pgs.
"European Application Serial No. 05713941.2, Response filed Dec. 22, 2014 to Examination Notification Art. 94(3) dated Jun. 5, 2014", 15 pgs.
"European Application Serial No. 05723408.0, Examination Notification Art. 94(3) dated Jul. 10, 2014", 6 pgs.
"European Application Serial No. 05723408.0, Response filed Jan. 19, 2015 to Examination Notification Art. 94(3) dated Jul. 10, 2014", 16 pgs.
"European Application Serial No. 06802573.3, Office Action dated May 28, 2008", 2 pgs.
"European Application Serial No. 06802573.3, Extended European Search Report dated Feb. 15, 2012", 6 pgs.
"European Application Serial No. 06802573.3, Office Action dated Mar. 5, 2012", 1 pg.
"European Application Serial No. 06802573.3, Response filed Sep. 3, 2012 to Office Action dated Mar. 5, 2012", 15 pgs.
"European Application Serial No. 06802578.2, European Search Report dated Mar. 7, 2013", 10 pgs.
"European Application Serial No. 06802580.8, Office Action dated Feb. 25, 2013", 3 pgs.
"European Application Serial No. 06802580.8, Extended European Search Report dated Sep. 24, 2013", 8 pgs.
"European Application Serial No. 06802580.8, Response filed Apr. 17, 2014 to Extended European Search Report dated Sep. 24, 2013", 2 pgs.
"European Application Serial No. 09075319.5, Extended European Search Report dated Oct. 14, 2009", 6 pgs.
"European Application Serial No. 09075319.5, Office Action dated Jan. 14, 2010", 1 pgs.
"European Application Serial No. 09075319.5, Office Action dated Oct. 14, 2010", 4 pgs.
"European Application Serial No. 09820886.1, Office Action dated Jun. 7, 2011", 2 pgs.
"European Application Serial No. 09820886.1, Response filed Dec. 8, 2011 to Office Action dated Jun. 7, 2011", 3 pgs.
"European Application Serial No. 09820886.1, Extended European Search Report dated Mar. 27, 2015", 8 pgs.
"European Application Serial No. 09820891.1, Office Action dated Jun. 7, 2011", 2 pgs.
"European Application Serial No. 09820891.1, Response filed Dec. 8, 2011 to Office Action dated Jun. 7, 2011", 2 pgs.
"European Application Serial No. 09075319.5, Response filed Jul. 20, 2010 to Office Action dated Jan. 14, 2010", 13 pgs.
"European Application Serial No. 09075319.5, Response filed Feb. 21, 2011 to Office Action dated Oct. 14, 2010", 5 pgs.
"German Application Serial No. 10297483.7, Office Action dated Jan. 9, 2006", 4 pgs.
"German Application Serial No. 10297483.7, Response filed Jul. 7, 2006 to Office Action dated Jan. 9, 2006", 14 pgs.
"German Application Serial No. 10297483.7, Office Action dated Jul. 8, 2006", 2 pgs.
"German Application Serial No. 10297483.7, Response filed Oct. 26, 2006 to Office Action dated Jul. 8, 2006", 3 pgs.
"German Application Serial No. 10297483.7, Office Action dated and Response filed Oct. 30, 2006", 8 pgs.
"Great Britain Application Serial No. 0411107.6, Office Action dated Feb. 28, 2005", 3 pgs.
"Great Britain Application Serial No. 0411107.6, Response filed Aug. 23, 2005 to Office Action dated Feb. 28, 2005", 3 pgs.
"Great Britain Application Serial No. 0411107.6, Office Action dated Sep. 29, 2005", 1 pg.
"Great Britain Application Serial No. 0411107.6, Response filed Oct. 31, 2005 to Office Action dated Sep. 29, 2005", 4 pgs.
"Great Britain Application Serial No. 0522152.8, Office Action dated Dec. 5, 2005", 5 pgs.
"Great Britain Application Serial No. 0522152.8, Response filed Apr. 26, 2006 to Office Action dated Dec. 5, 2005", 48 pgs.
"International Application Serial No. PCT/US2002/032753, International Search Report dated Mar. 6, 2003", 1 pg.
"International Application Serial No. PCT/US2002/032753, Written Opinion dated Aug. 26, 2003", 4 pgs.
"International Application Serial No. PCT/US2002/032753, International Preliminary Examination Report dated Aug. 16, 2004", 3 pgs.
"International Application Serial No. PCT/US2002/038365, International Search Report dated May 8, 2003", 3 pgs.
"International Application Serial No. PCT/US2002/038365, Written Opinion dated Oct. 27, 2003", 4 pgs.
"International Application Serial No. PCT/US2002/038365, International Preliminary Report on Patentability dated Feb. 6, 2004", 3 pgs.
"International Application Serial No. PCT/US2004/027587, International Search Report dated Dec. 27, 2005", 1 pg.
"International Application Serial No. PCT/US2004/027587, Written Opinion dated Dec. 27, 2005", 3 pgs.
"International Application Serial No. PCT/US2004/027587, International Preliminary Report on Patentability dated May 24, 2006", 3 pgs.
"International Application Serial No. PCT/US2004/027589, International Preliminary Report on Patentability dated Apr. 6, 2005", 4 pgs.
"International Application Serial No. PCT/US2004/027589, International Search Report dated Apr. 6, 2005", 1 pg.
"International Application Serial No. PCT/US2004/027589, Written Opinion dated Apr. 6, 2005", 3 pgs.
"International Application Serial No. PCT/US2004/027590, International Search Report dated Jan. 12, 2005", 1 pg.
"International Application Serial No. PCT/US2004/027590, Written Opinion dated Jan. 12, 2005", 3 pgs.
"International Application Serial No. PCT/US2004/027590, International Preliminary Examination Report dated Feb. 16, 2006", 3 pgs.
"International Application Serial No. PCT/US2004/029402, International Search Report dated Feb. 24, 2006", 1 pg.
"International Application Serial No. PCT/US2004/029402, Written Opinion dated Feb. 24, 2006", 3 pgs.
"International Application Serial No. PCT/US2004/029402, International Preliminary Report on Patentability dated Jul. 10, 2006", 3 pgs.
"International Application Serial No. PCT/US2005/00059, International Search Report dated Jan. 5, 2007", 3 pgs.
"International Application Serial No. PCT/US2005/00059, Written Opinion dated Jan. 5, 2007", 8 pgs.
"International Application Serial No. PCT/US2005/00059, International Preliminary Report on Patentability dated May 18, 2007", 8 pgs.
"International Application Serial No. PCT/US2005/005453, International Search Report dated Aug. 30, 2005", 1 pg.
"International Application Serial No. PCT/US2005/005453, International Written Opinion dated Aug. 30, 2005", 3 pgs.
"International Application Serial No. PCT/US2005/005453, Written Opinion dated Aug. 30, 2005", 3 pgs.
"International Application Serial No. PCT/US2005/005453, International Preliminary Report on Patentability dated Feb. 16, 2006", 3 pgs.
"International Application Serial No. PCT/US2005/005453, International Preliminary Examination Report dated Mar. 13, 2006", 3 pgs.

(56) References Cited

OTHER PUBLICATIONS

"International Application Serial No. PCT/US2005/005627, International Search Report dated Sep. 25, 2007", 1 pg.
"International Application Serial No. PCT/US2005/005627, Written Opinion dated Sep. 25, 2007", 3 pgs.
"International Application Serial No. PCT/US2005/005627, International Preliminary Examination Report dated Apr. 7, 2009", 3 pgs.
"International Application Serial No. PCT/US2006/033741, International Search Report dated Mar. 30, 2007", 1 pg.
"International Application Serial No. PCT/US2006/033741, Written Opinion dated Mar. 30, 2007", 4 pgs.
"International Application Serial No. PCT/US2006/033741, International Preliminary Report on Patentability dated Jul. 28, 2007", 5 pgs.
"International Application Serial No. PCT/US2006/033747, International Search Report dated Jul. 8, 2008", 1 pg.
"International Application Serial No. PCT/US2006/033747, Written Opinion dated Jul. 8, 2008", 3 pgs.
"International Application Serial No. PCT/US2006/033747, International Preliminary Report on Patentability dated Mar. 1, 2011", 4 pgs.
"International Application Serial No. PCT/US2006/033748, International Search Report dated Aug. 15, 2007", 1 pg.
"International Application Serial No. PCT/US2006/033748, Written Opinion dated Aug. 15, 2007", 5 pgs.
"International Application Serial No. PCT/US2006/033748, International Preliminary Report on Patentability dated Jun. 18, 2008", 7 pgs.
"International Application Serial No. PCT/US2006/033749, International Search Report dated Aug. 15, 2007", 1 pg.
"International Application Serial No. PCT/US2006/033749, Written Opinion dated Aug. 15, 2007", 5 pgs.
"International Application Serial No. PCT/US2006/033749, International Preliminary Report on Patentability dated Jun. 18, 2008", 6 pgs.
"International Application Serial No. PCT/U52006/037085, International Preliminary Report on Patentability dated Jul. 24, 2008", 9 pgs.
"International Application Serial No. PCT/US2006/037085, International Search Report dated Aug. 30, 2007", 1 pg.
"International Application Serial No. PCT/US2006/037085, Written Opinion dated Aug. 30, 2007", 7 pgs.
"International Application Serial No. PCT/U52009/005604, International Search Report dated Dec. 11, 2009", 2 pgs.
"International Application Serial No. PCT/US2009/005604, Written Opinion dated Dec. 11, 2009", 7 pgs.
"International Application Serial No. PCT/US2009/005604, International Preliminary Report on Patentability dated Jan. 13, 2011", 10 pgs.
"International Application Serial No. PCT/US2009/005607, International Search Report dated Dec. 11, 2009", 2 pgs.
"International Application Serial No. PCT/US2009/005607, Written Opinion dated Dec. 11, 2009", 6 pgs.
"International Application Serial No. PCT/US2009/005607, International Preliminary Report on Patentability dated Jan. 9, 2011", 9 pgs.
"International Application Serial No. PCT/US2009/005608, International Search Report dated Dec. 10, 2009", 2 pgs.
"International Application Serial No. PCT/US2009/005608, Written Opinion dated Dec. 10, 2009", 4 pgs.
"International Application Serial No. PCT/US2009/005608, International Preliminary Report on Patentability dated Jan. 14, 2011", 7 pgs.
"International Application Serial No. PCT/US2009/005609, International Search Report dated Dec. 18, 2009", 2 pgs.
"International Application Serial No. PCT/US2009/005609, Written Opinion dated Dec. 18, 2009", 6 pgs.
"International Application Serial No. PCT/US2009/005609, International Preliminary Report on Patentability dated Jan. 9, 2011", 9 pgs.
"Japanese Application Serial No. 2003-546789, Office Action dated Jun. 17, 2008", w/English translation, 6 pgs.
"Japanese Application Serial No. 2003-546789, Response filed Dec. 11, 2008 to Office Action dated Jun. 17, 2008", w/English translation, 9 pgs.
"Japanese Application Serial No. 2003-546789, Office Action dated Feb. 26, 2009", w/English translation, 7 pgs.
"Japanese Application Serial No. 2003-546789, Response filed May 21, 2009 to Office Action dated Feb. 26, 2009", 6 pgs.
"Japanese Application Serial No. 2003-546789, Office Action dated Oct. 7, 2009", 3 pgs.
"Japanese Application Serial No. 2006-528036, Office Action dated Jun. 23, 2008", w/English translation, 5 pgs.
"Japanese Application Serial No. 2006-528036, Response filed Dec. 25, 2008 to Office Action dated Jun. 23, 2008", w/ English translation, 9 pgs.
"Japanese Application Serial No. 2006-528036, Office Action dated Feb. 26, 2009", w/English translation, 5 pgs.
"Japanese Application Serial No. 2006-528036, Office Action dated Jan. 19, 2010", 3 pgs.
"Japanese Application Serial No. 2006-536616, Office Action dated Jun. 23, 2008", (W/ English Translation), 8 pgs.
"Japanese Application Serial No. 2006-536616, Response filed Dec. 19, 2008 to Office Action dated Jun. 23, 2008", (W/ English Translation), 9 pgs.
"Japanese Application Serial No. 2006-536617, Office Action dated Jun. 17, 2008", (W/ English Translation), 3 pgs.
"Japanese Application Serial No. 2006-536617, Response filed May 12, 2009 to Office Action dated Jun. 17, 2008", (W/ English Translation), 19 pgs.
"Japanese Application Serial No. 2006-547608, Office Action dated Jun. 23, 2008", (W/ English Translation), 5 pgs.
"Japanese Application Serial No. 2006-547608, Response filed Dec. 19, 2008 to Office Action dated Jun. 23, 2008", (W/ English Translation), 10 pgs.
"Japanese Application Serial No. 2007500928, Office Action dated Jul. 1, 2010", w/English translation, 10 pgs.
"Japanese Application Serial No. 2007504965, Office Action dated Sep. 14, 2010", English translation, 1 pg.
"Japanese Application Serial No. 2007504965, Response filed Mar. 11, 2011 to Office Action dated Sep. 14, 2010", 8 pgs.
"Japanese Application Serial No. 2007504965, Office Action dated Jun. 14, 2011", w/English translation, 4 pgs.
"Japanese Application Serial No. 2007504965, Office Action dated Mar. 7, 2012", w/English translation, 4 pgs.
"Japanese Application Serial No. 2008-306790, Office Action dated May 31, 2011", 1 pg.
"Japanese Application Serial No. 2008-306790, Response filed Nov. 29, 2011 to Office Action dated May 8, 2012", 2 pgs.
"Japanese Application Serial No. 2008-306790, Response filed Nov. 29, 2011 to Office Action dated May 31, 2011", (W/ English Translation), 12 pgs.
"Japanese Application Serial No. 2008-316282, Office Action dated May 16, 2011", 2 pgs.
"Japanese Application Serial No. 2008-316296, Office Action dated Jun. 22, 2010", 2 pgs.
"Japanese Application Serial No. 2008-316296, Office Action dated Feb. 28, 2011", 2 pgs.
"Japanese Application Serial No. 2008-323279, Office Action dated Sep. 30, 2010", 1 pg.
"Japanese Application Serial No. 2008-323290, Office Action dated Jun. 8, 2011", (W/ English Translation), 8 pgs.
"Japanese Application Serial No. 2008-323290, Response filed Dec. 7, 2011 to Office Action dated Jun. 8, 2011", (W/ English Translation), 16 pgs.
"Japanese Application Serial No. 2008-323290, Office Action dated Jun. 6, 2012", (W/ English Translation), 8 pgs.
"Japanese Application Serial No. 2008-536574, Office Action dated Mar. 11, 2010", (W/ English Translation), 4 pgs.

(56) References Cited

OTHER PUBLICATIONS

"Japanese Application Serial No. 2008-536574, Office Action dated Oct. 3, 2011", (W/ English Translation), 7 pgs.
"Japanese Application Serial No. 2008-536575, Office Action dated Jul. 7, 2011", (W/ English Translation), 5 pgs.
"Japanese Application Serial No. 2008-536576, Office Action dated Jul. 19, 2011", (W/ English Translation), 4 pgs.
"Japanese Application Serial No. 2008-536577, Office Action dated Jul. 8, 2011", w/English translation, 4 pgs.
"Japanese Application Serial No. 2008-536577, Response filed Jan. 6, 2012 to Office Action dated Jul. 8, 2011", (W/ English Translation), 3 pgs.
"Japanese Application Serial No. 2008-536577, Notice of Allowance dated May 30, 2012", 3 pgs.
U.S. Appl. No. 14/595,928, Filing Date Jan. 13, 2015, Title Endovascular Aneurysm Devices, Systems, and Methods.
"Laparoscopic Surgery", Medical Data International, Inc. MedPro, (1995), 190.
Bolduc, Lee, "Devices, Systems, and Methods for Prosthesis Delivery and Implantation, Including the Use of a Fastener Tool", U.S. Appl. No. 12/917,842, filed Nov. 2, 2010, 120 Pgs.
Gadacz, T., et al., "The Spiral Tracker: A New Technique for Stabilizing Prosthetic Mesh in Laparoscopic Hernia Repair", Surgical Rounds, (Nov. 1995), 461-467.
Hatchett, R. L, et al., "Extraperitoneal Endoscopic Burch Repair Using a Tacker Mesh Technique", (1995), 1-4.
Newman, L., et al., "Tacker-Assisted TAPP Procedure", (1995), 2 pgs.

\* cited by examiner

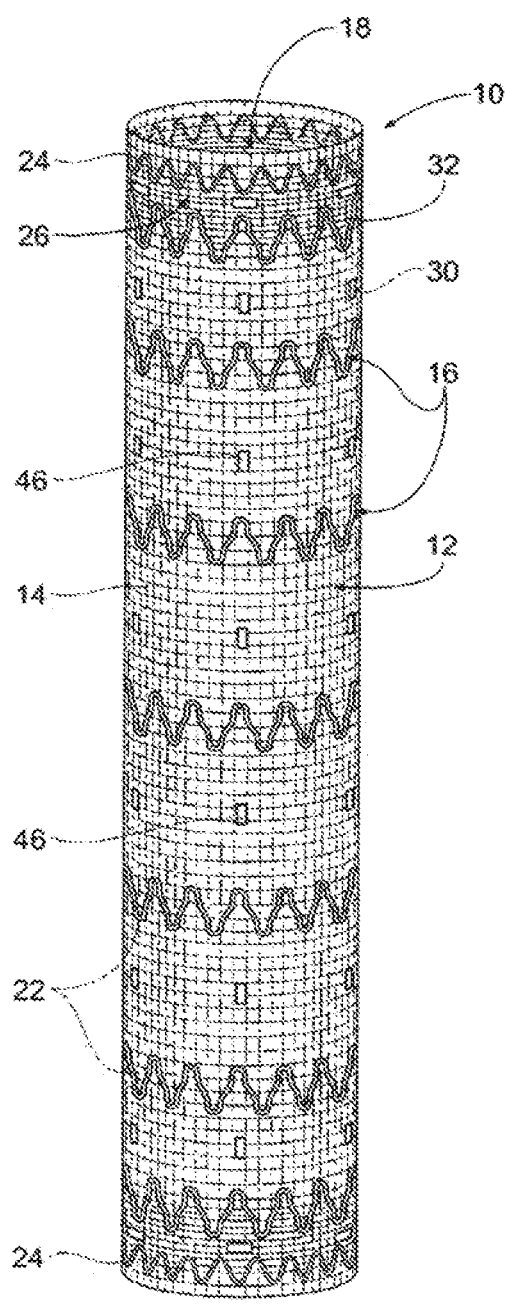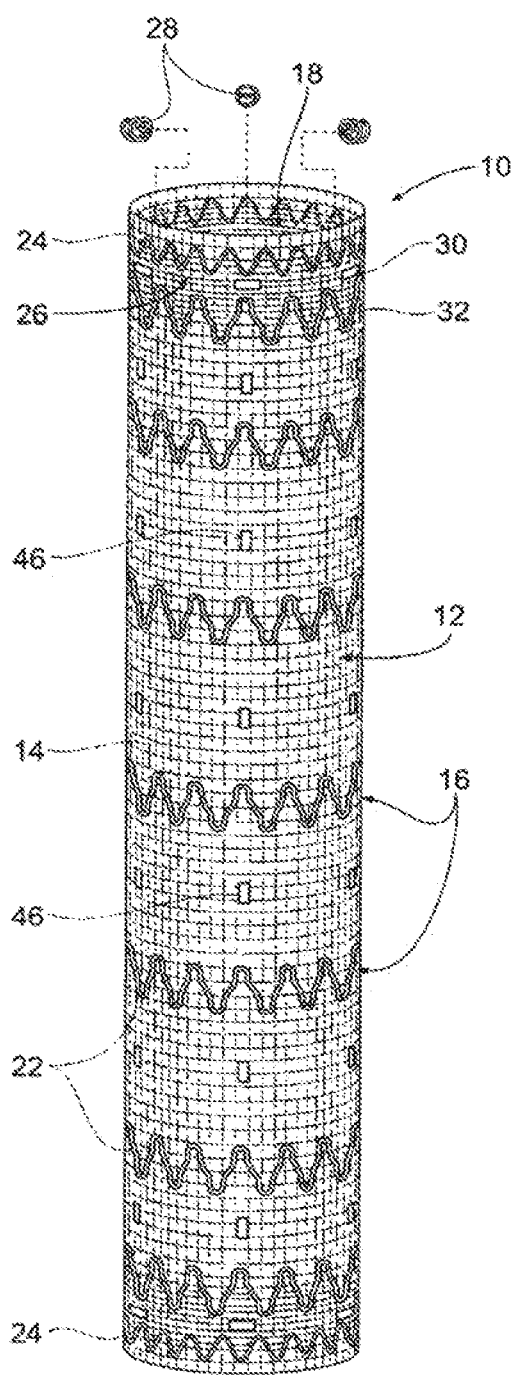
Fig.1
Fig.2

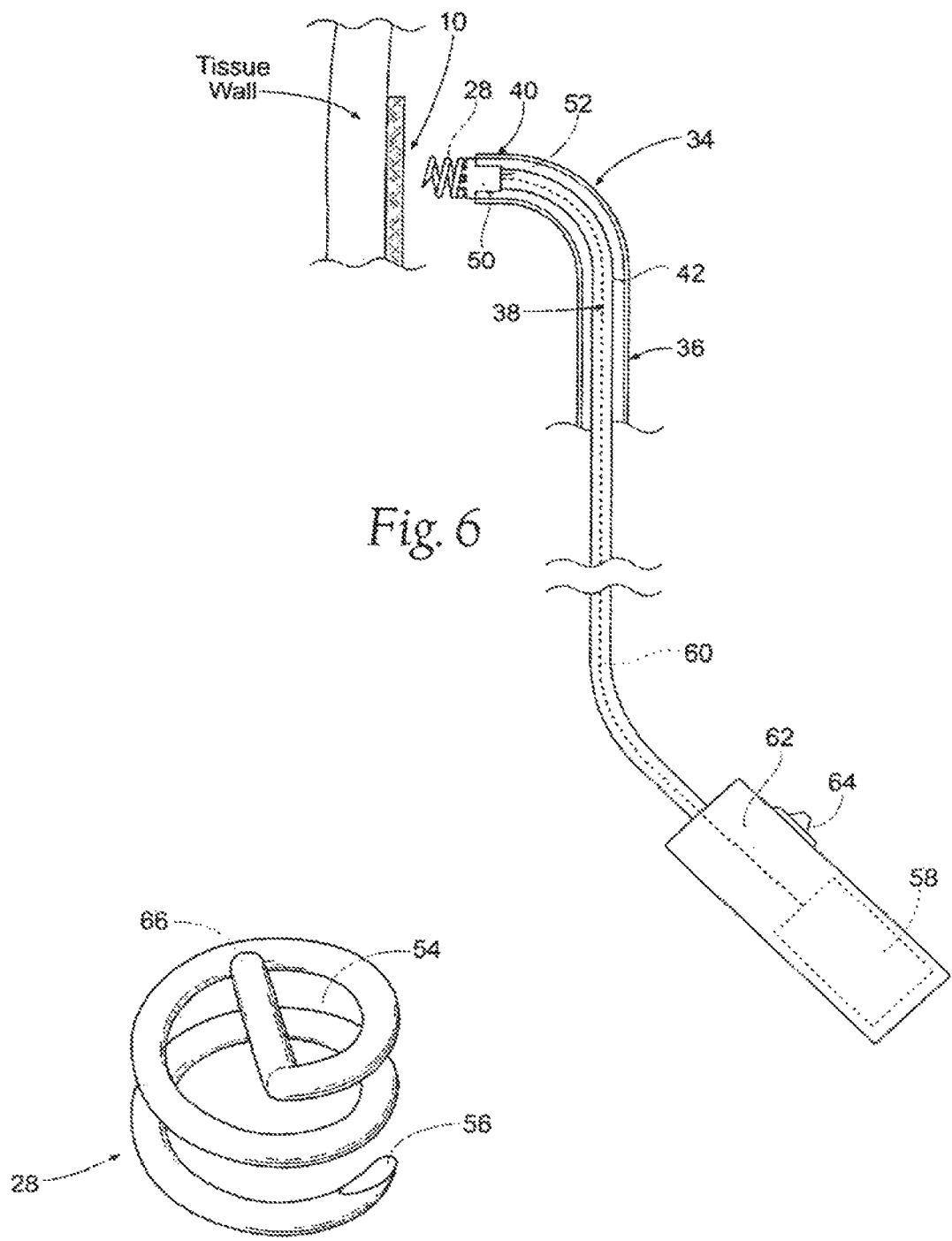

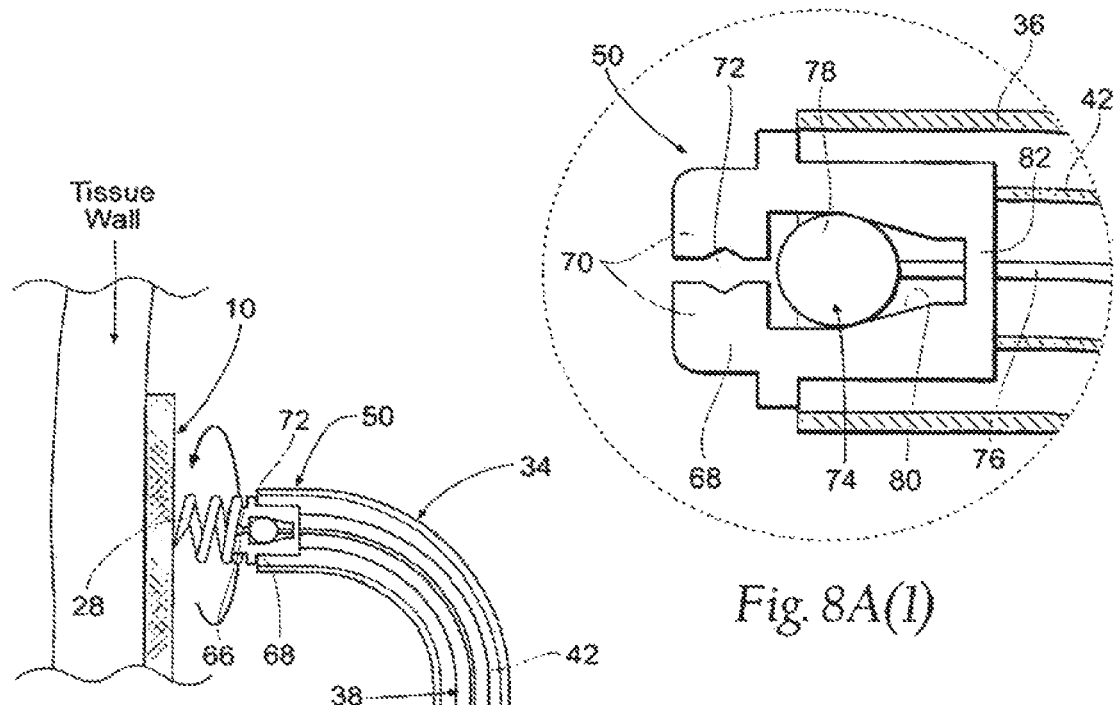
Fig. 8A(1)
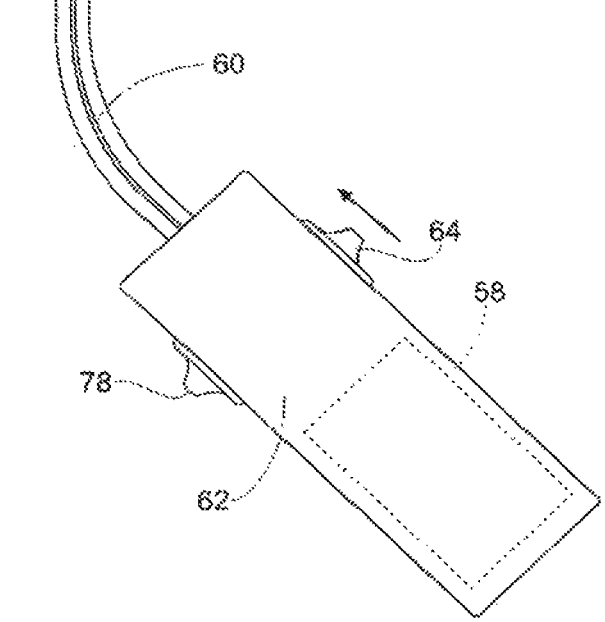
Fig. 8A(2)

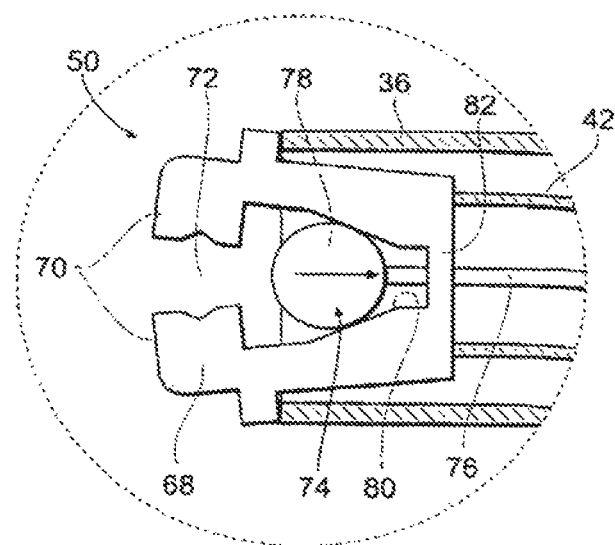
Fig. 8B(1)
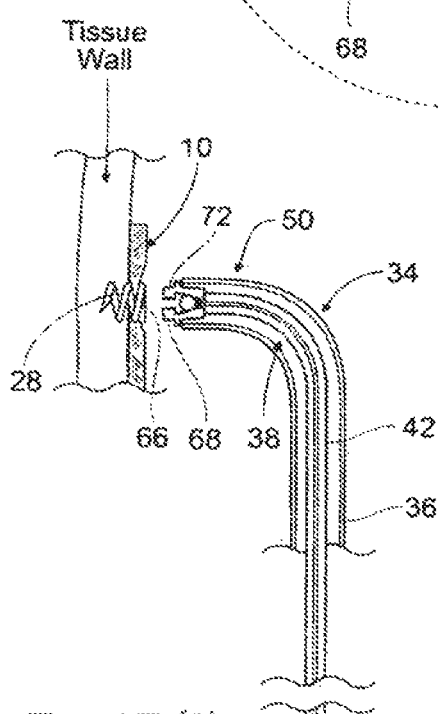
Fig. 8B(2)
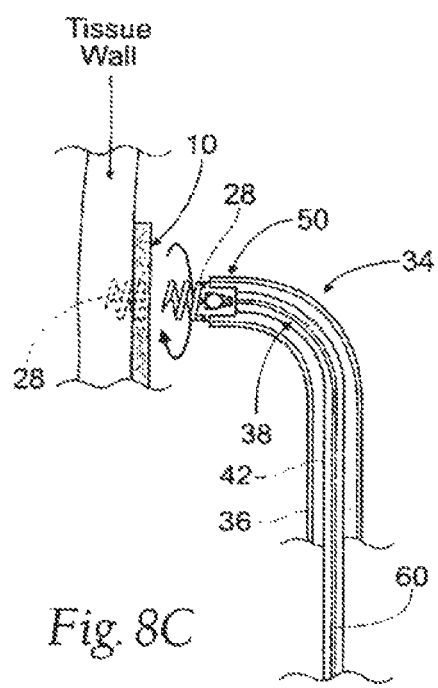
Fig. 8C

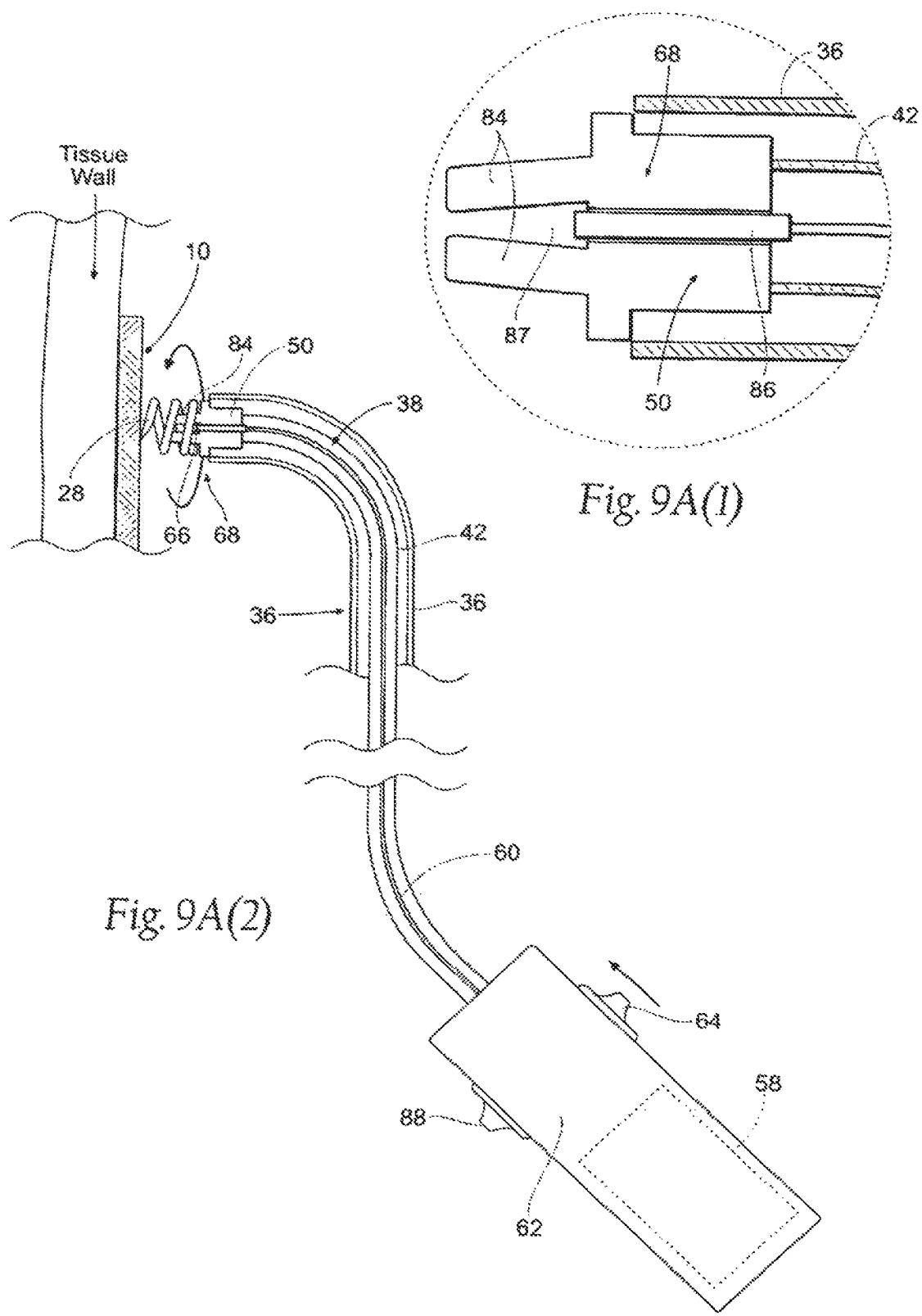

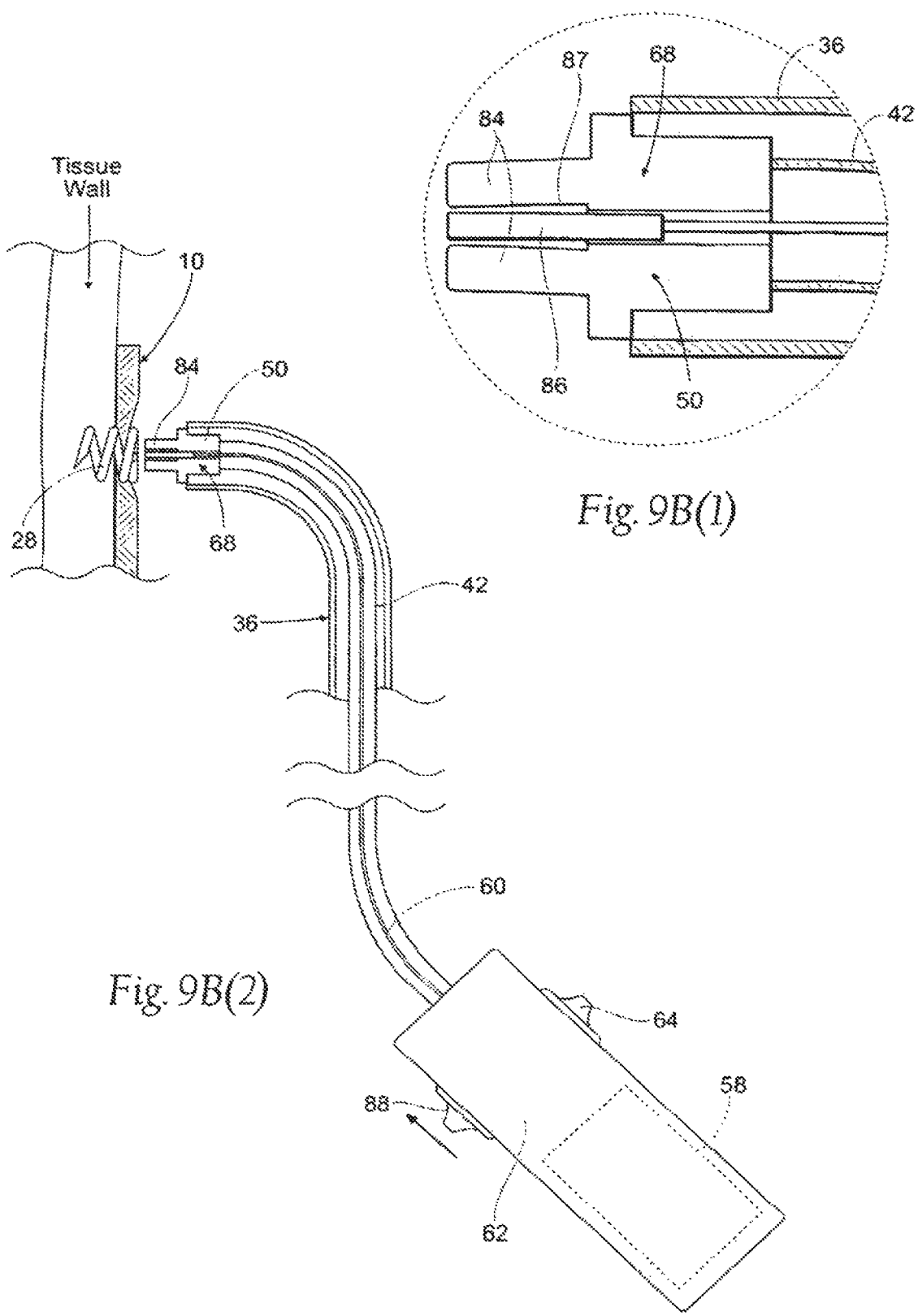

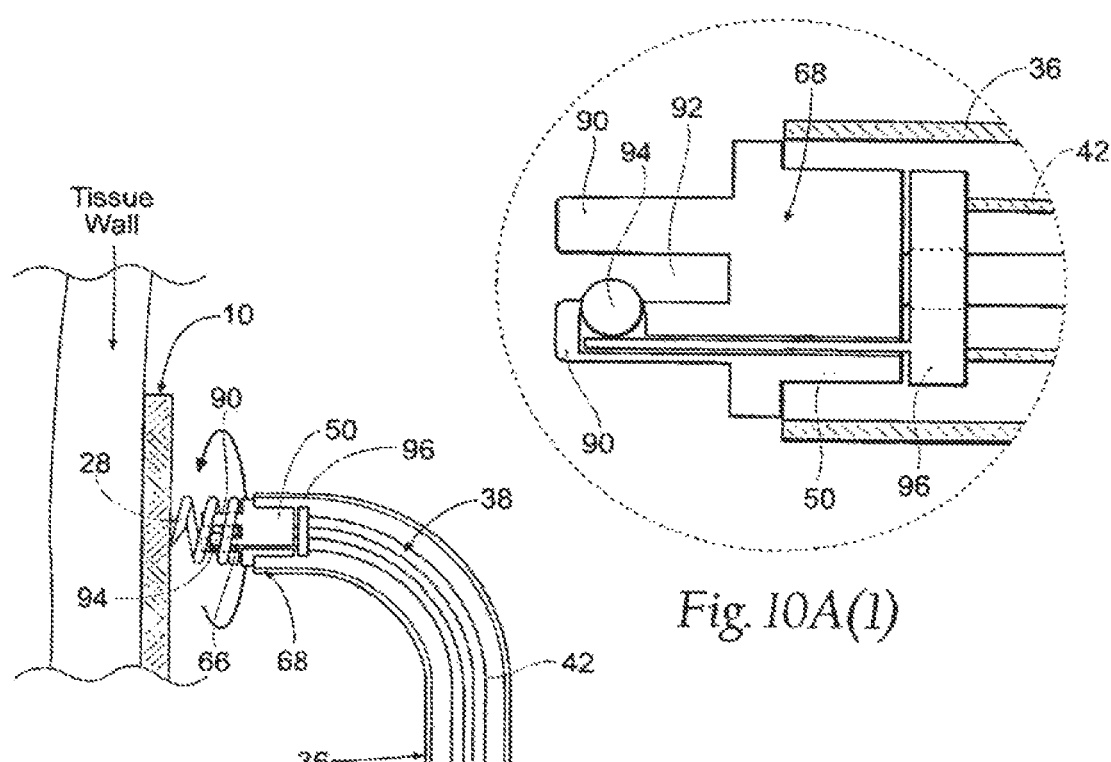
*Fig. 10A(1)*
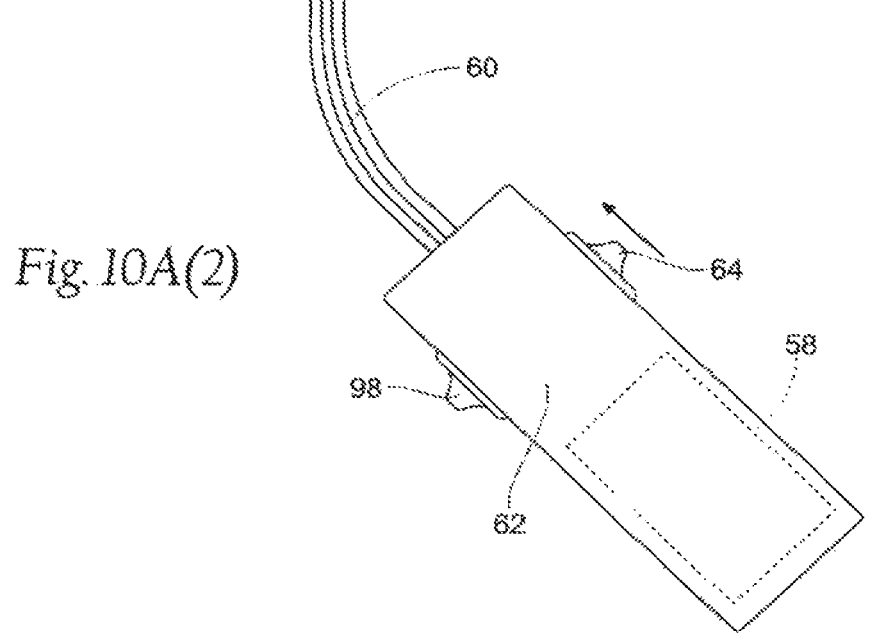
*Fig. 10A(2)*

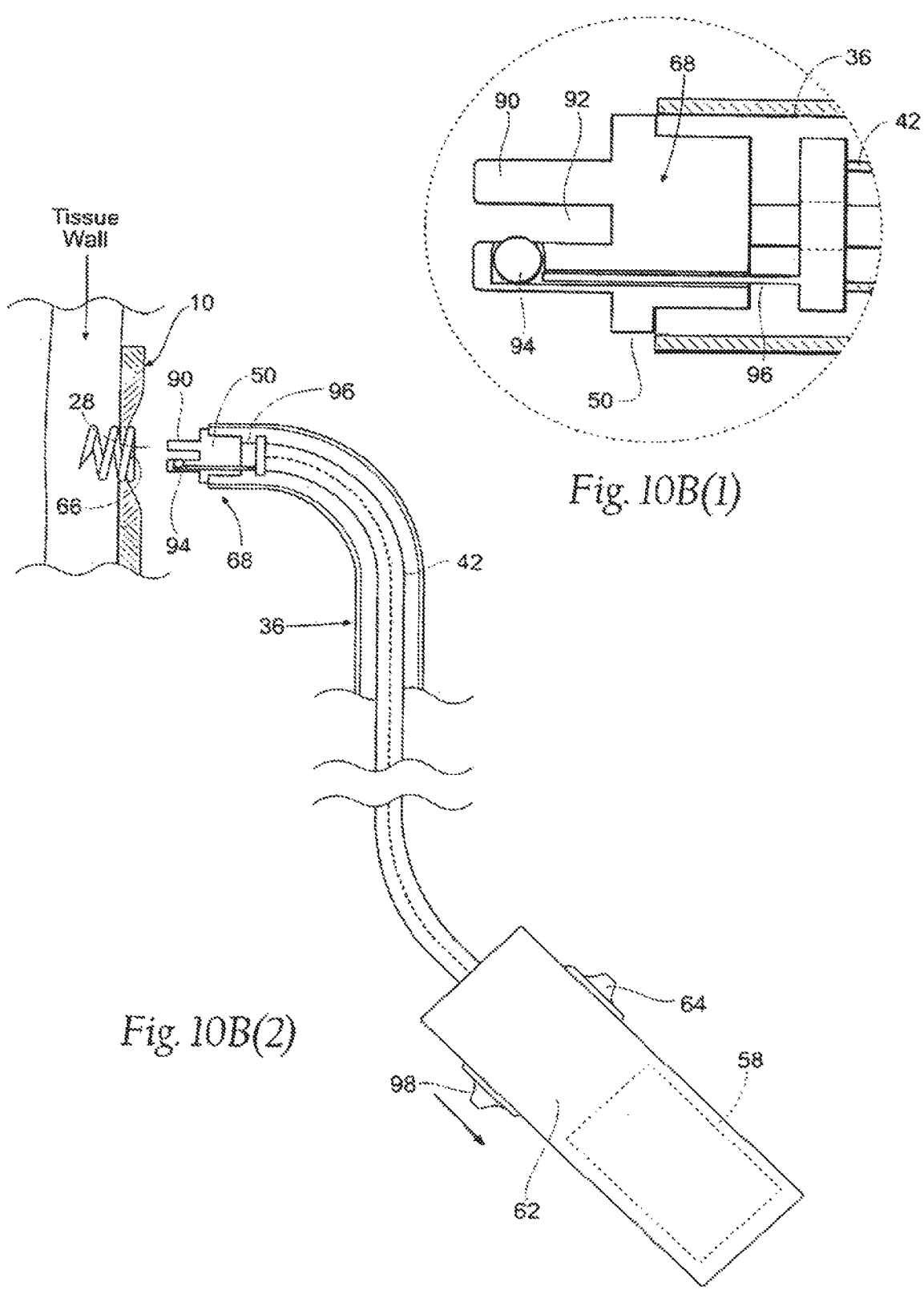
Fig. 10B(1)
Fig. 10B(2)

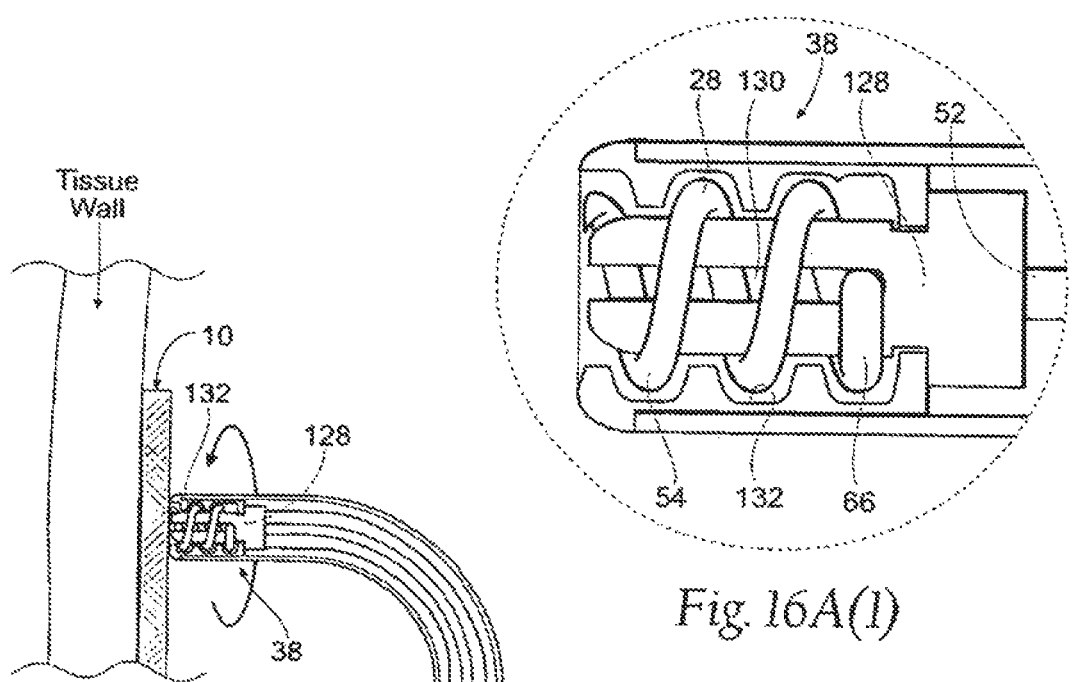
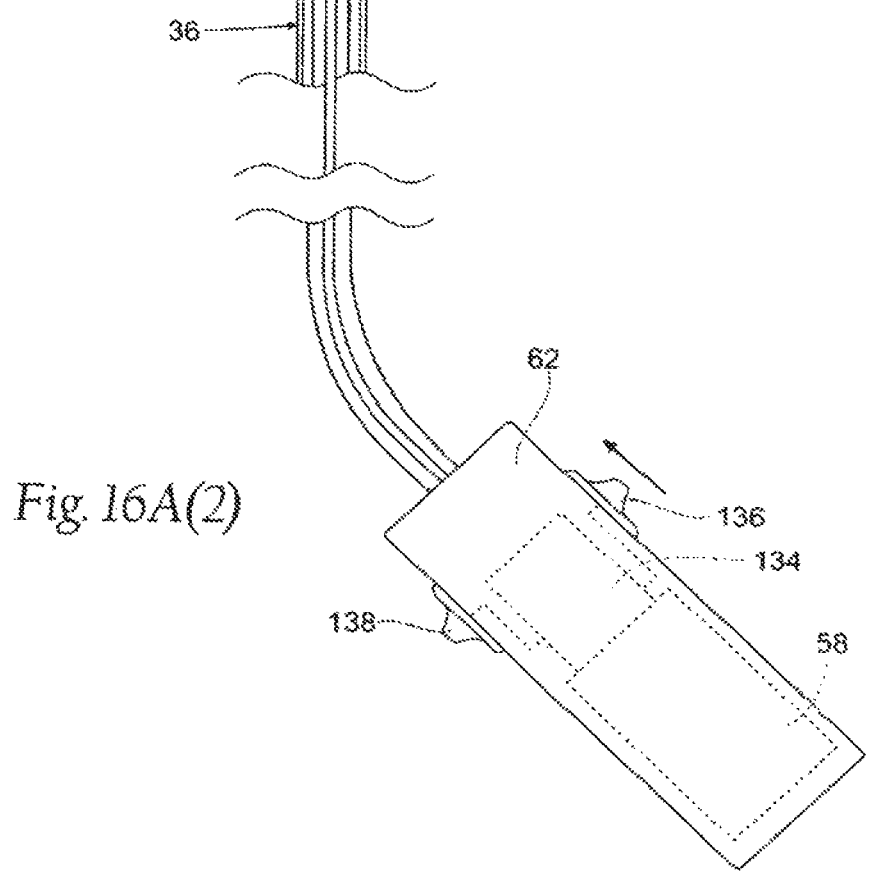
Fig. 16A(1)
Fig. 16A(2)

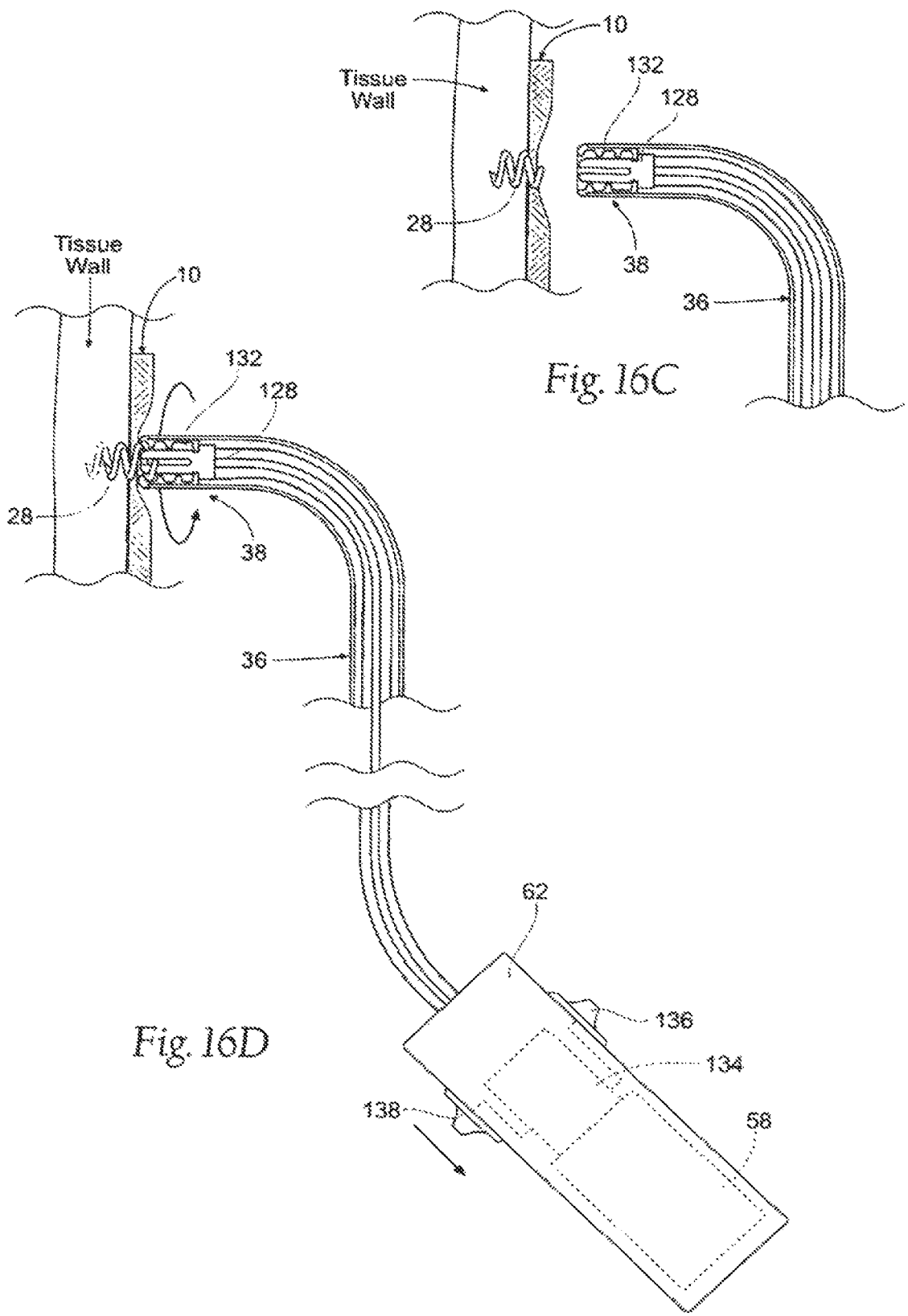

SYSTEMS AND METHODS FOR ATTACHING A PROSTHESIS WITHIN A BODY LUMEN OR HOLLOW ORGAN

RELATED APPLICATIONS

This application is a Division of and claims the benefit of U.S. patent application Ser. No. 14/210,683, filed Mar. 14, 2014, now allowed, which is a Continuation of U.S. patent application Ser. No. 13/495,836, filed Jun. 13, 2012, now U.S. Pat. No. 8,685,044 which is a Continuation of U.S. patent application Ser. No. 10/786,465, filed Feb. 25, 2004, now U.S. Pat. No. 8,231,639, which is a Continuation-in-Part of U.S. patent application Ser. No. 10/693,255, filed Oct. 24, 2003, now U.S. Pat. No. 6,929,661, which claims the benefit of U.S. Provisional Patent Application Ser. No. 60/489,011, filed Jul. 21, 2003. U.S. patent application Ser. No. 10/786,465 now issued as U.S. Pat. No. 8,231,639, is also a Continuation-in-Part of U.S. patent application Ser. No. 10/307,226, filed Nov. 29, 2002, now issued as U.S. Pat. No. 8,075,570, which is a Continuation-in-Part of U.S. patent application Ser. No. 10/271,334, filed Oct. 15, 2002, now issued as U.S. Pat. No. 6,960,217, which claims the benefit of U.S. Provisional Patent Application Ser. No. 60/333,937, filed Nov. 28, 2001. The disclosures of which are herein incorporated by reference in their entirety.

FIELD OF INVENTION

The invention relates generally to prostheses, and in particular, the attachment of prostheses used in the repair of diseased and/or damaged sections of a hollow body organ and/or a blood vessel.

BACKGROUND OF THE INVENTION

The weakening of a vessel wall from damage or disease can lead to vessel dilatation and the formation of an aneurysm. Left untreated, an aneurysm can grow in size and may eventually rupture.

For example, aneurysms of the aorta primarily occur in abdominal region, usually in the intrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic graft, made either in a straight of bifurcated configuration, is installed and then permanently attached and sealed to the ends of the native vessel by suture. The prosthetic grafts for these procedures are usually unsupported woven tubes and are typically made from polyester, ePTFE or other suitable materials. The grafts are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co-morbidities.

Endovascular aneurysm repair has been introduced to overcome the problems associated with open surgical repair. The aneurysm is bridged with a vascular prosthesis, which is placed intraluminally. Typically these prosthetic grafts for aortic aneurysms are delivered collapsed on a catheter through the femoral artery. These grafts are usually designed with a fabric material attached to a metallic scaffolding (stent) structure which expands or is expanded to contact the internal diameter of the vessel. Unlike open surgical aneurysm repair, intraluminally deployed grafts are not sutured to the native vessel, but rely on either barbs extending from the stent, which penetrate into the native vessel during deployment, or the radial expansion force of the stent itself is utilized to hold the graft in position. These graft attachment means do not provide the same level of attachment when compared to suture and can damage the native vessel upon deployment.

SUMMARY OF THE INVENTION

The invention provides apparatus, tools, systems, and methods for repairing diseased and/or damaged sections of a hollow body organ and/or a blood vessel. The apparatus, tools, systems, and methods find use, e.g., in the introduction and deployment of a prosthesis into a blood vessel or hollow body organ, which desirably is achieved by intra-vascular access. The prosthesis is secured in place by fasteners, which are implanted by the apparatus, tools, systems, and methods that embody one or more features of the invention, which are also desirably deployed by intra-vascular access.

According to one aspect of the invention, the applier is configured to permit controlled, selective release of the fastener in a step that is independent of the step of implantation. According to one embodiment of this aspect of the invention, the applier includes a driven member that is carried on a tool body. The tool body can include, e.g., a tube, such as a catheter, to permit intra-vascular deployment of the driven member. The driven member is operable to apply an implantation force to the fastener. A drive actuator operates the driven member. The applier also includes a fastener-engaging mechanism on the driven member. The mechanism is operable in a first condition to couple the fastener to the driven member to transfer the implantation force from the driven member to the fastener. Implantation of the fastener can thereby be achieved. The mechanism is also operable in a second condition to release the fastener from the driven member. According to this aspect of the invention, the mechanism includes a second actuator, which places the mechanism in the second condition, to release the fastener. The second actuator is operable independent of the drive actuator. There can thus be a definite, stepwise separation between implanting the fastener in tissue using the implantation tool and releasing the fastener from the implantation tool after implantation is satisfactorily achieved.

Another aspect of the invention provides a tool that can be used to apply an implantation force to a fastener, which is sized and configured for implantation in tissue in response to an implantation force applied according to prescribed conditions. The tool is coupled to a controller, which interrupts implantation before it is completed, and interjects a "go"/"no go" decision-making step before proceeding further. The tool includes a driven member carried on a tool body. The tool body can comprise, e.g., a tube, such as a catheter. The driven member is operable to apply the implantation force. A mechanism on the driven member couples the fastener to the driven member to transfer the implantation force from the driven member to the fastener. According to this aspect of the invention, a controller is coupled to the driven member. The controller executes differing operational phases during the implantation process. During an initial phase the driven member is operated to apply the implantation force under conditions that do not achieve the prescribed conditions, so that only partial implantation of the fastener occurs. A lull phase commences at the end of the initial phase. The lull phase interrupts operation of the driven member. There is a final phase, which operates the driven member under conditions that supplement the conditions of the initial phase to achieve the prescribed conditions, and thus achieve complete implantation. However, the controller requires, after the initial phase, a prescribed command to advance from the lull phase to the final phase. The lull phase requires a decision be made before implantation of the fastener is finalized. If implantation during the initial phase is deemed not to be satisfactory, implantation can be aborted, and the fastener (now only partially implanted) can be withdrawn. The decision can comprise a conscious decision by the operator and/or a decision based, at least in part, upon physical or operational conditions sensed during the initial phase.

Another aspect of the invention provides a tool for applying an implantation force to a fastener that is sized and configured for implantation in tissue in response to an implantation force. The tool comprises a driven member carried on a tool body that is operable to apply the implantation force. According to this aspect of the invention, an element is included that tethers the fastener to the tool body. The tethering element safeguards against inadvertent loss of the fastener prior to implantation. The tethering element includes a frangible portion, so that, once the fastener is satisfactorily implanted, the tethering element can be parted from the fastener and the tool body removed.

The invention also provides various systems and methods for using the above-described devices to implant tissue in a vessel or hollow body organ.

Other features and advantages of the invention shall be apparent based upon the accompanying description, drawings, and claims.

BRIEF DESCRIPTION OF THE DRAWINGS

The invention will be understood from the following detailed description of preferred embodiments, taken in conjunction with the accompanying drawings, wherein:

FIG. 1 is a perspective view of a prosthesis having a fastening region that accommodate s the introduction of one or more fasteners.

FIG. 2 is a perspective view of the prosthesis shown in FIG. 1, showing the attachment of fasteners in the fastening region.

FIG. 6 is a side view, partly broken away and in section, of an intra-vascular fastener applier that can be used to implant fasteners in the prosthesis shown in FIGS. 1 and 2, in the manner shown in FIG. 5.

FIG. 7 is a perspective view of a type of helical fastener that can be implanted using the intra-vascular fastener applier shown in FIG. 6.

FIG. 8A(1) is an enlarged view of a carrier for implanting a fastener of the type shown in FIG. 7, the carrier being located at the distal end of an intra-vascular fastener applier of the type shown in FIG. 8A(2), the carrier being shown in a condition to receive a fastener prior to implantation.

FIG. 8A(2) is a side view, partly broken away and in section, of a fastener applier that includes, at its distal end, a carrier as shown in FIG. 8A(1), the carrier being shown after receipt of a fastener and as the carrier is being rotated to implant the fastener in a prosthesis/tissue wall.

FIG. 8B(1) is an enlarged view of the carrier shown in FIG. 8A(1), the carrier being shown in a condition to release a fastener after implantation.

FIG. 8B(2) is a side view, partly broken away and in section, of the fastener applier that includes, at its distal end, the carrier shown in FIG. 8B(1), the carrier being shown releasing a fastener following its implantation in a prosthesis/tissue wall.

FIG. 8C is a side view, partly broken away and in section, of the fastener applier shown in FIG. 8A(2), the carrier being shown withdrawing or retrieving a fastener from a prosthesis/tissue wall.

FIG. 9A(1) is an enlarged view of another embodiment of a carrier from implanting a fastener of the type shown in FIG. 7, the carrier being located at the distal end of an intra-vascular fastener applier of the type shown in FIG. 9A(2), the carrier being shown in a condition to receive a fastener prior to implantation.

FIG. 9A(2) is a side view, partly broken away and in section, of a fastener applier that includes, at its distal end, a carrier as shown in FIG. 9A(1), the carrier being shown after receipt of a fastener and as the carrier is being rotated to implant the fastener in a prosthesis/tissue wall.

FIG. 9B(1) is an enlarged view of the carrier shown in FIG. 9A(1), the carrier being shown in a condition to release a fastener after implantation.

FIG. 9B(2) is a side view, partly broken away and in section of the fastener applier that includes, at its distal end, the carrier shown in FIG. 9B(1), the carrier being shown releasing a fastener following its implantation in a prosthesis/tissue wall.

FIG. 10A(1) is an enlarged view of a carrier for implanting a fastener of the type shown in FIG. 7, the carrier being located at the distal end of an intra-vascular fastener applier of the type shown in FIG. 10A(2), the carrier being shown in a condition to receive a fastener prior to implantation.

FIG. 10A(2) is a side view, partly broken away and in section, of a fastener applier that includes, at its distal end, a carrier as shown in FIG. 10A(1), the carrier being shown after receipt of a fastener and as the carrier is being rotated to implant the fastener in a prosthesis/tissue wall.

FIG. 10B(1) is an enlarged view of the carrier shown in FIG. 10A(1), the carrier being shown in a condition to release a fastener after implantation.

FIG. 10B(2) is a side view, partly broken away and in section, of the fastener applier that includes, at its distal end, the carrier shown in FIG. 10B(1), the carrier being shown releasing a fastener following its implantation in a prosthesis/tissue wall.

FIG. 16A(1) is an enlarged view of a carrier for implanting a fastener of the type shown in FIG. 7, the carrier being located at the distal end of an intra-vascular fastener applier of the type shown in FIG. 16A(2), the carrier being shown holding a fastener prior to implantation.

FIG. 16A(2) is a side view, partly broken away and in section, of a fastener applier that includes, at its distal end, a carrier as shown in FIG. 16A(1), the carrier being rotated to implant the fastener in a prosthesis/tissue wall.

FIG. 16C is a side view, partly broken away and in section, of the fastener applier shown in FIG. 16A(2), the carrier being shown following the first operating phase and at the end of a second operating phase, during which the fastener has been fully implanted and released from the carrier into a prosthesis/tissue wall.

FIG. 16D is a side view, partly broken away and in section, of the fastener applier shown in FIG. 16A(2), the carrier being shown following the first operating phase and during another operating phase, during which the fastener is being withdrawn or retrieved from a prosthesis/tissue wall while still secured to the carrier.

DETAILED DESCRIPTION OF THE INVENTION

I. Prosthesis

A. Structure

Figure 3:
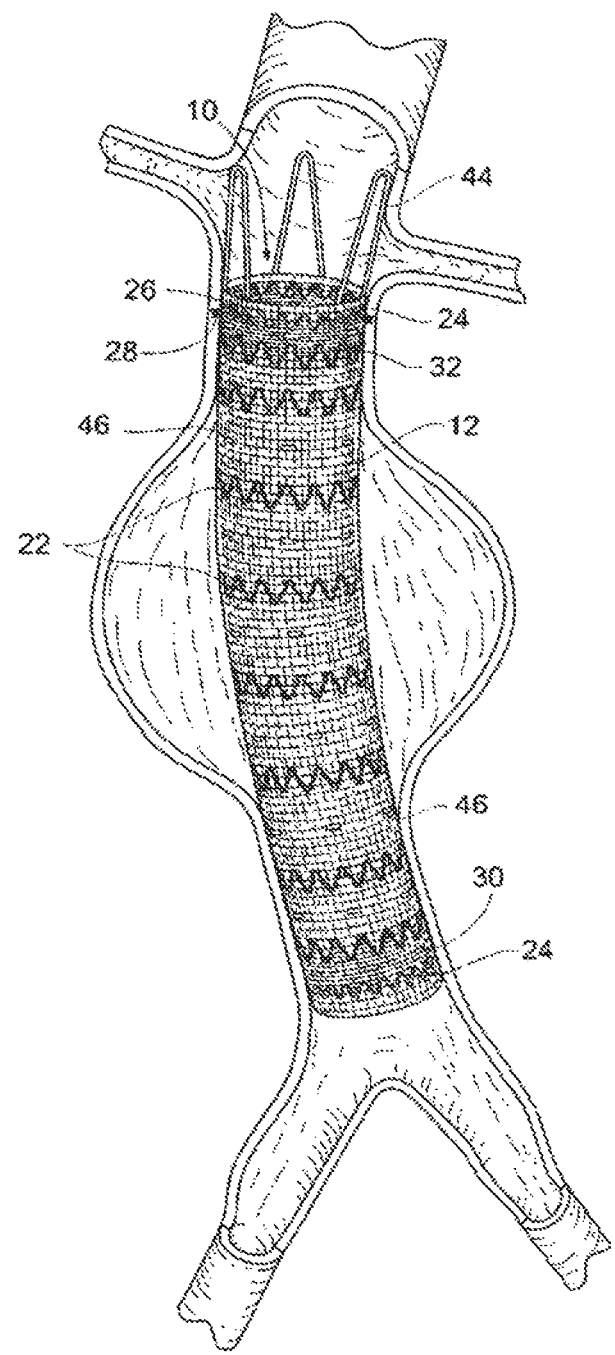
FIG. 3 is a perspective view of the prosthesis shown in FIG. 1 positioned within an abdominal aortic aneurysm.

FIG. 1 shows a prosthesis 10. The prosthesis 10 serves to repair or reinforce a region of a vessel wall or hollow body organ which has been weakened by disease or damage.

In the illustrated embodiment (see FIG. 1), the prosthesis 10 comprises a tubular trunk 12. The trunk 12 is sized and configured to fit within a targeted region of a hollow body organ and/or a blood vessel. The targeted region is selected on the basis of certain anatomic characteristics. These characteristics include a weakened conditioned caused, e.g., by disease or damage.

The trunk 12 forms a generally cylindrical structure with an open interior lumen 19. In the illustrated embodiment, the trunk 12 includes a prosthetic material 14 supported by a scaffold 16. The prosthetic material 14 is selected on the basis of its biocompatibility, durability, and flexible mechanical properties. The material 14 can comprise, e.g., woven polyester or ePTFE.

The scaffold 16 is desirable sized and configured to permit non-invasive deployment of the prosthesis 10 by an intra-vascular catheter. With this criteria in mind, the scaffold 16 is sized and configured to assume a compressed or collapsed, low profile condition, to permit its intra-vascular introduction into the hollow body organ and/or blood vessel by a catheter, as will be described in greater detail later.

Also with this criteria in mind, the scaffold 16 is sized and configured for expansion in situ from its collapsed condition into an expanded condition in contact with tissue in the targeted region, as will also be described in greater detail later.

In this respect, the scaffold 16 can comprise, e.g., a malleable plastic or metal material that expands in the presence of an applied force. In this arrangement, the deployment catheter can include, e.g., an expandable body, such as a balloon, to apply the expansion force to the scaffold 16 in situ.

Alternatively, the scaffold 16 can comprise a self-expanding plastic or metal material that can be compressed in the presence of a force, but self-expands upon removal of the compressive force. In this arrangement, the deployment catheter can include, e.g., a sleeve that can be manipulated to enclosed the scaffold 16 in a collapsed condition, thereby applying the compressive force, and to release the scaffold 16 when desired to allow the scaffold 16 to self-expand in situ.

For self-expansion, the scaffold 16 can include individual self-expanding, zigzag type main stent rings 22. The main stent rings 22 can be made, e.g., from Nitinol® wire. Still, other materials, manufacturing methods and designs can be used.

The main stent rings 22 need not be attached to one another throughout the prosthesis material 14, as FIG. 1 shows. The individual main stent rings 22 allow for longitudinal compliance while maintaining radial support of the open interior lumen 18. This technical feature allows the prosthesis 10 to more readily accommodate changes in morphology in the targeted region. Still, it may be desirable in certain locations within the prosthesis structure to have attachments between the individual main stent rings 22 to provide enhanced stability and/or additional radial support.

Each of the main stent rings 22 can be, e.g., sewn onto prosthetic material 14. In the illustrated embodiment, in which the prosthetic material 14 is woven polyester, the attachment of the main stent rings 22 can be made, e.g., with polyester suture.

However, it is also contemplated that other attachment means could be utilized to secure the main stent rings 22 to the prosthetic material 14. These means include bonding; capturing the main stent rings 22 between two layers of prosthetic material 14; and incorporating the main stent rings 22 directly into the prosthetic material 14.

In certain locations, it is desired to have the main stent rings 22 attached to the outer diameter of the prosthetic material 14. Still, it is also contemplated that the main stent rings 22 could be attached to the inner diameter of the prosthetic material 22.

At least one end of the trunk 12 desirably also includes one or more end stent rings 24. The principal purpose of an end stent ring 24 is to provide a seal between the trunk 12 and adjoining tissue. This sealing function is particularly desirable when the prosthesis 10 is deployed in a blood vessel or other body organ, where body fluids are intended to reside or pass through the prosthesis 10. The end sent rings 24 can also serve, with the main stent rings 22, to help maintain the position of the prosthesis 10 in the targeted region.

The trunk 12 (material 14 and/or scaffold 16) can carry radiopaque markers 46 to help fluoroscopically position the prosthesis 10. The markers 46 can take the form, e.g., of marker bands, tight wound coils, or wire made from radiopaque material such as platinum, platinum/iridium, or gold.

The trunk 12 also desirably includes at least on fastening region 26 that accommodates the introduction of one or more fasteners 28 to anchor the prosthesis 10 in place (see FIG. 2). It is desirable that this region 26 of the trunk 12 be specially sized and configured for the receipt and retention of fasteners 28. For example, the size and spacing of ring stent patterns can be configured in the region 26 to specially accommodate the placement of fasteners; and/or woven fibers with an "X-pattern" or a "sinusoidal pattern" can be used in the region 26 to specially accommodate placement of fasteners; and/or the prosthetic material 14 can be folded-over to form multiple layers, to reinforce the prosthesis in the region 26 where fasteners are placed; and/or denser weave patterns or stronger fibers can be used, selected from, e.g., Kevlar™ material or Vectran™ material or metallic wire woven alone or interwoven with typical polyester fibers in the region 26 were fasteners are placed. It may also be desirable to fluoroscopically indicated this region 26 with auxiliary radiopaque markers 30 on the prosthetic material 14, and/or auxiliary stent rings 32 to aid in positioning the fasteners.

The fasteners 28 can be variously constructed. They can, e.g., comprise helical fasteners or staples.

Desirably, like the prosthesis 10 itself, the fasteners 28 are introduced by an intra-vascular fastener attachment assembly. Details of various fastener attachment assemblies will be described in greater detail later.

B. Use of the Prosthesis

The targeted region for deployment of the tissue reinforcement prosthesis 10 as just described can vary. In FIG. 3, the trunk 12 is sized and configured to extend, for purposes of illustration, in the aorta adjacent the renal arteries distally to a location proximal the natural bifurcation of the iliac arteries. However, this targeted site of deployment is selected for purposes of illustrating the features of the prosthesis 10, and it is not intended to be limiting.

As shown in FIG. 3, the fastening region 26 is located in the neck of the aorta adjacent to the renal arteries. The features of the fastening region 26, previously described, make possible the secure attachment of the prosthesis 10, without migration.

In this arrangement (see FIG. 3), the trunk 12 may include a supra-renal stent 44 at its proximal end, which extends beyond the prosthetic material 14. When deployed within the aorta, this stent 44 would extend above the level of the renal arteries, as FIG. 3 shows. The supra-renal stent 44 orients the prosthesis 10 within the lumen and aids in maintaining the position of the prosthesis 10 in the aorta without obstructing the normal blood flow into the renal arteries.

Figure 4:
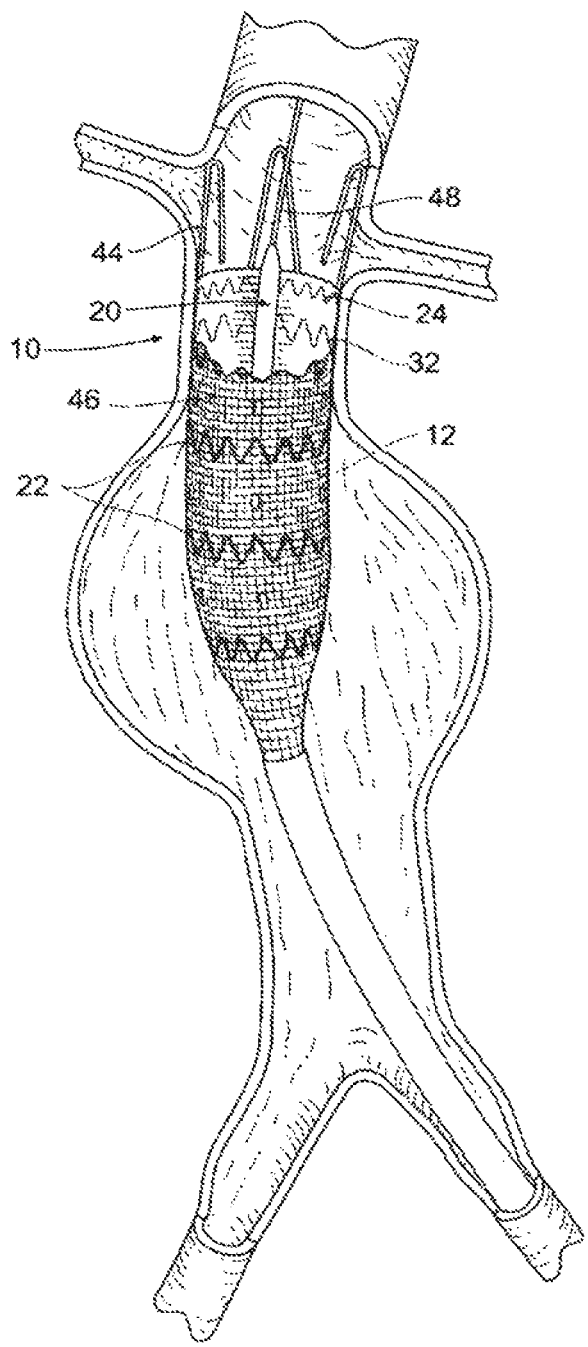
FIG. 4 is a perspective view of the prosthesis shown in FIG. 3 as it is being deployed by an intra-vascular catheter.

During use (see FIGS. 4 and 5), a first catheter 20 is navigated over a guide wire 48 through an iliac to the desired location within the aorta near the renal arteries. The catheter 20 carries the prosthesis 10 in a radially reduced configuration. At the targeted site, the catheter 20 releases the prosthesis 10, which expands radially into the position shown in FIG. 5.

A fastener assembly 34 is next deployed (which is shown generally in FIG. 5) to place fasteners 28 into the fastening region 26 of the trunk 12. The prosthesis 10 is thereby secured in position.

II. Prosthesis Attachment Systems and Methods

The fastener assembly 34 can be variously constructed and configured.

In an illustrated arrangement (see FIG. 6), the fastener attachment assembly 34 comprises a fastener guide component 36 and a fastener applier component 38. The guide component 36 can comprise, e.g., a guide sheath that desirably has a steerable or deflectable distal tip. The guide component 36 can be initially deployed over the guidewire that is used to deliver and position the prosthesis 10. The guide wire can be withdrawn after the guide component 36 is deployed and positioned, so that the applier component 38 can be introduced.

In this arrangement, the applier component 38 is desirably deployed through the guide component 36. A fastener drive mechanism 40 n the fastener applier component 38 carries at least one fastener 28. The fastener drive mechanism 40 advances the fastener 28, causing it to penetrate the prosthesis 10 and underlying tissue wall. In this way, the fastener anchors the prosthesis 10 firmly in place.

In the illustrated embodiment (see FIG. 6), the fastener applier 38 comprises a catheter 42. The catheter 42 carries the fastener drive mechanism 40 at its distal tip.

The fastener drive mechanism 40 comprises carrier 50. The carrier 50 is sized and configured to carry a selected fastener 28. The fastener drive mechanism 40 also includes a driver 52, which is coupled to impart movement to the carrier 50. The driver 52 and carrier 50 can comprise an integrated unit, with the carrier 50 being formed on the distal end of the driver 52, as shown, or they can comprise separate components, e.g., with the driver comprising a clutch or the like for the carrier 50. The driven movement deploys the fastener 28. The type of driven movement that is imparted depends upon the type of fastener 28 that is used.

In the illustrated embodiment (see FIG. 7) the fastener 28 comprises is an open helical coil 54 with a sharpened leading tip 56. This type of helical fastener is deployed into tissue by rotational movement. Consequently, rotational movement is imparted by the driver 52 to the carrier 50, which is sized and configured to carry the fastener shown in FIG. 7.

The actuation of the driver 52 can, of course, be accomplished in various ways, e.g., mechanical (i.e., manual or hand-powered), electrical, hydraulic, or pneumatic.

In the illustrated embodiment (see FIG. 6), a drive motor 58 imparts rotation to the driver 52 through a drive cable 60. In the illustrated embodiment (FIG. 6), the drive motor 58 is housed in a handle 62, which is carried at the proximal end of the catheter 42. The drive cable 60 extends from the handle 62, through the catheter 42, and couples to the driver 52 at the distal end of the catheter 42. The drive cable 60 is desirably made of a suitable material that allows for both bending and rotation.

Activation of the drive motor 58 (e.g., by a physician controlled switch 64 on the handle 62) rotates, as a unit, the drive shaft 60, the driver 52, the carrier 50, and the fastener 28 in the carrier 50. The rotational movement causes the helical fastener 28 to travel into the prosthesis 10 and the tissue wall.

The implantation force of the fastener drive mechanism 40 is desirably resolved in some manner to provide positional stability and resist unintended movement of the carrier 50 relative to the implantation site. A resolution force is desirably applied to counteract and/or oppose the implantation force of the fastener drive mechanism 40. It is desirable to resolve some or all or a substantial portion of the implantation force within the vessel lumen (or other hollow body organ) itself, and preferably as close to the implantation site as possible.

Figure 5:
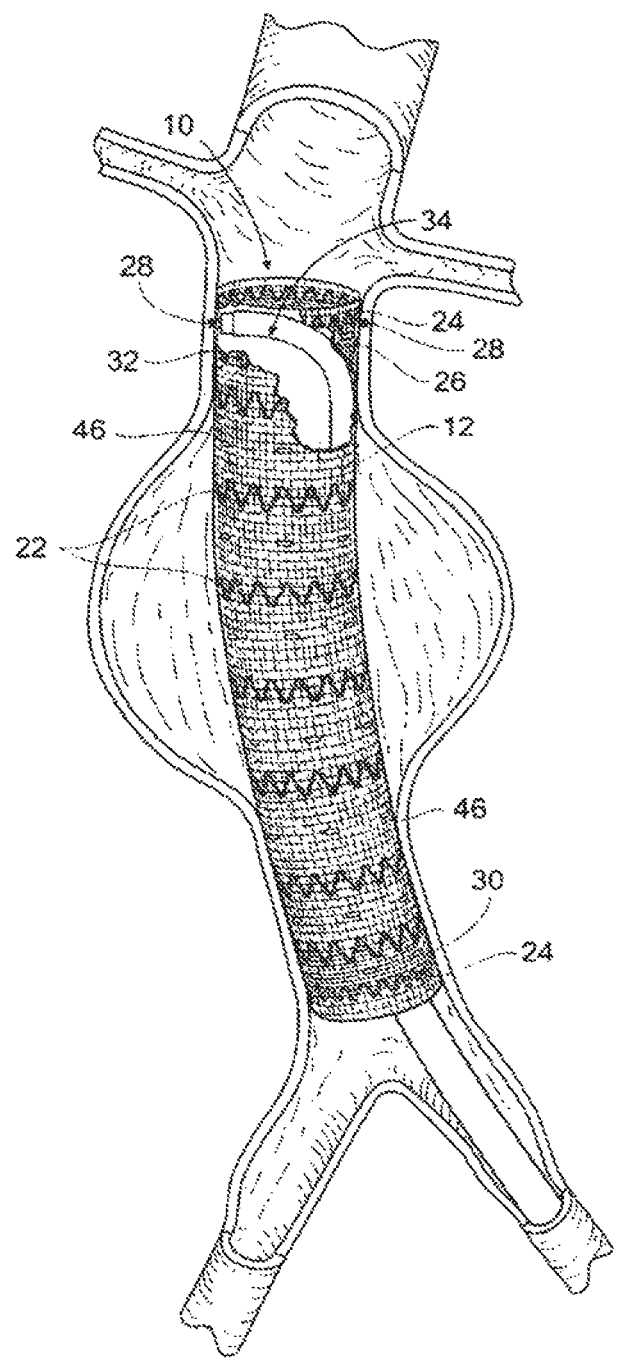
FIG. 5 is a perspective view of the prosthesis shown in FIG. 3 after it been deployed and as fasteners are being implanted by an intra-vascular fastener applier.

The tubular body of the guide component 36 and/or the shaft of the catheter 42 can be sized and configured to possess sufficient column strength to resolve some or all or at least a portion of the implantation force within the vessel lumen or hollow body organ. FIG. 5 shows the guide component 36 braced against the vessel wall to apply a counterbalancing resolution force. In addition, or alternatively, the guide component 36 and/or the fastener applier component 38 can include some form of stabilization means for applying a counteractive force at or near the carrier 50. Various types of stabilization means are disclosed in co-pending U.S. patent application Ser. No. 10/669,881, filed Sep. 24, 2003, and entitled "Catheter-Based Fastener Implantation Apparatus and Methods with Implantation Force Resolution."

The carrier 50 itself can be carious constructed, as can the fastener 28 to facilitate its coupling to the carrier 50. Representative embodiments will now be described.

A. Carriers with Independent Fastener Release Mechanisms

1. Carriers with Fastener Support Elements Having Release Mechanisms

The proximal end of the fastener 28 desirably includes a fitting 66 that, in use, couples the fastener 28 to the carrier 50. In one illustrated embodiment (see FIG. 7), the fitting 66 comprises an L-shaped brace or leg 66. The L-shape leg 66 desirably bisects the entire interior diameter of the coil 54; that is, the L-shaped leg 66 extends completely across the interior diameter of the coil 54, as FIG. 7 shows.

In this arrangement, the carrier 50 is sized and configured to engage the fitting 66, i.e., L-shaped leg 66, to thereby impart rotation to the helical fastener 28 to achieve implantation. The L-shaped leg 66 also serves as a stop to prevent the helical fastener 28 from penetrating too far into the tissue.

In one illustrated embodiment, the carrier 50 (see FIGS. 8A(1) and 8A(2)) includes a fastener support element 68 that permits the selective release of the fastener 28. The support element 68 has at least two operating conditions.

In a first condition (see FIG. 8A(1)), the support element 68 engages the L-shaped leg 66 of the fastener 28 to hold the fastener 28 on the carrier 50. In the first condition, rotation of the carrier 50 imparts rotation to the fastener 28 (as shown by the rotational arrow in FIG. 8A(2), to allow implantation of the fastener 28 into the prosthesis 10/tissues wall without releasing the fastener 28 (i.e., in response to rotation in one direction, as FIG. 8A(2) shows), as well as allow the withdrawal the fastener 28 from the prosthesis 10/tissue wall without releasing the fastener 28 (i.e., in response to rotation in an opposite direction, as FIG. 8C shows).

In a second condition (see FIGS. 8B(1) and 8(B)(2)), the support element 68 releases the fastener 28. In the second condition, the fastener 28 and the carrier 50 can be separated. Release of the fastener 28 from the carrier 50 can be and desirably is accomplished without rotation of the carrier 50. It is desirable that the support element 68 can affect separation of the fastener 28 while the carrier 50 is stationary and not rotating.

The support element 68 therefore differentiates the step of operating the carrier 50 to implant the fastener 28 (by rotation of the carrier 59 with the support element 68 in its first condition) from the step of releasing the fastener 28 from the carrier 50 (by placing the support element 68 in its second condition, which is desirably achieved independent of rotation of the carrier 50). The support element 68 thereby also makes possible the use of the carrier 50 to withdrawn the fastener 28 from tissue and to retrieve or reposition the fastener 28, if desired. Operation of the support element 68 independent of operation of the carrier 50 makes possible the release of the fastener 28 from the carrier 50 in a separate releasing step, which can be delayed to assure that implantation of the fastener 28 has been satisfactorily completed.

The features of the support element 68 just described can be achieved by the use of various structural embodiments. In the embodiment shown in FIGS. 8A(1) and 8B(1), for example, the support element takes the form of hinged gripping jaws 70 on the distal end of the carrier 50. The gripping jaws 70 are moveable between a mutually closed condition (i.e., the first condition, as shown in FIG. 8A(1))

and a mutually opened condition (i.e., the second condition, as shown in FIG. 8B(1)). The L-shaped leg 66 of the fastener 28 is gripped by interference fit within a receptacle 72 formed between the jaws 70 when the jaws 70 are mutually closed, as FIGS. 8A(1) and 8A(2) show. The receptacle 72 opens and frees the L-shaped leg 66 when the gripping jaws 70 are mutually opened, as FIGS. 8B(1) and 8B(2) show.

In this embodiment, a physician-manipulated actuator 74 selectively pivots the hinged gripping jaws 70 from their mutually closed condition to their mutually opened condition. In the illustrated embodiment (see FIGS. 8A(1) and 8B(1)), the actuator 74 comprises a pull cable 76 or stylet, which is coupled at its proximal end to a controller 78 on the handle (see FIGS. 8A(2) and 8B(2)). The pull cable 76 extends through the catheter 42 and terminates at its distal end with a shaped cam element 78. The cam element 78 in the illustrated embodiment is ball-shaped. It occupies the area defined between tapered, facing cam surfaces 80 formed on the interior of the gripping jaws 70, when the jaws 70 are mutually closed (FIG. 8A(1)), the cam element 78 rests in the region of greatest distance between cam surfaces 80, adjacent the distal end of the gripping jaws 70. In this arrangement, when the physician manipulates the controller 78 to pull the cable 76 in an aft direction (i.e., toward the handle 62) (FIG. 8B), the cam element 78 travels on the tapered cam surfaces 80 toward the region of least distance between the surface 80. As it moves, the cam element 78 applies force against the cam surfaces 80 to pivot the jaws 70 open, i.e., moving them from the mutually closed to the mutually opened condition, as FIG. 8B(1) shows.

In the illustrated embodiment, the hinged gripping jaws 70 are desirably biased toward the mutually closed condition. A spring can be used for the purpose. Desirably, the gripping jaws 70 are formed by machining or molding from an elastic, spring-like material (metal or plastic). The formed material includes an integral hinge 82, which normally biases the gripping jaws 70 closed. The hinge 82 yields to the force applied by the cam element 78 against the cam surfaces 80, but returns the jaws 70 to their mutually closed condition in the absence of the force. In this arrangement (see FIG. 8A(1)), a physician can snap fit the L-shaped leg 66 of a fastener 28 into the receptacle 72 between the gripping jaws 70 at time of use. The snap fir provides tactile assurance that the fastener 28 has been properly engaged within the receptacle 72 of the gripping jaws 70.

In an alternative embodiment (see FIGS. 9A(1) and 9B(1)), the support element 68 takes the form of spring-biased struts 84 on the carrier 50. The struts 84 resiliently open to accommodate snap-fit passage of the L-shaped leg 66 into a retaining space 87 between the struts 84, allowing the coil 54 of the fastener 28 to nest upon the struts 84 (as FIG. 9A(2) shows). The resilient, normally closed condition of the struts 84 comprise the first operating condition, which holds the fastener 28 on the struts 84, thereby securing the fastener 28 to the carrier 50. In this condition, rotation of the carrier 50 rotates the fastener 28, to allow implantation of the fastener 28 into tissue and/or withdrawal of the fastener 28 from tissue.

In this arrangement, a physician-manipulated actuator comprising, e.g., a push cable or stylet, can be advanced forward through the catheter by operation of a controller 88 on the handle 62. The carrier 50 need not be and desirably is not rotated during this operation. The push cable 86, when advanced (see FIGS. 8B(1) and 8B(2)), contacts the L-shaped leg 66 and urges the leg 66 out of the retaining space 87 against the resiliently displaced by force of the L-shaped leg 66, which are caused to assume a temporary, mutually opened condition. The fastener 28 can thereby be ejected from the carrier 50.

In an alternative arrangement (see FIGS. 10A(1) and 10B(2)), the support element 68 may include normally open struts 90 that define a receptacle 92 and include a detent 94 that governs passage of the L-shaped leg 66 into and out of the receptacle 92. A physician-manipulated actuator 96 comprising, e.g., a push-pull cable or stylet, can be advanced fore and aft through the catheter 42 into and out of contact with the detent 94, e.g., by operation of a controller 98 on the handle 62 (see FIGS. 10A(2) and 10(13)(2)). The cable 96, when advanced into contact with detent 94 (see FIG. 10A(1)(1)) locks the detent 94 in a position projecting into the receptacle 92. The detent 94, when locked, blocks entry into or out of the receptacle 92. The cable 96, when withdrawn from contact with detent 94, unlocks the detent 94, and allows movement of the detent 94 out of the position blocking the receptacle 92.

The detent 94, when unlocked (see FIGS. 10A(1) and 10A(2)), accommodates passage of the L-shaped leg 66 into the retainer 92 between the struts 90, while the remainder of the fastener 28 nests upon the struts 90. The fastener 28 can be loaded onto the carrier 50 in this fashion. The subsequent locking of the detent 94 (see FIG. 10A(2)) blocks release of the L-shaped leg 66, securing the fastener 28 to the carrier 50. This corresponds to the above-described first operating condition. In this condition, rotation of the carrier 50 rotates the fastener 28 (as shown by the rotational arrow in FIG. 10A(2)), to allow implantation of the fastener 28 into the prosthesis 10/tissue wall and/or withdrawal of the fastener 28 from the prosthesis 10/tissue wall.

The cable 96, when advanced out of the contact with detent 94, unlocks the detent 94 (see FIGS. 10B(1) and 10B(2)). The carrier 50 need not be and desirable is not rotated during this operation. This allows passage of the L-shaped leg 66 past the detent 94 and free of the receptacle 92, as previously described, in response to aft movement of the catheter 42 and attached carrier 50.

Figure 11:
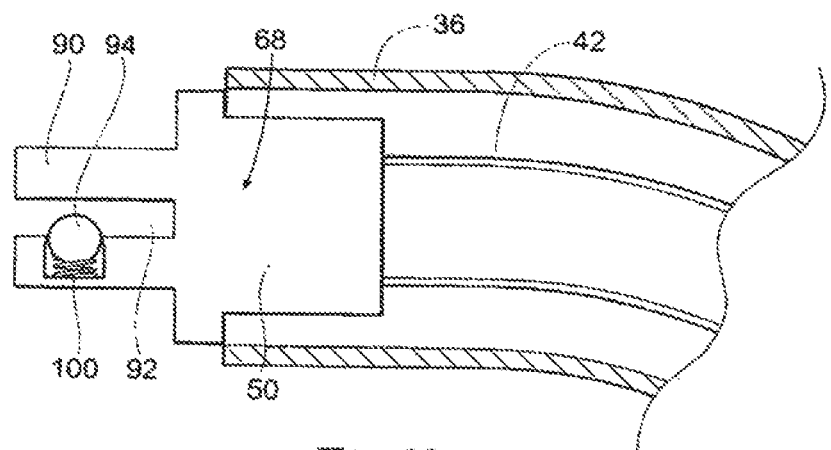
FIG. 11 is an enlarged view of a carrier for implanting a fastener of the type shown in FIG. 7, the carrier being located at the distal end of an intra-vascular fastener applier of the type shown in FIGS. 10A(2) and 106(2), the carrier being shown in a condition to receive a fastener prior to implantation.

Alternatively, as shown in FIG. 11, the detent 94 may be biased by a spring 100 toward a normally projecting condition to serve the same function.

2. Carrier with Releasable Fastener Cap Assemblies

Figures 12A, 12B:
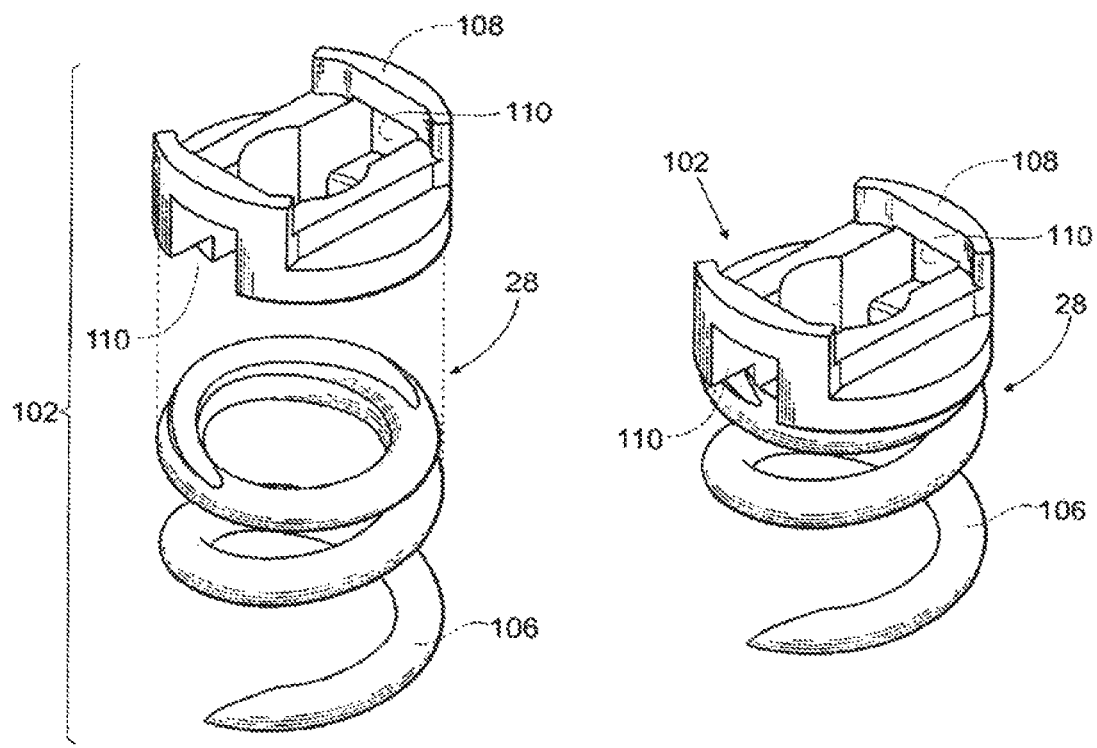
FIGS. 12A and 12B are perspective views of a fastener assembly comprising a helical fastener and a cap, FIG. 12A showing an exploded view of the assembly and FIG. 12B showing an assembled view of the assembly.

In another illustrated embodiment (sees FIGS. 12A and 12B), the fastener 28 takes the form of a fastener cap assembly 102 that is releasably fitted onto a specially adapted carrier 104 (see FIGS. 14A and 14B) at time of use. In the illustrated arrangement (see FIGS. 12A and 12B), the fastener cap assembly 102 includes a helical fastener 106 on which a proximal cap 108 is mounted. The cap 108 can comprise a plastic, metal, or ceramic biocompatible material. The cap 108 can be secured to the proximal end of the fastener 106, e.g., by adhesives, machining, molding, or welding. The cap 108 includes preformed side mounts 110. In this arrangement, the cap 108 serves the same general function as the L-shaped leg 66 shown in FIG. 7, i.e., it is a fitting secured to the fastener that enables the coupling of the fastener 28 to the carrier.

Figure 14A:
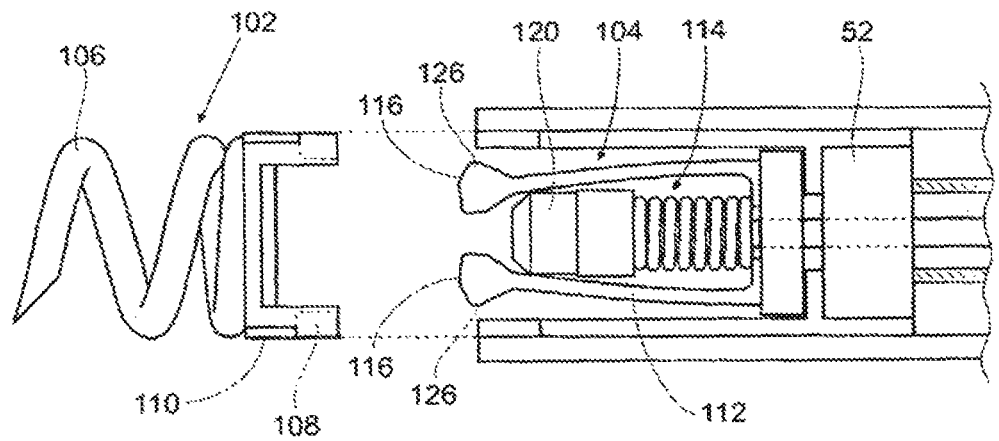
FIGS. 14A and 14B are side views showing the mounting of the fastener assembly shown in FIG. 12B to the carrier shown in FIG. 13A.

In this arrangement (see FIGS. 14A and 14B), the carrier 104 includes an attachment mechanism 112, which will be described in greater detail later. The attachment mechanism 112 is sized and configured to engage the mounts 110, to thereby couple the fastener assembly 102 to the carrier 104 at time of use. The attachment mechanism 112 imparts rotation to the fastener assembly 102 when the carrier 104 is rotated (see FIG. 15A) to achieve implantation of the fastener assembly 102 into the prosthesis 10/tissue wall without releasing the fastener assembly 102 (i.e., in response to rotation of the carrier 104 in one direction, as FIG. 15A shows). The attachment mechanism 112 can also withdraw the fastener assembly 102 from the prosthesis 10/tissue wall (see FIG. 15C) without releasing the fastener assembly 102 (i.e., in response to rotation of the carrier 104 in an opposite direction, as FIG. 15C shows).

Figure 15A:
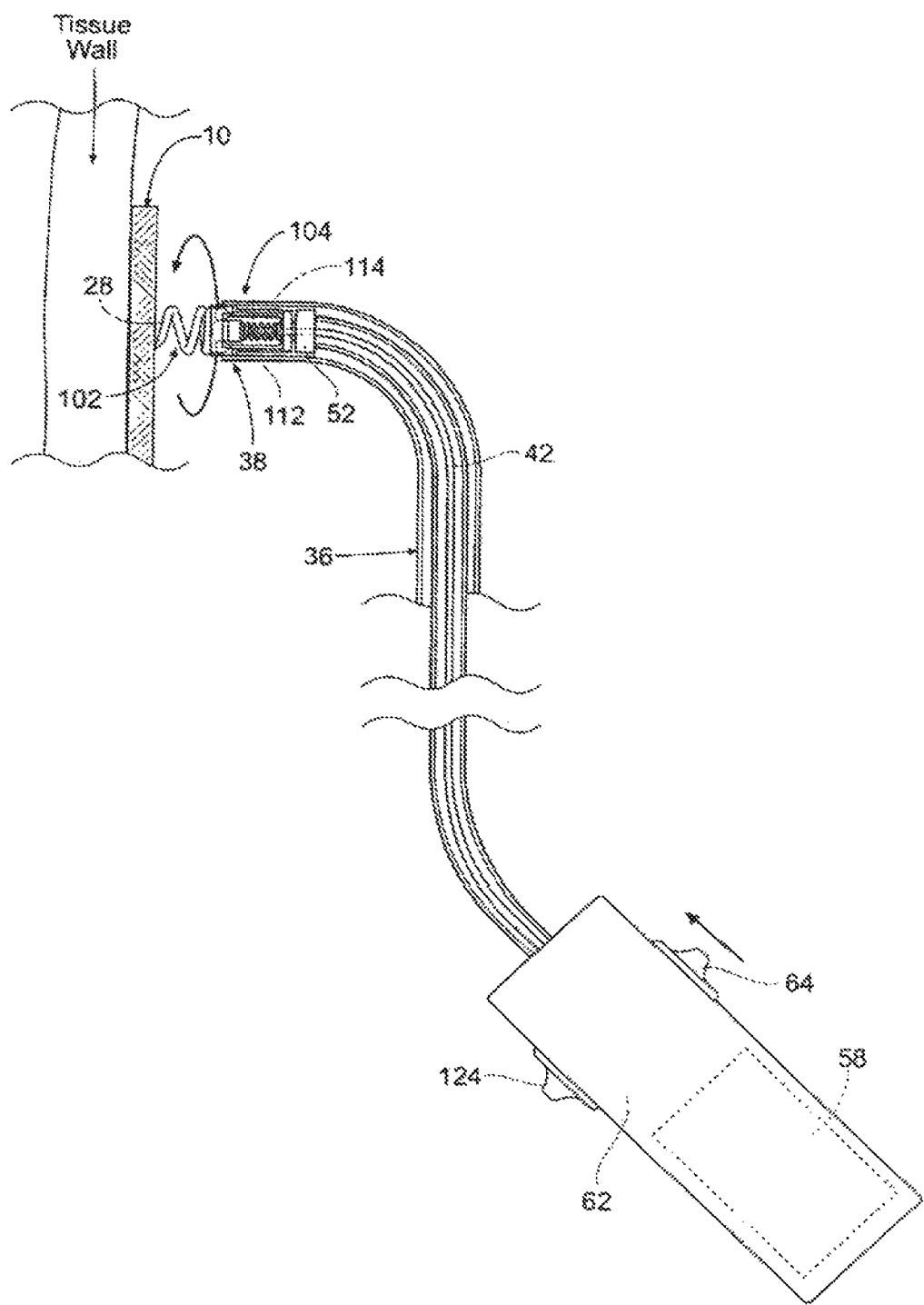
FIG. 15A is a side view, partly broken away and in section, of a fastener applier that includes, at its distal end, a carrier as shown in FIG. 13A, the carrier being shown after receipt of a fastener assembly as shown in FIG. 14B and as the carrier is being rotated to implant the fastener assembly in a prosthesis/tissue wall.
Figure 15B:
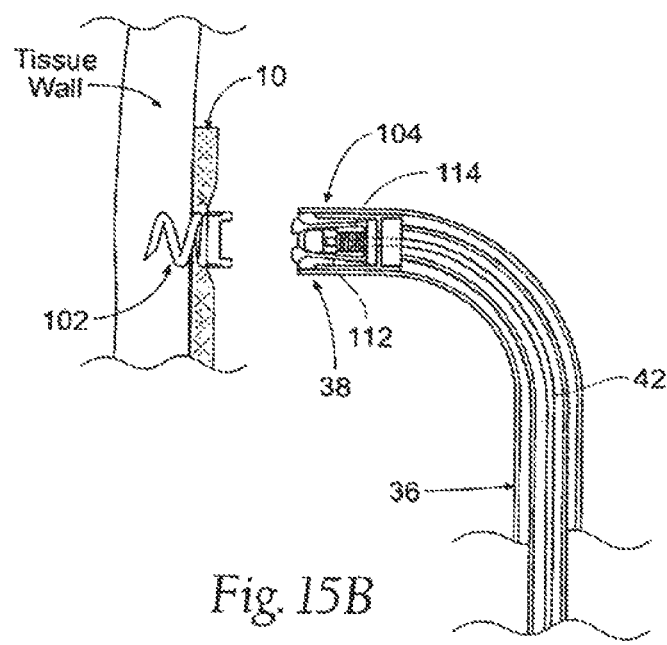
FIG. 15B is a side view, partly broken away and in section, of a fastener applier shown in FIG. 15A, the carrier being shown releasing the fastener assembly after its implantation in a prosthesis/tissue wall.

The carrier 104 also includes a release mechanism 114, as will be described in greater detail later. The release mechanism 114 selectively releases the fastener assembly 102 from the attachment mechanism 112 (see FIG. 15B). Release of the fastener assembly 102 from the attached mechanism 112 can be and desirably is accomplished without rotation of the carrier 104.

The carrier 104 with an attachment mechanism 112 to which a fastener assembly 102 can be fitted at time of use, as well as an independent, selectively operable release mechanism 114 allows a physician to operate the carrier 104 to implant the fastener assembly 102 separate from the step of releasing the fastener assembly 102 after implantation has been accomplished. The carrier 104 with a selective release for the fastener assembly 102 also makes possible the withdrawal the fastener assembly 102 from tissue and the retrieval and/or reposition the fastener assembly 104, if desired while the carrier 104 remains secured to the fastener assembly 102. In this arrangement, release of the fastener assembly 102 from the carrier 104 can be accomplished once fastener assembly 102 has been satisfactorily implanted, or otherwise at a time controlled by the operator.

The features of the carrier 104 as just described can be achieved by the use of various structural embodiments. In the embodiment shown in FIGS. 13A and 13B, the attached mechanism 1112 comprises a pair of gripper arms 116 coupled to the driver 52. The gripper arms 116 can be made by machining or molding from a metal or plastic material. The gripper arms 116 can be normally biased toward an inwardly deflected condition. The bias can be achieved, e.g., by imparting a spring memory to the arms 116. Alternatively, the arms 116 need not be biased inwardly, but instead include outside edges that are inclined, as FIG. 13B shows. The arms include outwardly projecting tabs 126 that are sized to snap into mounts 110 on the cap 108 (as FIG. 14B shows).

In this arrangement, the release mechanism 114 comprises a spacer rod 118 extends between the gripper arms 116. The rod 118 carries at its distal end a cam element 120. When withdrawn from contact with the gripper arms 116 (as FIG. 13B shows), the gripper arms 116 are positioned such that the tabs 126 will snap into the mounts 110 on the cap 108, see FIG. 14A shows. The cam element 120, when disposed in contact with the gripper arms 116 (as shown in FIG. 13A), spreads the gripper arms 116 (as shown in FIG. 13A), spreads the gripper arms 116 apart, into an outwardly deflected condition, locking the tabs 116 into the mounts 110, as FIG. 14B shows.

Figure 13A:
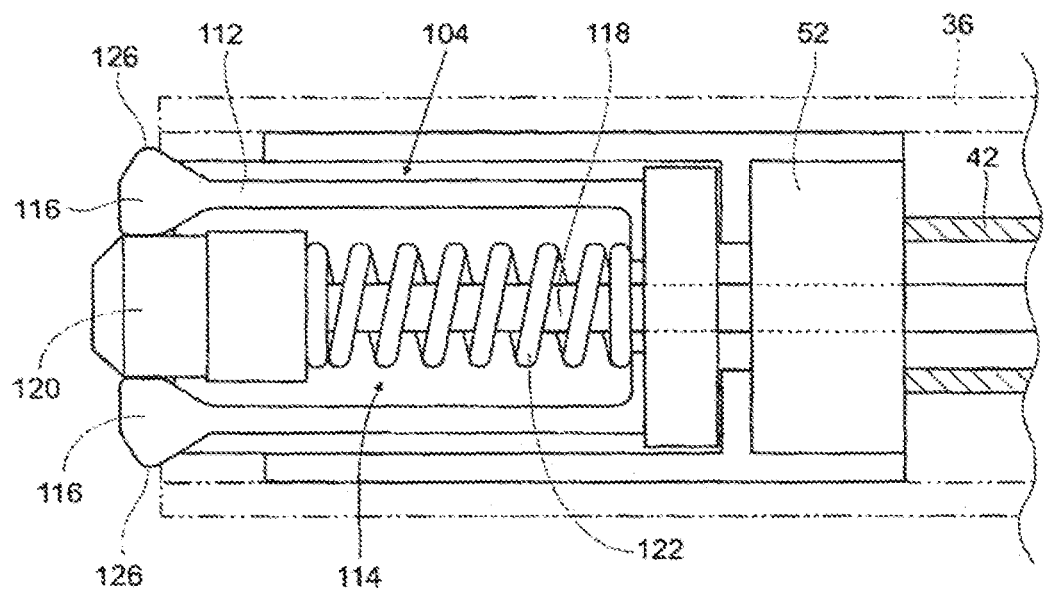
FIGS. 13A and 13B are side views showing in interior of a carrier for implanting a fastener assembly of the type shown in FIG. 12B, the carrier being located at the distal end of an intra-vascular fastener applier of the type shown in FIG. 15A, the carrier in FIG. 13A being shown in a condition to receive the fastener assembly prior to implantation, the carrier in FIG. 13B being shown in a condition to release the fastener assembly after implantation.
Figure 13B:
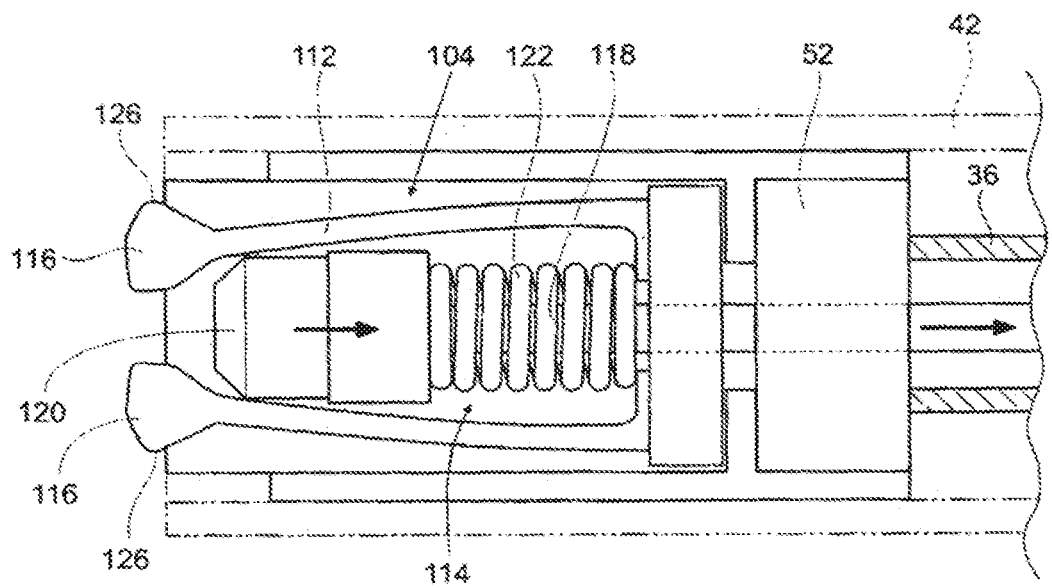
Figure 14B:
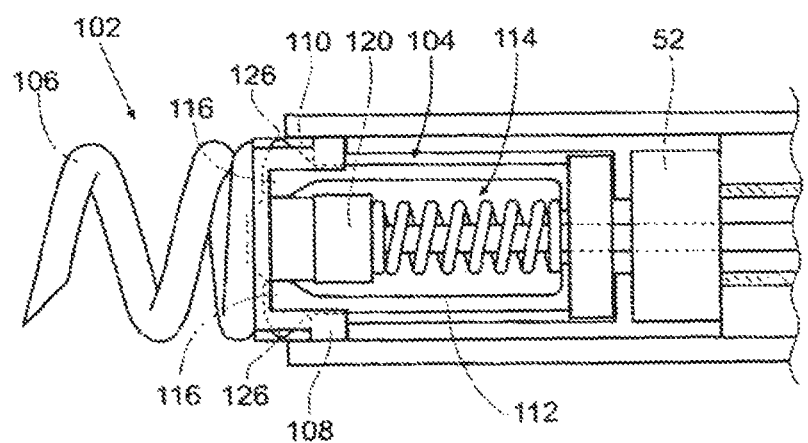
Figure 15C:
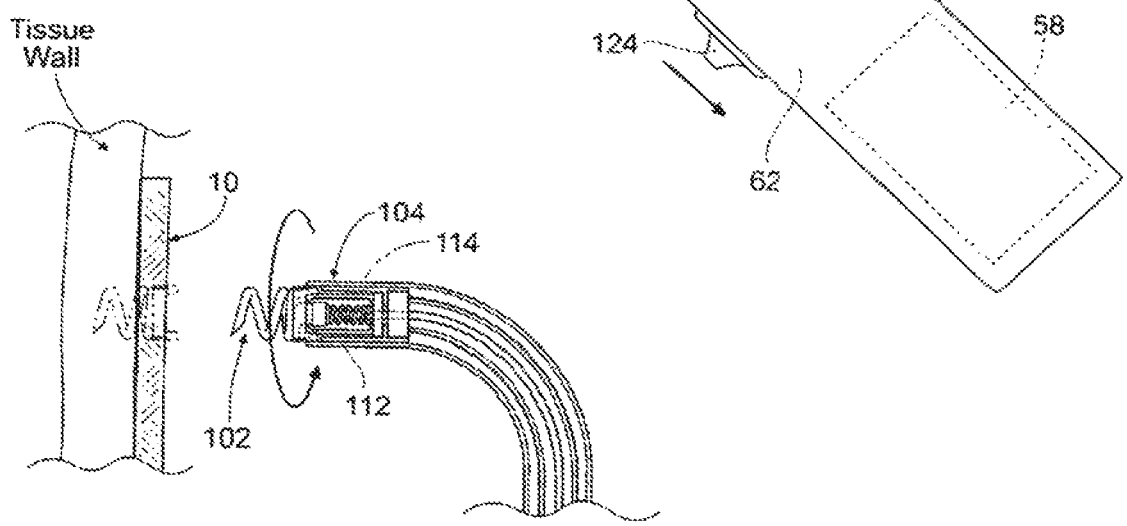
FIG. 15C is a side view, partly broken away and in section, of a fastener applier shown in FIG. 15A, the carrier being shown withdrawing or retrieving the fastener assembly from a prosthesis/tissue wall.

A spring 122 normally urges the cam element 120 toward contact with the gripper arms 116 (as shown in FIGS. 13A and 14B). The rod 118, when pulled aft (as FIGS. 13B and 14A show) withdraws the cam element 120, and the gripper arms 116 are positioned to receive the cap 108. The rod 118 extends through the catheter 42 and is coupled to a controller 124 on the handle 62 (see FIGS. 15A and 15B).

When the gripper arms 116 are maintained by the cam element 120 in their outwardly deflected condition (see FIG. 14B), the tabs 126 lock into the mounts 110 on the fastener cap 108, securing the fastener assembly 102 to the carrier 104. Conversely, when the cam element 120 is withdrawn, the tabs 126 allow the fastener assembly 102 to be inserted onto or separated from the carrier 104.

In use, the physician pulls back on the control 124 to withdraw the cam element 120 against the bias of the spring 122 and snap-fits a fastener assembly 102 onto the carrier 104. The physician then releases the control 124 to allow the spring 122 to return forward and lock the fastener assembly 102 onto the carrier 104. The physician then deploys the catheter 42 holding the fastener assembly 102 to targeted site (see FIG. 15A). By rotating the carrier 104, the physician implants the fastener assembly 102 into the prosthesis 10/tissue wall.

When the fastener assembly 102 has been satisfactorily implanted, the physician pulls back on the control 124 and the catheter 42 (see FIG. 15B) to separate the fastener assembly 102 from the carrier 104. The physician withdraws the catheter 42 and repeats the forgoing steps until the desired number of fastener assemblies 102 has been implanted.

Carriers with Two-Phase Ejection of Fasteners

The above-described embodiments a provide the ability to withdraw a given fastener from a prosthesis/tissue wall prior to completion of the implantation step. The above-described embodiments make this feature possible by providing a fastener applier 38 that includes a fastener release mechanism that works independent of the fastener implantation mechanism.

Figure 16B:
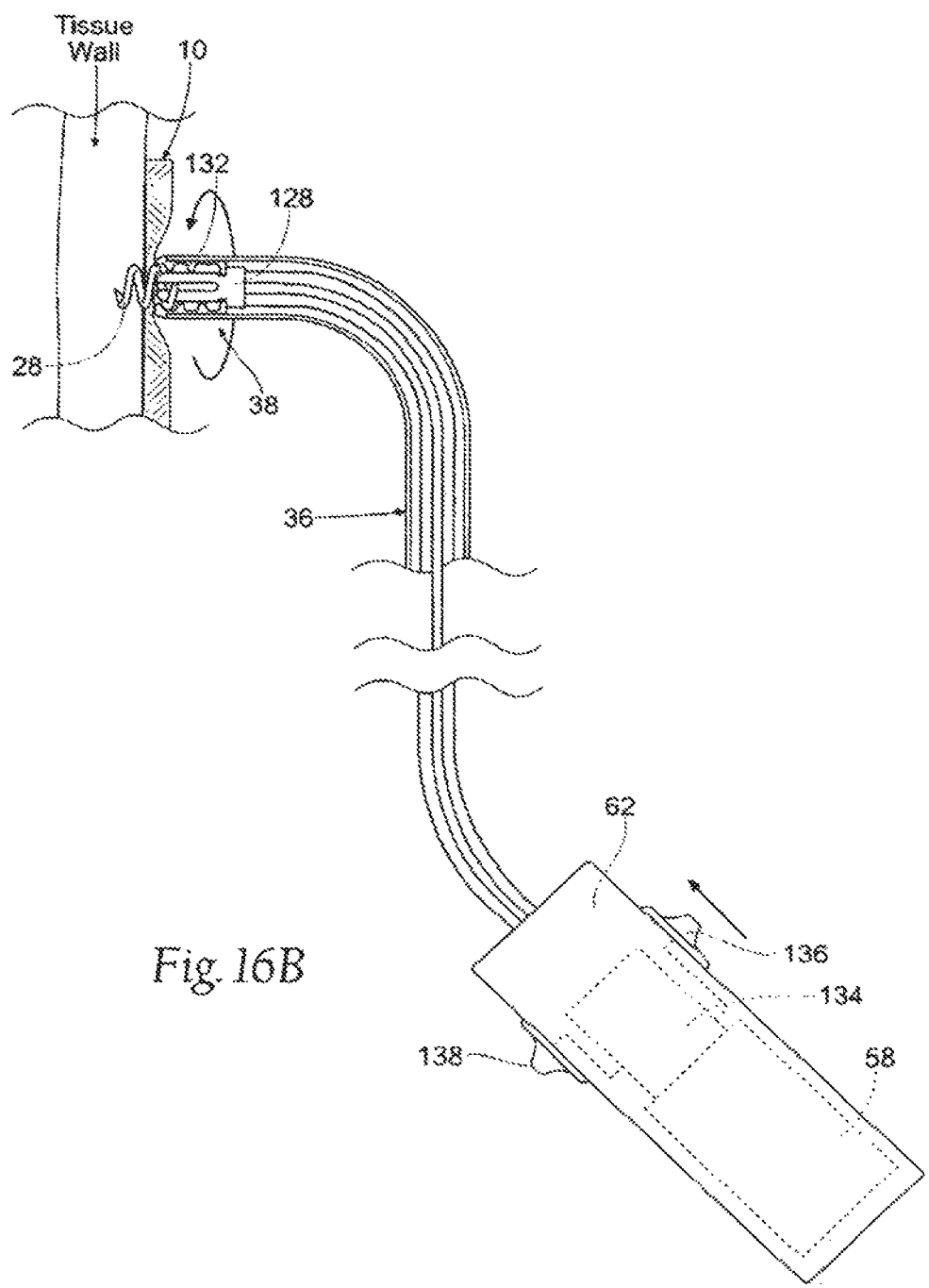
FIG. 16B is a side view, partly broken away and in section, of the fastener applier shown in FIG. 16A(2), the carrier being shown at the end of a first operating phase, during which the fastener has been partially implanted in a prosthesis/tissue wall and in which the fastener remains secured to the carrier.

In FIGS. 16A(1)/A(2), 16B, and 16C, a fastener applier 38 includes a fastener carrier 128 that implements this feature without an independent release mechanism. In FIGS. 16A(1)/A(2), 16B, and 16C, the fastener carrier 128 is operated in two phases. The first or initial phase advances a fastener 28 into an incomplete implantation position within a prosthesis 10/tissue wall (FIG. 16B), which represents a sufficient distance to gain purchase, but which is short of full implantation. That is, given that full implantation of the fastener 28 requires the application of an implantation force under prescribed conditions, i.e., for a prescribed time period or for a prescribed number of rotations of the fastener 28 during the first phase under conditions that do not achieve the prescribed conditions. Thus, full implantation is not achieved. During the first phase, the fastener 28 remains coupled to the fastener carrier 128, to allow the physician to operate the fastener carrier 128 to withdraw/retrieve the fastener 28, if desired (see FIG. 16D).

The first phase presents a decision point to that physician. At end of the first phase, a lull phase exists, during which operation of the fastener carrier 128 is interrupted. A prescribed input command is required to move out of the lull phase. During the lull phase, the physician can elect to withdraw or retrieve the fastener 28 (FIG. 16D). Alternatively, the physician can elect to continue implantation or proceed to the second phase. In the second or final phase, the fastener carrier 128 advances the fastener 28 from the incomplete implantation position (FIG. 16B) to the complete implantation position (FIG. 16C), at the end of which the fastener 28 itself automatically separates from the fastener carrier 128. That is, during the second phase, implantation force is applied to the fastener 28 under conditions that supplement the conditions of the first phase in order to meet the conditions prescribed for full implantation.

The fastener applier 38 can implement this feature in various structural embodiments. In the illustrative embodiment shown in FIG. 16A(1), the carrier 128, coupled to a driver 52, includes a slot 130, which receives the L-shaped leg 66 to couple the fastener 28 for rotation with the carrier 128. In this embodiment, the turns of the coil 54 rest is complementary internal grooves 132 that surround the carrier 128. The grooves 132 could be positioned along the entire length of the fastener 28 or within a portion of its length. Activation of the drive mechanism rotates, as a unit, the driver 52, the carrier 128, and the helical fastener 28 (as FIG. 16A(2) shows). This rotation causes the helical fastener 28 to travel within the internal grooves 132 of the fastener applier and into the prosthesis 10 and tissue wall. Uninterrupted rotation of the carrier 128 will cause the helical fastener 28 to be rotates completely off the carrier and through the prosthesis 10 and into the tissue wall (as FIG. 16C shows).

In the illustrated embodiment, the drive mechanism includes a motor control unit 134 (see FIGS. 16A(2), and 16B, and 16D). The motor control unit 134 is conditioned to operate the carrier 128 in the two distinct phases, as above described. The first phase of fastener implantation is initiated by the physician activating a rotation command, e.g., by manipulating a first switch 136 on the handle 62. During the first phase of deployment (FIG. 16B), the carrier 128 is driven sufficient to rotate the helical fastener 28 to a position in which the distal portion of the fastener 28 has implanted itself into the target tissue, but in which the proximal portion of the fastener 28 is still retained within the internal threads 132 of the carrier 128. At this point, the first phase ends, and the motor control unit 134 enters the lull phase, automatically interrupting rotation of the carrier 128. The motor control unit 134 can accomplish motor control in this fashion by either conventional mechanical and or electronic means, e.g., through a programmable microprocessor.

At this juncture, the physician has the option of reversing the insertion process and removing the fastener 28, if desired (see FIG. 16D), e.g., by reversing the switch 136 or activating another switch 138 on the handle 62. At this juncture, the physician also has the option of completing the implantation process, e.g., by manipulating the switch 136 in a preprogrammed fashion (for example, by double switching).

In one variation, the motor control unit 136 can receive input reflecting a performance criteria measure during the first phase of deployment. The motor control unit 136 assesses the value of the performance criteria, to determine whether it falls within a predetermined acceptable range. If so, the second phase of deployment may occur automatically without a pause and without a second input from the user. For example, motor current used during the first phase of fastener deployment could be measured, and from this the fastener driving torque can be calculated. A torque within a range of acceptable values would imply that the fastener 28 has successfully entered the target tissue and fastener implantation could be completed automatically. A torque that was outside the acceptable range could result in either a pause at the end of phase one, where the user could make the decision to continue or reverse the fastener deployment, or an automatic reversal of fastener deployment.

In an alternative embodiment, a fastener release mechanism 114 of the type shown, e.g., in FIGS. 13A/B and 14A/B can be used in association with a motor control unit 134. In this arrangement, the motor control unit 134 is conditioned to operate the carrier 104 to drive the fastener assembly 102 in a single phase of deployment into tissue. At this point, the release mechanism 114 can be operated in the manner previously described, to separate the fastener assembly 102 from the carrier 104. The motor control unit 134 can be conditioned by mechanical and/or electronic means to indicate and/or control the number of revolutions and/or control the number of revolutions and/or the torque applied to accomplish the installation of the fastener assembly 102 in tissue. In this embodiment, there is no need for multiple phase, because the physician ultimately controls the release of the fastener assembly 102 by manipulation of the release mechanism 114.

Carriers with Tethered Fasteners

Figure 17A:
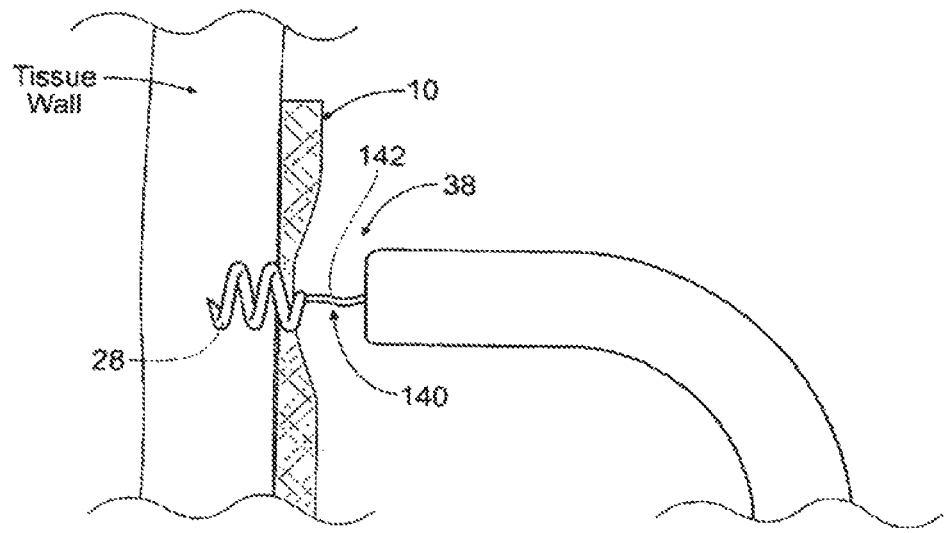
FIGS. 17A and 17B are side views of a fastener applier of the type shown in any of the preceding figures, the fastener applier including an element releasably tethering a fastener to the fastener applier, FIG. 17A showing the tethering element holding on to the fastener following its implantation in a prosthesis/tissue wall, and FIG. 17B showing the tethering element after having been parted from the fastener.

In all of the above embodiments, or as an alternative embodiment in and of itself, a fastener applier 38 can include an element 140 to releasably tether a fastener 28 to the applier 38 even after the fastener 28 has been separated from the applier 38 (see FIG. 17A). The tether element 140 serves as a "life line," maintaining a connection of last resort between the applier 38 and a fastener 28. The tether element 28 allows the fastener 28 to be retrieved if, for any reason, the fastener 28 inadvertently breaks loose from tissue and/or the applier 38 during or after implantation. The connection between the tether element 140 and the applier 38 requires a deliberate act of the physician to be broken, adding a confirming, a final step to the implantation process (see FIG. 17B).

Figure 17B:
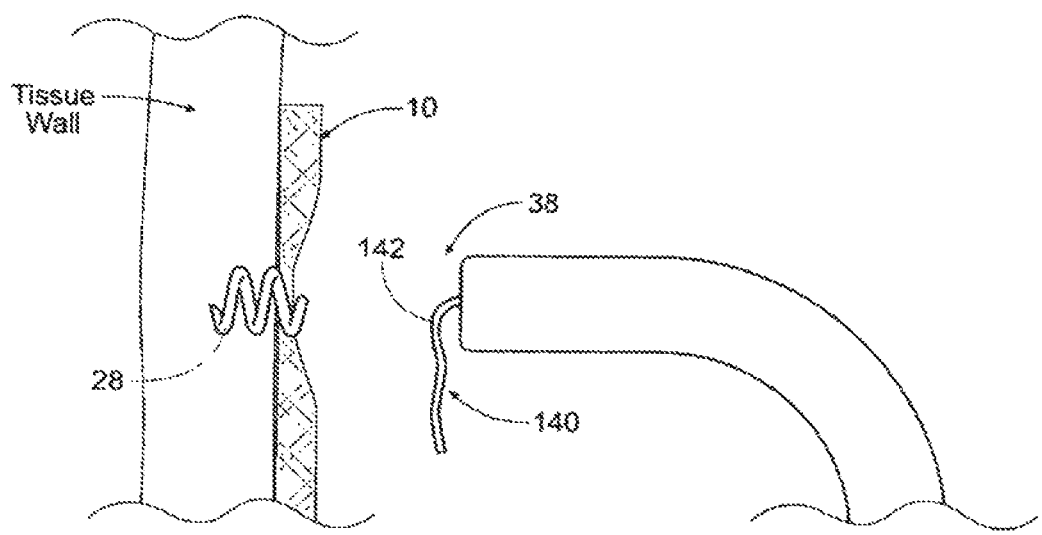

The tether element 140 can be variously constructed. In FIG. 17A, the tether element 140 comprises a thread, braid, wire, or tubing structure 142. The proximal end of the tether element structure 142 is attached to the fastener applier 38 in a manner that can be detached by application of a deliberate pulling force. The distal end of the tether element structure 142 is frangible and can be broken by a force less than the deliberate pulling force once desired deployment of the fastener 28 is confirmed, as FIG. 17B shows. The tether element structure 142 has sufficient length to be able to retract the fastener applier 38 enough to visualize the fastener in position (as FIG. 17A shows). The force to break the frangible distal end of the tether element structure 142 is less than the force required to dislodge the fastener 28 from tissue. Desirably, the frangible distal end of the tether element structure 142 detaches from the fastener 28 without leaving remnants on the fastener 28 (as FIG. 17B shows).

Figure 18A:
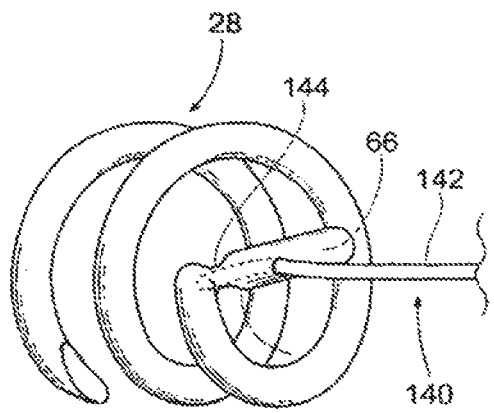
FIGS. 18A and 18B show an embodiment of a tethering element of the type shown in FIGS. 17A and 17B, the tethering element being secure to a frangible portion of the fastener, FIG. 18A showing the tethering element holding on to the fastener following its implantation in a prosthesis/tissue wall, and FIG. 18B showing the tethering element after having been parted from the fastener.
Figure 18B:
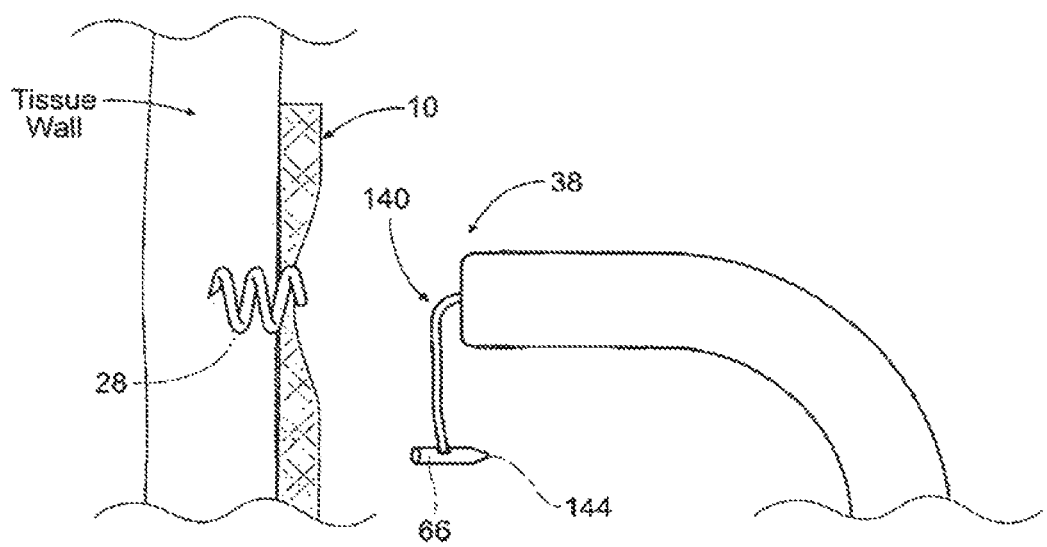

The tether element structure 142 can be sized and configured in other, different ways to form a frangible connection with a fastener 28. For example (see FIGS. 18A and 18B), the L-shaped leg 66 could be crimped to form an area of weakness 144 (FIG. 18A), to which the tether element structure 142 applies force to free the tether element structure 142 from the fastener 28 (FIG. 18B).

Figure 19A:
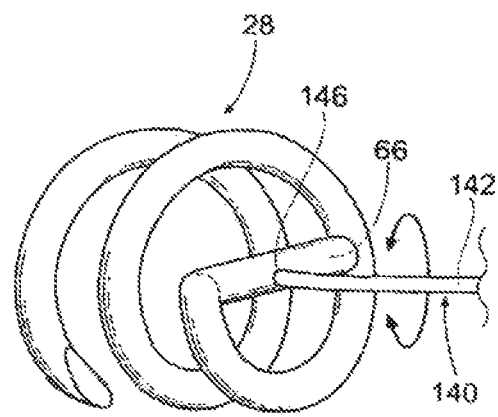
FIG. 19A shows an embodiment of a tethering element of the type shown in FIGS. 17A and 17B, the tethering element being secured to a frangible joint that is broken by rotating the tethering element relative to the fastener.
Figure 19B:
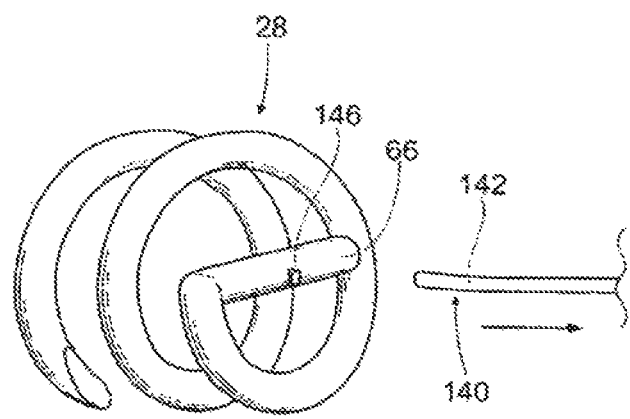
FIG. 19B shows an embodiment of a tethering element of the type shown in FIGS. 17A and 17B, the tethering element being secured to a frangible joint that is broken by pulling the tethering element from the fastener.
Figure 20A:
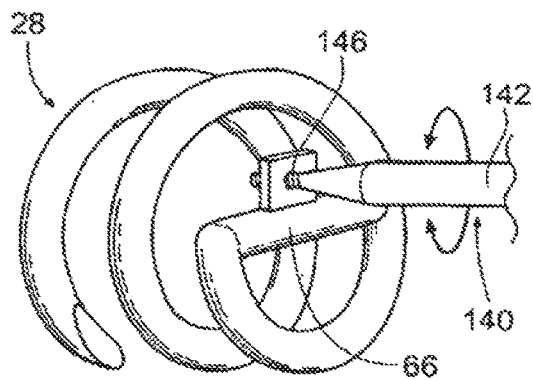
FIGS. 20A and 20B show an embodiment of a tethering element of the type shown in FIGS. 17A and 17B, the tethering element being secured to a screw joint (FIG. 20A) that is parted by rotating the tethering element relative to the fastener (FIG. 20B).
Figure 20B:
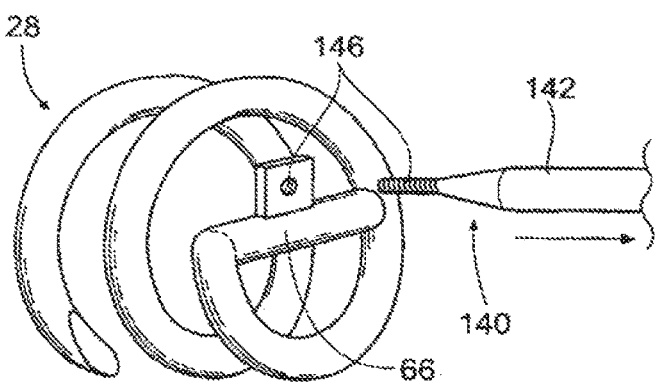
Figure 21A:
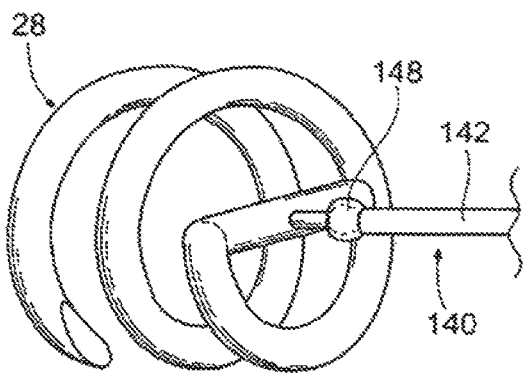
FIGS. 21A and 21B show an embodiment of a tethering element of the type shown in FIGS. 17A and 17B, the tethering element being secured to a ball joint (FIG. 21A) that is parted by pulling the tethering element away from the fastener (FIG. 21B).
Figure 21B:
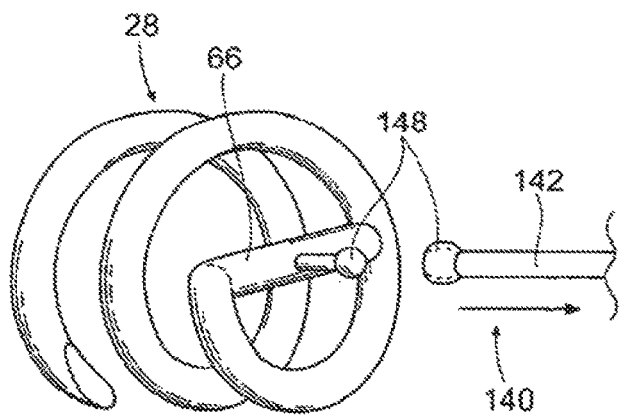
Figure 22A:
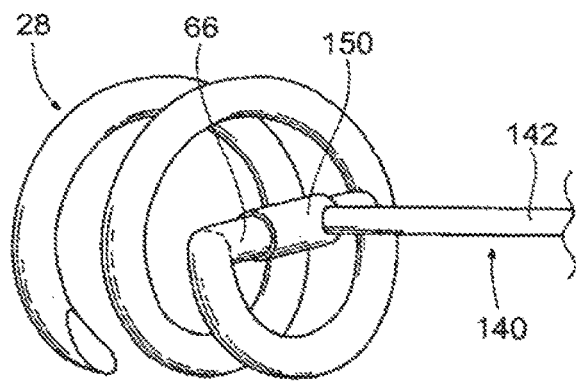
FIGS. 22A and 22B show an embodiment of a tethering element of the type shown in FIGS. 17A and 17B, the tethering element being secured to a slip joint (FIG. 22A) that is parted by pulling the tethering element away from the fastener (FIG. 22B).
Figure 22B:
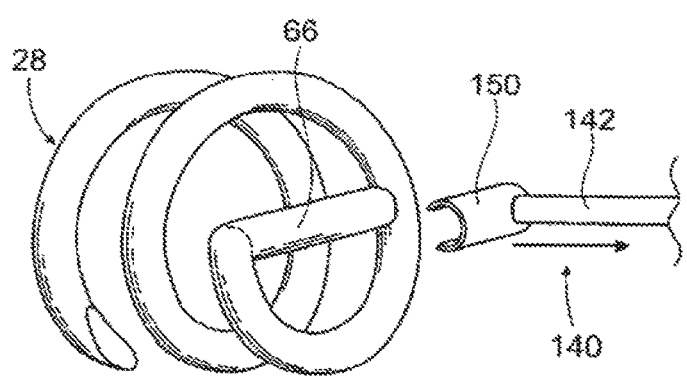
Figure 23A:
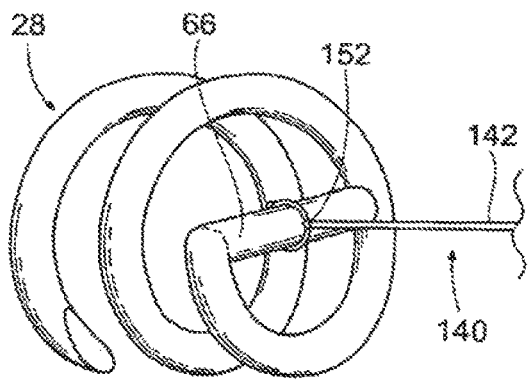
FIGS. 23A and 23B show an embodiment of a tethering element of the type shown in FIGS. 17A and 17B, the tethering element being secured to a knotted joint (FIG. 23A) that is parted by pulling the tethering element away from the fastener (FIG. 23B).
Figure 23B:
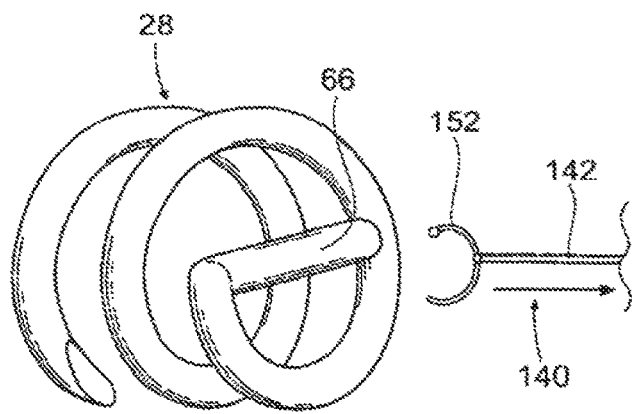
Figure 24A:
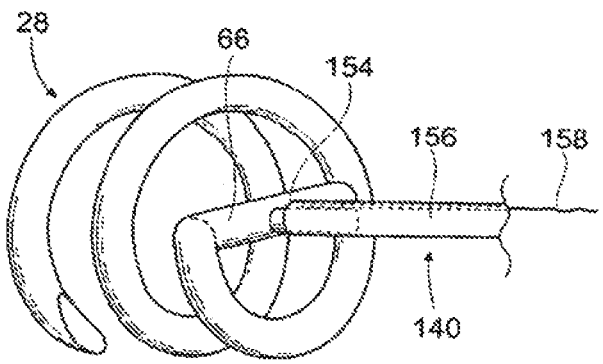
FIGS. 24A and 24B show an embodiment of a tethering element of the type shown in FIGS. 17A and 17B, the tethering element being secured to a frangible tube joint (FIG. 24A) that is parted by pulling a rip cord (FIG. 24B).
Figure 24B:
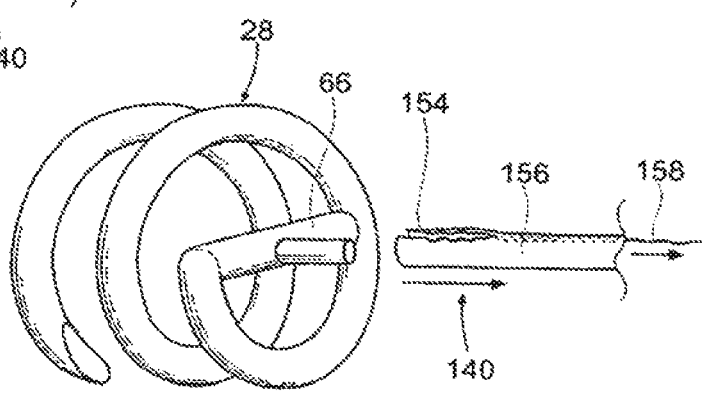
Figure 25A:
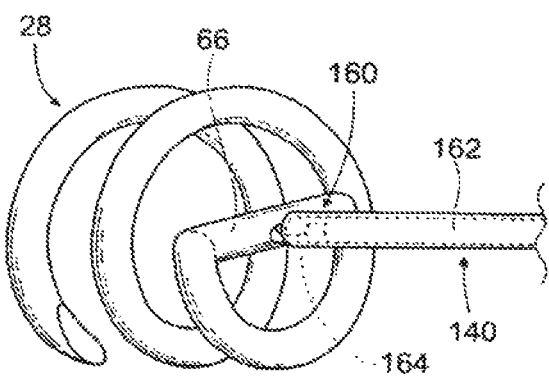
FIGS. 25A and 25B show an embodiment of a tethering element of the type shown in FIGS. 17A and 17B, the tethering element including an interlocking mechanism.
Figure 25B:
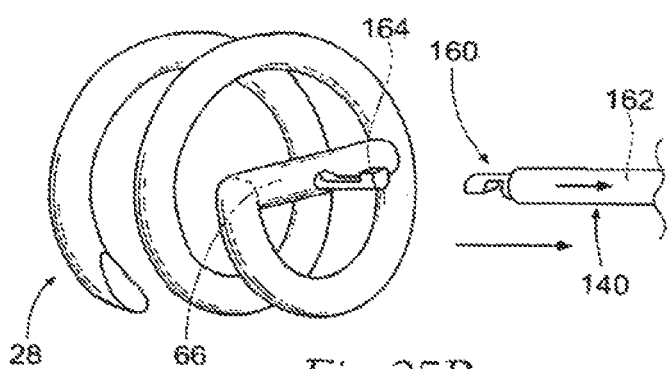

Alternatively, the junction between the tether element structure 142 and the fastener 28 can comprise an area of weakness 146 (e.g., be welding, soldering, gluing, heating, or shearing) that is broken by the application of a prescribed force in a prescribed manner, e.g., by rotation (FIG. 19A) or pulling (FIG. 19B). Alternatively, the junction between the tether element structure 142 and the fastener 28 may comprise a threaded joint 146 (see FIGS. 20A and 20B), or a snap-fit ball and socket joint 148 (see FIGS. 21A and 21B), or slide-fit joint 150 (see FIGS. 22 A and 22B; or a knotted joint 152 (FIGS. 23A and 23B); or a frictional junction 154 that is relieved by split open a tube 156 using a rip cord 158 (FIGS. 24A and 24B). Still, alternatively, the junction between the tether element 140 and the fastener 28 can comprise an interlocking mechanism 160, for example, a slidable outer sleeve 162 that, when advanced (FIG. 25A), captures an appendage 164 on the fastener 28 and, when retracted (FIG. 25B), frees the appendage 164.

The preferred embodiments of the invention are described above in detail for the purpose of setting forth a complete disclosure and for the sake of explanation and clarity. Those skilled in the art will envision other modifications within the scope and sprit of the present disclosure.

We claim:

1. A tool for applying an implantation force to a fastener sized and configured for implantation in tissue in response to an implantation force applied according to prescribed conditions, the tool comprising:
   a tool body;
   a driven member carried by the tool body and being operable to apply the implantation force;
   a mechanism on the driven member to couple the fastener to the driven member to transfer the implantation force from the driven member to the fastener; and
   a controller coupled to the driven member, the controller including:
   an initial phase operating the driven member to apply the implantation force under conditions than are short of the prescribed conditions;
   a lull phase commencing at the end of the initial phase interrupting operation of the driven member;
   a final phase operating the driven member under conditions that supplement the conditions of the initial phase to achieve the prescribed conditions,
   the controller requiring, after the initial phase, a prescribed command to advance from the lull phase to the final phase;
   wherein the prescribed conditions are a prescribed time period or a prescribed number of rotations.

2. The tool of claim 1, wherein the prescribed command is based, at least in part, upon input from an operator.

3. The tool of claim 1, wherein the prescribed command is based, at least in part, upon input reflecting a sensed operating condition.

4. The tool of claim 1, wherein:
   the driven member is operable to apply a removal force to withdraw the fastener from tissue; and
   the controller includes a removal phase operating the driven member to apply the removal force, the controller requiring, after the initial phase, a different prescribed command to advance from the lull phase to the removal phase.

5. The tool of claim 4, wherein the driven member is rotated in one direction to apply the implantation force and rotated in an opposite direction to apply the removal force.

6. The tool of claim 1, further comprising an element configured to tether the fastener to the tool body, the element comprising a frangible portion.

7. The tool of claim 1, wherein the driven member is rotated to apply the implantation force.

8. The tool of claim 1, wherein the tool body comprises a tubular member that carries the driven member and the mechanism.

9. The tool of claim 1, wherein:
   the tool body comprises internal threads and the fastener comprises a helical fastener; and
   a proximal portion of the helical fastener is retained within the internal threads at the end of the initial phase.

10. The tool of claim 1, wherein the mechanism comprises a distal portion having a configuration that corresponds to a configuration of a proximal end of the fastener, such that the proximal end of the fastener engages with the distal portion of the mechanism to couple the fastener to the mechanism throughout the initial phase.

11. The tool of claim 10, wherein the proximal end of the fastener comprises a leg portion that engages with the distal portion of the mechanism throughout the initial phase.

12. The tool of claim 1, wherein the fastener comprises a helical fastener.

* * * * *